US008067415B2

(12) United States Patent
Elder et al.

(10) Patent No.: US 8,067,415 B2
(45) Date of Patent: Nov. 29, 2011

(54) COMPOUNDS USEFUL AS ANTAGONISTS OF CCR2

(75) Inventors: Amy M. Elder, Arlington, MA (US); Shomir Ghosh, Brookline, MA (US); Sian Griffiths, Westborough, MA (US); Prakash Raman, Acton, MA (US); Francois Soucy, Stoneham, MA (US); Kevin Sprott, Boston, MA (US); Qing Ye, Westborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/084,353

(22) PCT Filed: Oct. 26, 2006

(86) PCT No.: PCT/US2006/042181
§ 371 (c)(1),
(2), (4) Date: Feb. 19, 2009

(87) PCT Pub. No.: WO2007/053499
PCT Pub. Date: May 10, 2007

(65) Prior Publication Data
US 2009/0163497 A1 Jun. 25, 2009

Related U.S. Application Data

(60) Provisional application No. 60/732,344, filed on Nov. 1, 2005.

(51) Int. Cl.
| A61K 31/505 | (2006.01) |
| A61K 31/498 | (2006.01) |
| A61K 31/435 | (2006.01) |
| A61K 31/4184 | (2006.01) |
| C07D 487/22 | (2006.01) |
| C07D 487/12 | (2006.01) |
| C07D 241/00 | (2006.01) |
| C07D 491/14 | (2006.01) |
| C07D 491/22 | (2006.01) |
| C07D 235/04 | (2006.01) |

(52) U.S. Cl. .......... 514/249; 514/259.1; 514/300; 514/387; 544/281; 544/349; 546/121; 548/304.4

(58) Field of Classification Search ............ 514/249, 514/259.1, 300, 387; 544/281, 349; 546/121; 548/304.4
See application file for complete search history.

(56) References Cited

U.S. PATENT DOCUMENTS

| 4,237,272 | A | 12/1980 | Mochida et al. |
| 4,309,546 | A | 1/1982 | Karrer |
| 5,338,853 | A | 8/1994 | MacLeay et al. |
| 5,356,904 | A | 10/1994 | Freidinger et al. |
| 5,397,821 | A | 3/1995 | MacLeay et al. |
| 5,688,960 | A | 11/1997 | Shankar |
| 5,696,267 | A | 12/1997 | Reichard et al. |
| 6,143,750 | A | 11/2000 | Patane et al. |
| 6,225,324 | B1 | 5/2001 | Poss et al. |
| 6,313,117 | B1 | 11/2001 | Bekkali et al. |
| 6,369,077 | B1 | 4/2002 | Marquis et al. |
| 6,627,629 | B2 | 9/2003 | Ko et al. |
| 6,649,642 | B2 | 11/2003 | Bekkali et al. |
| 6,720,319 | B2 | 4/2004 | Liu et al. |
| 6,740,649 | B2 | 5/2004 | Ott et al. |
| 6,743,807 | B2 | 6/2004 | Duan et al. |
| 6,858,623 | B2 | 2/2005 | Bekkali et al. |
| 6,949,546 | B2 | 9/2005 | Ko et al. |
| 6,979,690 | B2 | 12/2005 | Gymer et al. |
| 6,979,741 | B2 | 12/2005 | Perry et al. |
| 6,984,648 | B2 | 1/2006 | Lu et al. |
| 7,163,937 | B2 | 1/2007 | Carter et al. |
| 7,169,795 | B2 | 1/2007 | Han et al. |
| 7,183,270 | B2 | 2/2007 | Cherney et al. |
| 7,307,086 | B2 | 12/2007 | Xue et al. |
| 7,312,218 | B2 | 12/2007 | Han et al. |
| 7,338,947 | B2 | 3/2008 | Cherney et al. |
| 7,378,409 | B2 | 5/2008 | Carter et al. |
| 2005/0176738 | A1* | 8/2005 | Goodfellow et al. ...... 514/260.1 |
| 2006/0135575 | A1 | 6/2006 | Carayon et al. |
| 2007/0179126 | A1 | 8/2007 | Casellas et al. |
| 2009/0197884 | A1 | 8/2009 | Ghosh et al. |
| 2010/0016289 | A1 | 1/2010 | Sprott et al. |

FOREIGN PATENT DOCUMENTS

| EP | 382185 B1 | 8/1990 |
| EP | 516192 A2 | 12/1992 |
| EP | 1325921 A2 | 7/2003 |
| JP | 63083082 | 4/1988 |
| JP | 10298180 | 11/1998 |

(Continued)

OTHER PUBLICATIONS

Office Action dated Jun. 30, 2010 (Part of Paper No. 20100519) in U.S. Appl. No. 12/084,356, filed Apr. 15, 2009. Butler, Todd W., et al., "(3R,4S)-3-[4-(4-Fluorophenyl)-4-hydroxypiperidin-1-yl]chroman-4,7-diol: A Conformationally Restricted Analogue of the NR2B Subtype-Selective NMDA Antagonist (1S,2S)-1-(4-Hydroxyphenyl)-2-(4-hydroxy-4-phenylpiperidino)-1-propanol," *Journal of Medicinal Chemistry*, vol. 41, No. 7 (1998) pp. 1172-1184.

Feria, Manuel, et al., "The CCR2 receptor as a therapeutic target," *Expert Opinion on Therapeutic Patents*, vol. 16, No. 1 (2006) pp. 49-57.

Grey, Jonathan, et al., "Bis(aminopyrrolidine)-derived ureas (APUs) as potent MCH$_1$ receptor antagonists," *Bioorganic & Medicinal Chemistry Letters*, vol. 15, No. 4 (2005) pp. 999-1004.

Stephen, John F., et al., "Preparation of bicyclic enamines and their reaction with sulfene," *Journal of Organic Chemistry*, vol. 34, No. 9 (Sep. 1969) pp. 2535-2542.

(Continued)

*Primary Examiner* — Rebecca Anderson
*Assistant Examiner* — Samantha Shterengarts

(57) ABSTRACT

The present invention provides compounds of general formula (I) or a pharmaceutically acceptable salt thereof, wherein X, n, Y, and $R^1$ are defined generally and in subsets herein. Compounds of the invention are inhibitors of CCR2 and accordingly are useful for the treatment of a variety of inflammatory, allergic, and autoimmune diseases, disorders, or conditions.

(I)

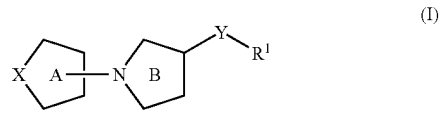

26 Claims, No Drawings

FOREIGN PATENT DOCUMENTS

| | | |
|---|---|---|
| WO | WO 95/08533 A1 | 3/1995 |
| WO | WO 95/19773 A1 | 7/1995 |
| WO | WO 96/34856 A1 | 11/1996 |
| WO | WO 97/48397 A1 | 12/1997 |
| WO | WO 97/48695 A1 | 12/1997 |
| WO | WO 97/48696 A1 | 12/1997 |
| WO | WO 98/50534 A1 | 11/1998 |
| WO | WO 98/57640 A1 | 12/1998 |
| WO | WO 99/53920 A1 | 10/1999 |
| WO | WO 00/44376 A1 | 8/2000 |
| WO | WO 00/69816 A1 | 11/2000 |
| WO | WO 01/09110 A1 | 2/2001 |
| WO | WO 01/19816 A1 | 3/2001 |
| WO | WO 01/70673 A2 | 9/2001 |
| WO | WO 02/02525 A2 | 1/2002 |
| WO | WO 02/13824 A1 | 2/2002 |
| WO | WO 02/060859 A2 | 8/2002 |
| WO | WO 02/062784 A1 | 8/2002 |
| WO | WO 03/024899 A2 | 3/2003 |
| WO | WO 03/057688 A2 | 7/2003 |
| WO | WO 03/072197 A1 | 9/2003 |
| WO | WO 03/075853 A2 | 9/2003 |
| WO | WO 03/076403 A1 | 9/2003 |
| WO | WO 03/092586 A2 | 11/2003 |
| WO | WO 03/093231 A2 | 11/2003 |
| WO | WO 03/093266 A1 | 11/2003 |
| WO | WO 03/093297 A2 | 11/2003 |
| WO | WO 2004/041161 A2 | 5/2004 |
| WO | WO 2004/041163 A2 | 5/2004 |
| WO | WO 2004/041777 A2 | 5/2004 |
| WO | WO 2004/050024 A2 | 6/2004 |
| WO | WO 2004/071449 A2 | 8/2004 |
| WO | WO 2004/071460 A2 | 8/2004 |
| WO | WO 2004/076411 A2 | 9/2004 |
| WO | WO 2004/081005 A1 | 9/2004 |
| WO | WO 2004/082616 A2 | 9/2004 |
| WO | WO 2004/082682 A1 | 9/2004 |
| WO | WO 2004/092124 A2 | 10/2004 |
| WO | WO 2004/094371 A2 | 11/2004 |
| WO | WO 2004/096798 A2 | 11/2004 |
| WO | WO 2004/098512 A2 | 11/2004 |
| WO | WO 2004/098516 A2 | 11/2004 |
| WO | WO 2005/010154 A2 | 2/2005 |
| WO | WO 2005/014537 A2 | 2/2005 |
| WO | WO 2005/020899 A2 | 3/2005 |
| WO | WO 2005/021498 A1 | 3/2005 |
| WO | WO 2005/021500 A1 | 3/2005 |
| WO | WO 2005/037216 A2 | 4/2005 |
| WO | WO 2005/047293 A1 | 5/2005 |
| WO | WO 2005/048922 A2 | 6/2005 |
| WO | WO 2005/060665 A2 | 7/2005 |
| WO | WO 2005/070133 A2 | 8/2005 |
| WO | WO 2005/072361 A2 | 8/2005 |
| WO | WO 2005/077369 A1 | 8/2005 |
| WO | WO 2005/079519 A2 | 9/2005 |
| WO | WO 2005/080371 A1 | 9/2005 |
| WO | WO 2005/105092 A2 | 11/2005 |
| WO | WO 2005/115392 A2 | 12/2005 |
| WO | WO 2005/117890 A2 | 12/2005 |
| WO | WO 2005/120505 A2 | 12/2005 |
| WO | WO 2006/001958 A2 | 1/2006 |
| WO | WO 2006/004684 A2 | 1/2006 |
| WO | WO 2006/004741 A2 | 1/2006 |
| WO | WO 2007/053495 A2 | 5/2007 |
| WO | WO 2007/053498 A1 | 5/2007 |
| WO | WO 2007/072201 A2 | 6/2007 |

OTHER PUBLICATIONS

Ting, Pauline C., et al., "The synthesis of substituted bipiperidine amide compounds as CCR3 antagonists," *Bioorganic & Medicinal Chemistry Letters*, vol. 15, No. 5 (2005) pp. 1375-1378.

Torii, Sigeru, et al., "Penicillin-cephalosporin conversion. X. New synthesis of dithioazetidinones from thiazoline-azetidinones," *Tetrahedron Letters*, vol. 25, No. 19 (1984) pp. 2017-2020.

Woods, J.H., et al., "Evaluation of new compounds for opioid activity," *NIDA Research Monograph*, vol. 179 (Problems of drug dependence, 1998) pp. 365-380.

Yang, Yulong, et al., "Synthesis and anesthetic activity of 3-methyl fentanyl derivatives," *Zhongguo Yaoke Daxue Xuebao*, vol. 24, No. 5 (1993) pp. 257-263.

International Search Report and Written Opinion dated Apr. 20, 2007 cited in corresponding PCT application PCT/US06/042181 (WO07/053499).

International Search Report and Written Opinion dated Mar. 30, 2007 cited in PCT application PCT/US06/042180 (WO07/053498).

International Search Report and Written Opinion dated May 10, 2007 cited in PCT application PCT/US06/042170 (WO07/053495).

Office Action dated Feb. 24, 2011 (Part of Paper No. 20110104-A) in U.S. Appl. No. 12/084,356 (filed Apr. 15, 2009).

* cited by examiner

COMPOUNDS USEFUL AS ANTAGONISTS OF CCR2

BACKGROUND OF THE INVENTION

Chemoattractant cytokines, Chemoattractant cytokines or chemokines are a family of proinflammatory mediators that are released by a wide variety of cells to promote recruitment and activation of cells such as T and B lymphocytes, eosinophils, basophils, and neutrophils (Luster et al. *New Eng. J. Med*, 1998, 338, 436). The chemokines are related in primary structure and contain four conserved cysteines, which form disulfide bonds. The chemokine family includes the C—X—C chemokines (α-chemokines), and the C—C chemokines (β-chemokines), in which the first two conserved cysteines are separated by an intervening residue, or are adjacent, respectively (Baggiolini, M. and Dahinden, C. A., *Immunology Today*, 1994, 15, 127).

Chemokines exert their biological activity by binding to specific cell-surface receptors belonging to the family of G-protein-coupled seven-transmembrane-domain proteins (Horuk, *Trends Pharm. Sci.* 1994, 15, 159) which are termed "chemokine receptors". On binding their cognate ligands, chemokine receptors then transduce signals important for the development and trafficking of specific leukocyte subsets (Baggiolini, et. al., *Nature* 1994, 15, 365). The chemokines and their cognate receptors have been implicated as being important mediators of inflammatory, and allergic diseases, disorders, and conditions, as well as autoimmune pathologies such as rheumatoid arthritis and atherosclerosis (see, Carter, *Current Opinion in Chemical Biology* 2002, 6, 510; Trivedi et al., *Ann. Reports Med. Chem.* 2000, 35, 191; Saunders et al., *Drug Disc. Today* 1999, 4, 80; and Premack et al., *Nature Medicine*, 1996, 2, 1174). Accordingly, agents that block the interaction of chemokines with their cognate receptors would be useful in treating inflammatory, allergic, and autoimmune diseases, disorders, or conditions caused by aberrant activation of leukocytes or lymphocytes.

CCR2 is a chemokine receptor expressed on monocytes which recognizes the ligands MCP-1, MCP-2, MCP-3, and MCP-4 (see, Berkhout, et al., *J. Biol. Chem.* 1997, 272, 16404. It has been implicated that the interaction of monocyte chemoattractant protein-1 (MCP-1) and its receptor (CCR2) plays a role in the pathogenesis of inflammatory, allergic, and autoimmune diseases (for example rheumatoid arthritis, multiple sclerosis, COPD, neuropathic pain, asthma, and atherosclerosis) by attracting leukocytes to sites of inflammation and subsequently activating these cells. When the chemokine MCP-1 binds to CCR2, it induces a rapid increase in intracellular calcium concentration, increased expression of cellular adhesion molecules, cellular degranulation, and the promotion of leukocyte migration. (see Dawson, et al., *Expert Opin. Ther. Targets*, 2003, 7, 35; Gongh et al., *J. Exp. Med.* 1997, 181, 131; Izikson, et al., *Clin. Immunol.* 2002, 103, 125; Donnelly et al., *Drugs*, 2003, 63, 1973; Leonard, E. J. *Challenges Mod. Med.*, 1994, 3, 25; and Ross, R. *New Engl. J. Med.* 1999, 147, 213). In particular, monocyte chemoattractant protein-1 (MCP-1) is believed to be primarily responsible for the selective recruitment of leukocytes to the site of inflammation by binding to its receptor CCR2 on the surface of monocytes and macrophages (Rollins et al., *Blood*, 1997, 90, 909; Howard et al., *Trends Biotechiol.* 1996, 14, 46; Saunders et al., *Drug Discovery Today*, 1999, 4, 80; Murphy et al., *Pharmacologic Rev.*, 2000, 52, 145; and Horuk, R. *Cytokine Growth Factor Rev.*, 2001, 12, 313). The importance of the MCP-1/CCR2 interaction has been demonstrated by experiments with genetically modified mice (see, Bao, et al., *J. Exp. Med.* 1998, 187, 601; Boring et al., *J. Clin. Invest.* 1997, 100, 2552; Kuziel et al., *Proc. Natl. Acad. Sci. USA*, 1997, 94, 12053; and Kurihara et al., *J. Exp. Med.* 1997, 186, 1757). Several studies have also been published indicating that therapeutic intervention at the CCR2 receptor via inhibition of the interaction between MCP-1 and CCR2 may have beneficial effects in a variety of inflammatory, allergic, and autoimmune diseases. For example, studies completed to date have indicated that the antagonisum of the MCP-1/CCR2 interaction may be useful in treating rheumatoid arthritis; ameliorate chronic polyadjuvant-induced arthritis (Youssef et al., *J. Clin. Invest.* 2000, 106, 361); collagen-induced arthritis (Ogata et al., *J. Pathol.* 1997, 182, 106); streptococcal cell wall-induced arthritis (Schimmer et al., *J. Immunol.* 1998, 160, 1466); MRL-1pr mouse model of arthritis (Gong et al., *J. Exp. Med.* 1997, 186, 131); atherosclerosis (Rezaie-Majd et al, *Arterioscler. Thromb. Vasc. Biol.* 2002, 22, 1194-1199; Gu et al., *Mol. Cell.* 1998, 2, 275; Gosling et al., *J. Clin. Invest.* 1999, 103, 773; Boring et al, *Nature* 1998, 394, 894; and Ni et al. *Circulation* 2001, 103, 2096-2101); multiple sclerosis (Iarlori et al., *J. Neuroimmunol.* 2002, 123, 170-179; Kennedy et al., *J. Neuroimmunol.* 1998, 92, 98; Fife et al., *J. Exp. Med.* 2000, 192, 899; and Izikson et al., *J. Exp. Med.* 2000, 192, 1075); organ transplant rejection (Reynaud-Gaubert et al., *J. of Heart and Lung Transplant.*, 2002, 21, 721-730; Belperio et al., *J. Clin. Invest.* 2001, 108, 547-556; and Belperio et al., *J. Clin. Invest.* 2001, 108, 547-556); asthma (Gonzalo et al., *J. Exp. Med.* 1998, 188, 157; Lukacs, et al., *J. Immunol.* 1997, 158, 4398; and Lu et al., *J. Exp. Med.* 1998, 187, 601); kidney disease (Lloyd et al., *J. Exp. Med.* 1997, 185, 1371; and Tesch et al., *J. Clin. Invest.* 1999, 103, 73); lupus erythematosus (Tesch et al., *J. Exp. Med.* 1999, 190, 1813); colitis (Andres et al., *J. Immunol.* 2000, 164, 6303); alveolitis (Jones, et al., *J. Immunol.* 1992, 149, 2147); cancer (Conti, et al., *Seminars in Cancer Biology* 2004, 14, 149; Salcedo et al., *Blood* 2000, 96, 34-40); restinosis (Roque et al. *Arterioscler. Thromb. Vasc. Biol.* 2002, 22, 554-559); inflammatory bowel disease (Reinecker et al., *Gastroenterology* 1995, 108, 40; and Grimm et al., *J. Leukoc. Biol.* 1996, 59, 804); brain trauma (King et al., *J. Neuroimmunol.* 1994, 56, 127; and Berman et al., *J. Immunol.* 1996, 156, 3017); transplant arteriosclerosis (Russell et al., *Proc. Natl. Acad. Sci. USA* 1993, 90, 6086); idiopathic pulmonary fibrosis (Antoniades et al., *Proc. Natl. Acad. Sci. USA* 1992, 89, 5371); psoriasis (Deleuran et al., *J. Dennatol. Sci.* 1996, 13, 228; and Gillitzer et al., *J. Invest. Dernatol.* 1993, 101, 127); HIV and HIV-1-associated dementia (Garzino-Demo, WO 99/46991; Doranz et al., *Cell* 1996, 85, 1149; Connor et al., *J. Exp. Med.* 1997, 185, 621; and Smith et al., *Science* 1997, 277, 959); and neuropathic pain (Abbadie, et al., *Proc. Natl. Acad. Sci. USA* 2003, 100, 7947). Similarly, demonstration of the importance of the MCP-1/CCR-2 interaction has been reported in the literature. For example, Lu et al., *J. Exp. Med.* 1998, 187, 601; Boring et al., *J. Clin. Invest.* 1997, 100, 2552; Kuziel et al., *Proc. Natl. Acad. Sci. USA* 1997, 94, 12053; and Kurihara et al., *J. Exp. Med.* 1997, 186, 1757.

Accordingly, agents that inhibit the interaction of MCP-1 and CCR2 would be useful in the treatment of a variety of inflammatory, allergic and autoimmune diseases, disorders, or conditions.

DETAILED DESCRIPTION OF THE INVENTION

1. General Description of Compounds of the Invention:

The present invention provides compounds that are effective inhibitors of CCR2. Accordingly, these compounds are useful for the treatment of various cell inflammatory, allergic and autoimmune diseases, disorders, or conditions.

The present invention relates to a compound of formula I:

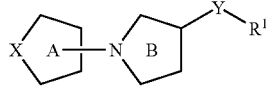

I or a pharmaceutically acceptable salt thereof, wherein:

Y is —$Y_1$-$Y_2$—, wherein:

$Y_1$ is —$SO_2N(R')$—, —C(O)N(R')—; —C(O)N(R')C(O)—, —N(R')$SO_2$—, —N(R')$SO_2$N(R')—, —N(R')C(O)—, —NR'C(O)N(R')—, or —N(R')C(O)O—; and $Y_2$ is absent or is an optionally substituted $C_{1-6}$ alkylene chain, wherein one or two methylene units of $Y_2$ are optionally and independently interrupted by —O—, —S—, —N(R')—, —C(O)—, —OC(O)—, —C(O)O—, —S(O)—, —S(O)$_2$—, —C(O)N(R')—, —N(R')C(O)—, —N(R')C(O)N(R')—, —N(R')C(O)O—, —OC(O)N(R')—, —N(R')S(O)$_2$—, or —S(O)$_2$N(R')—, or wherein $Y_2$, or a portion thereof, is an optionally substituted ring selected from 3-6-membered cycloaliphatic, 3-6-membered heterocyclyl having 1-3 heteroatoms independently selected from nitrogen, oxygen, or sulfur, 6-membered aryl, or 5-6-membered heteroaryl having 1-3 heteroatoms independently selected from nitrogen, oxygen, or sulfur;

each R' is independently hydrogen or optionally substituted $C_{1-6}$ aliphatic;

$R^1$ is an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

ring A is substituted at one or more carbon atoms with m independent occurrences of $R^2$;

m is 0-6;

each occurrence of $R^2$ is independently halogen, =O, =S, —CN, —$R^{2b}$, $N(R^{2a})_2$, $OR^{2a}$, $SR^{2b}$, —$S(O)_2R^{2b}$, —C(O)$R^{2a}$, C(O)O$R^{2a}$, C(O)N($R^{2a}$)$_2$, —S(O)$_2$N($R^{2a}$)$_2$, —OC(O)N($R^{2a}$)$_2$, —N(R')C(O)$R^{2a}$, —N(R')SO$_2R^{2b}$, —N(R')C(O)O$R^{2a}$, —N(R')C(O)N($R^{2a}$)$_2$, or —N(R')SO$_2$N($R^{2a}$)$_2$, or two occurrences of $R^{2a}$ or $R^{2b}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{2a}$, taken together with the nitrogen atom to which they are bound, form an optionally substituted 3-7-membered heterocyclyl ring having 1-3 additional heteroatoms selected from nitrogen, oxygen, or sulfur;

each occurrence of $R^{2a}$ is independently hydrogen or an optionally substituted group selected from $C_{1-6}$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{2b}$ is independently an optionally substituted group selected from $C_{1-6}$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

ring B is substituted with r independent occurrences of —$R^3$;

r is 0-6;

each occurrence of $R^3$ is independently —$R^{3a}$, -$T_1$-$R^{3d}$, or —$V_1$-$T_1$-$R^{3d}$, wherein:

each occurrence of —$R^{3a}$ is independently halogen, —CN, —$NO_2$, —$R^{3c}$, —N($R^{3b}$)$_2$, —$OR^{3b}$, —$SR^{3c}$, —$S(O)_2R^{3c}$, —C(O)$R^{3b}$, —C(O)O$R^{3b}$, —C(O)N($R^{3b}$)$_2$, —S(O)$_2$ N($R^{3b}$)$_2$, —OC(O)N($R^{3b}$)$_2$, —N(R')C(O)$R^{3b}$, —N(R')SO$_2R^{3c}$, —N(R')C(O)O$R^{3b}$, —N(R')C(O)N($R^{3b}$)$_2$, or —N(R')SO$_2$N($R^{3b}$)$_2$, or two occurrences of $R^{3b}$ or $R^{3c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{3b}$, taken together with the nitrogen atom to which they are bound, form an optionally substituted 3-7-membered heterocyclyl ring having 1-3 additional heteroatoms selected from nitrogen, oxygen, or sulfur;

each occurrence of $R^{3b}$ is independently hydrogen or an optionally substituted group selected from $C_{1-6}$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3c}$ is independently an optionally substituted group selected from $C_{1-6}$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_1$ is independently —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—;

each occurrence of $T_1$ is independently $C_{1-6}$ alkylene chain optionally substituted with $R^{3a}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein T$^1$ or a portion thereof optionally forms part of an optionally substituted 3-7 membered cycloaliphatic or heterocyclyl ring;

X is —O—, —S—, —SO$_2$—, or —N(W—R$^4$)—;

W is absent or is a group selected from —W$_1$-L$_2$-W$_2$—, wherein W$_1$ and W$_2$ are each independently absent or are an optionally substituted C$_{1-3}$alkylene chain, and L$_2$ is absent or is a group selected from —N(R)—, —O—, —S—, —S(O)—, —S(O)$_2$—, —C(O)—, —C(O)O—, —C(O)N(R)—, —S(O)$_2$N(R)—, —OC(O)N(R)—, —N(R)C(O)—, —N(R)SO$_2$—, —N(R)C(O)O—, —N(R)C(O)N(R)—, —N(R)SO$_2$N(R)—, —OC(O)—, or —C(O)N(R)—O—, wherein R is hydrogen or C$_1$-C$_4$alkyl, provided that if W$_1$ is absent then L$_2$ is selected from —C(O)—, —C(O)O—, —C(O)O—, —S(O)—, —S(O)$_2$—, —C(O)N(R)—, or —S(O)$_2$N(R)—

R$^4$ is an optionally substituted monocyclic or bicyclic ring selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In some embodiments, a compound of the invention is other than one or more of:

a) 1-Pyrrolidinecarboxamide, 3-[6-(4-chlorophenyl)-4-oxothieno[3,2-d]pyrimidin-3(4H)-yl]-N-methyl-N-[(3S)-1-(tetrahydro-2-oxo-3-furanyl)-3-pyrrolidinyl]-, (3S)—;

b) Pentitol, 1,4-anhydro-2,3,5-trideoxy-3-[(3R)-3-[methyl[[(3S)-3-[methyl[[(4-phenoxyphenyl)amino]carbonyl]amino]-1-pyrrolidinyl]carbonyl]amino]-1-pyrrolidinyl]-;

c) 1-Pyrrolidinecarboxamide, N-methyl-3-[methyl[[4'-(trifluoromethyl)[1,1'-biphenyl]-4-yl]carbonyl]amino]-N-[(3R)-1'-(phenylmethyl)[1,3'-bipyrrolidin]-3-yl]-, (3S)—;

d) Pentitol, 1,4-anhydro-2,3,5-trideoxy-3-[(3R)-3-[methyl[[(3S)-3-[methyl[[4'-(trifluoromethyl)[1,1'-biphenyl]-4-yl]carbonyl]amino]-1-pyrrolidinyl]carbonyl]amino]-1-pyrrolidinyl]-;

e) [1,3'-Bipyrrolidine]-1'-carboxylic acid, 3-[(hydroxyamino)carbonyl]-4-[[4-[(2-methyl-4-quinolinyl)methoxy]benzoyl]amino]-, 1,1-dimethylethyl ester, (3R,4R)-rel-; and f) [1,3'-Bipyrrolidine]-3-carboxamide, N-hydroxy-4-[[4-[(2-methyl-4-quinolinyl)methoxy]benzoyl]amino]-, (3R,4R)-rel-.

2. Compounds and Definitions:

Compounds of this invention include those described generally above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound. By way of example, in a compound of formula (I), if Ring B is substituted with two substituents —R$^b$, each substituent is selected from the group of defined values for R$^b$, and the two values selected may be the same or different.

The term "aliphatic" or "aliphatic group", as used herein, means an optionally substituted straight-chain or branched C$_{1-12}$ hydrocarbon, or a cyclic C$_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)). The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include $-C(R^+)=C(R^+)-$, $-C\equiv C-$, $-O-$, $-S-$, $-S(O)-$, $-S(O)_2-$, $-S(O)_2N(R^+)-$, —N(R⁺)—, —N(R⁺)CO—, —N(R⁺)C(O)N(R⁺)—, —N(R⁺)C(=NR⁺)—N(R⁺)—, —N(R⁺)—C(=NR⁺)—, —N(R⁺)CO₂—, —N(R⁺)SO₂—, —N(R⁺)SO₂N(R⁺)—, —OC(O)—, —OC(O)O—, —OC(O)N(R⁺)—, —C(O)—, —CO₂—, —C(O)N(R⁺)—, —C(O)—C(O)—, —C(=NR⁺)—N(R⁺)—, —C(NR⁺)=N—, —C(=NR⁺)—O—, —C(OR⁺)=N—, —C(R°)=N—O—, or —N(R⁺)—N(R⁺)—. Each R⁺, independently, is hydrogen or an optionally substituted aliphatic, aryl, heteroaryl, cycloaliphatic, or heterocyclyl group, or two independent occurrences of R⁺ are taken together with their intervening atom(s) to form an optionally substituted 5-7-membered aryl, heteroaryl, cycloaliphatic, or heterocyclyl ring. Each R° is an optionally substituted aliphatic, aryl, heteroaryl, cycloaliphatic, or heterocyclyl group.

Examples of $C_{3-6}$ alkylene chains that have been "interrupted" with —O— include —CH₂OCH₂—, —CH₂O(CH₂)₂—, —CH₂O(CH₂)₃—, —CH₂O (CH₂)₄—, —(CH₂)₂CH₂—, —(CH₂)₂O(CH₂)₂—, —(CH₂)₂O(CH₂)₃—, —(CH₂)₃O(CH₂)—, —(CH₂)₃O(CH₂)₂—, and —(CH₂)₄O(CH₂)—. Other examples of alkylene chains that are "interrupted" with functional groups include —CH₂ZCH₂—, —CH₂Z(CH₂)₂—, —CH₂Z(CH₂)₃—, —CH₂Z(CH₂)₄—, —(CH₂)₂ZCH₂—, —(CH₂)₂Z(CH₂)₂—, —(CH₂)₂Z(CH₂)₃—, —(CH₂)₃Z(CH₂)₂—, and —(CH₂)₄ Z(CH₂)—, wherein Z is one of the "interrupting" functional groups listed above. One of ordinary skill in the art will recognize that when an alkylene chain having an interruption is attached to a functional group, certain combinations are not sufficiently stable for pharmaceutical use. Only stable or chemically feasible compounds are within the scope of the present invention.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO₂, —CN, —R⁺, —C(R⁺)=C(R⁺)₂, —C≡C—R⁺, —OR⁺, —SR°, —S(O)R°, —SO₂R°, —SO₃R⁺, —SO₂N(R⁺)₂, —N(R⁺)₂, —NR⁺C(O)R⁺, —NR⁺C(S)R⁺, —NR⁺C(O)N(R⁺)₂, —NR⁺C(S)N(R⁺)₂, —N(R⁺)C(=NR⁺)—N(R⁺)₂, —N(R⁺)C(=NR⁺)—R°, —NR⁺CO₂R⁺, —NR⁺SO₂R°, —NR⁺SO₂N(R⁺)₂, —O—C(O)R⁺, —O—CO₂R⁺, —OC(O)N(R⁺)₂, —C(O)R⁺, —C(S)R°, —CO₂R⁺, —C(O)—C(O)R⁺, —C(O)N(R⁺)₂, —C(S)N(R⁺)₂, —C(O)N(R⁺)—OR⁺, —C(O)N(R⁺)C(=NR⁺)—N(R⁺)₂, —N(R⁺)C(=NR⁺)—N(R⁺)—C(O)R⁺, —C(=NR⁺)—N(R⁺)₂, —C(=NR⁺)—OR⁺, —N(R⁺)—N(R⁺)₂, —C(=NR⁺)—N(R⁺)—OR⁺, —C(R°)=N—OR⁺, —P(O)(R⁺)₂, —P(O)(OR⁺)₂, —O—P(O)—OR⁺, and —P(O)(NR⁺)—N(R⁺)₂, wherein R° and R⁺ are as defined above.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)₂, =N—N(R*)₂, =N—OR*, =N—NHC(O)R*, =N—NHCO₂R°, =N—NHSO₂R° or =N—R* where each R* and R° is defined above.

In addition to the substituents defined above and herein, optional substituents on the nitrogen of a non-aromatic heterocyclic ring also include and are generally selected from —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R⁺)₂, —C(S)N(R⁺)₂, —C(=NH)—N(R⁺)₂, or —N(R⁺)S(O)₂R⁺; wherein each R⁺ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R⁺ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R⁺ (or any other variable similarly defined in the specification and claims herein), are taken together with their intervening atom(s) include, but are not limited to the following: a) two independent occurrences of R⁺ (or any other variable similarly defined in the specification or claims herein) that are bound to the same atom and are taken together with that atom to form a ring, for example, N(R⁺)₂, where both occurrences of R⁺ are taken together with the nitrogen atom to form a piperidin-1-yl, piperazin-1-yl, or morpholin-4-yl group; and b) two independent occurrences of R⁺ (or any other variable similarly defined in the specification or claims herein) that are bound to different atoms and are taken together with both of those atoms to form a ring, for example where a phenyl group is substituted with two occurrences of OR⁺

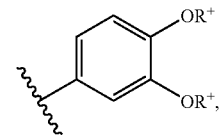

these two occurrences of R⁺ are taken together with the oxygen atoms to which they are bound to form a fused 6-membered oxygen containing ring:

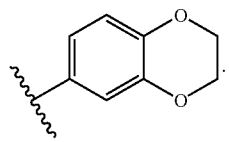

It will be appreciated that a variety of other rings (e.g., spiro and bridged rings) can be formed when two independent occurrences of R⁺ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95% 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

In certain exemplary embodiments n is 1 and the compound has the structure of formula I-A-I or I-A-ii:

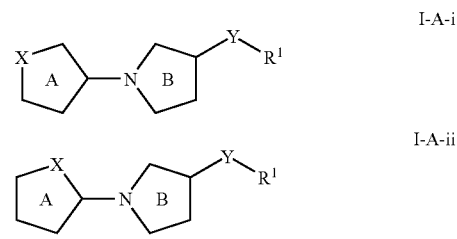

In certain embodiments r is 0 or 1. In other embodiments, r is 1 and the compound has the structure of formula I-B:

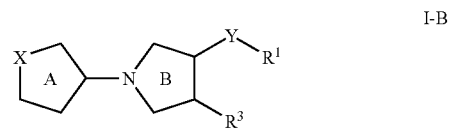

In yet other embodiments, r is 2 and the compound has the structure of I-B-i:

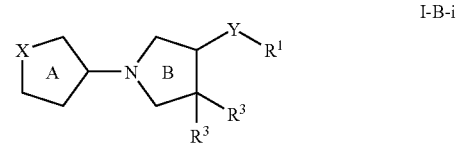

wherein the two occurrences of $R^3$, taken together, form an optionally substituted 3-6-membered spiro carbocyclic or heterocyclic ring.

In certain embodiments, $R^1$ is an optionally substituted aryl group. In other embodiments, $R^1$ is an optionally substituted phenyl group. In still other embodiments, $R^1$ is an optionally substituted 5-8-membered monocyclic or 7-10-membered bicyclic heterocyclyl or heteroaryl ring having 1-4 heteroatoms independently selected from N, O, or S. In yet other embodiments, $R^1$ is an optionally substituted group selected from:

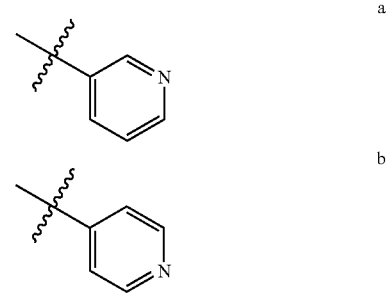

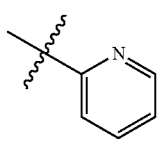
c
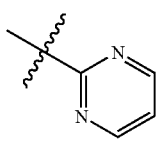
d
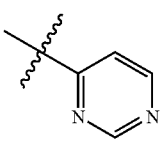
e
In still other embodiments, R¹ is an optionally substituted group selected from:
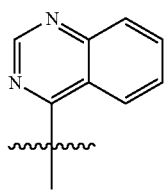
f
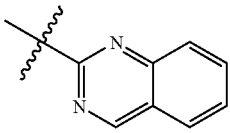
g
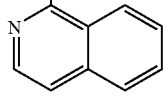
h
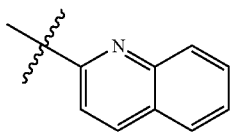
i
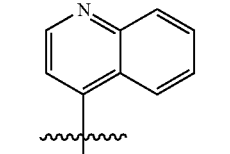
j
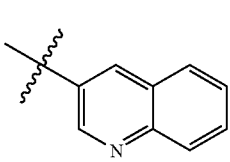
k
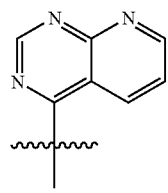
l
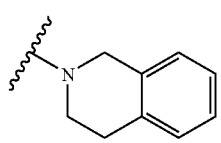
m
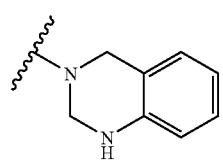
n
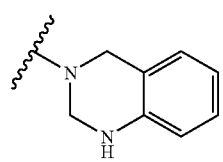
o
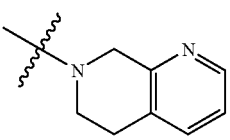
p
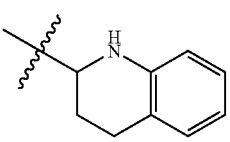
q
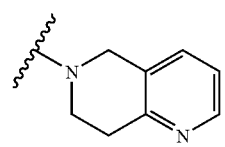
r
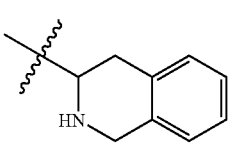
s
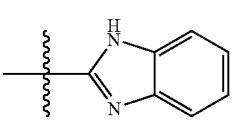
t
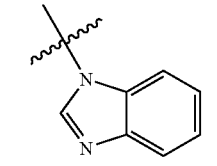
u -continued

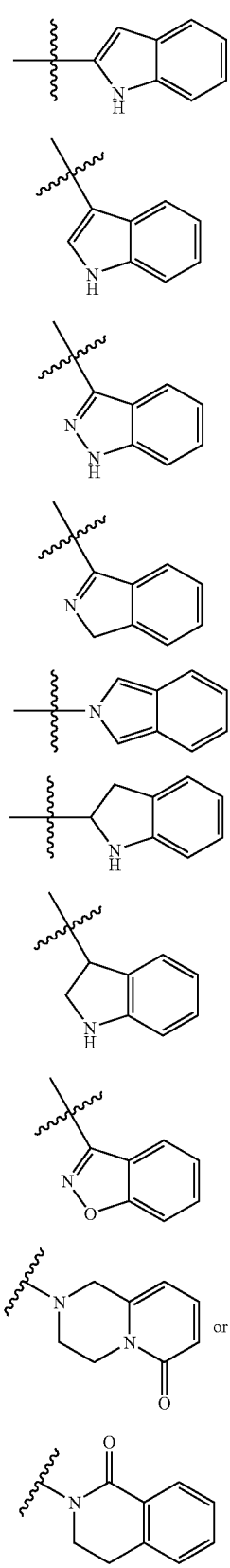

v w x y z aa bb cc dd ee

In some embodiments, $R^1$ is optionally substituted with 1-3 occurrences of $R^{1a}$, wherein each occurrence of $R^{1a}$ is independently halogen, =O, =S, —CN, —NO$_2$, —$R^{1c}$, —N($R^{1b}$)$_2$, —O$R^{1b}$, —S$R^{1c}$, —S(O)$_2$$R^{1c}$, —C(O)$R^{1b}$, —C(O)O$R^{1b}$, —C(O)N($R^{1b}$)$_2$, —S(O)$_2$N($R^{1b}$)$_2$, —OC(O)N($R^{1b}$)$_2$, —N(R')C(O)$R^{1b}$, —N(R')SO$_2$$R^{1c}$, —N(R')C(O)O$R^{1b}$, —N(R')C(O)N($R^{1b}$)$_2$, or —N(R')SO$_2$N($R^{1b}$)$_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In some embodiments, each occurrence of $R^{1a}$ is independently =O, halogen, —$R^{1c}$, —N($R^{1b}$)$_2$, —O$R^{1b}$, or —S$R^{1c}$. In other embodiments, each occurrence of $R^{1a}$ is independently $C_{1-4}$-fluoroalkyl, —O($C_{1-4}$fluoroalkyl), or —S($C_{1-4}$fluoroalkyl).

In still other embodiments, $Y_1$ is —SO$_2$N(R')—, —C(O)NR'—, or —N(R')S(O)$_2$—.

In yet other embodiments, $Y_1$ is —N(R')C(O)—. In still other embodiments, Y is selected from:

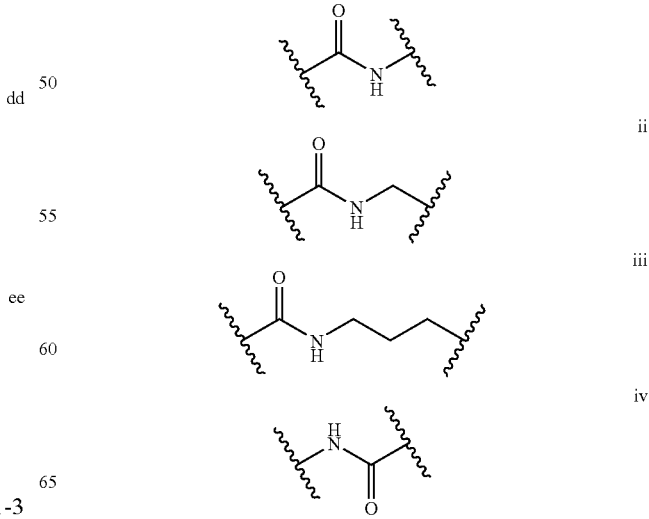

i ii iii iv

-continued

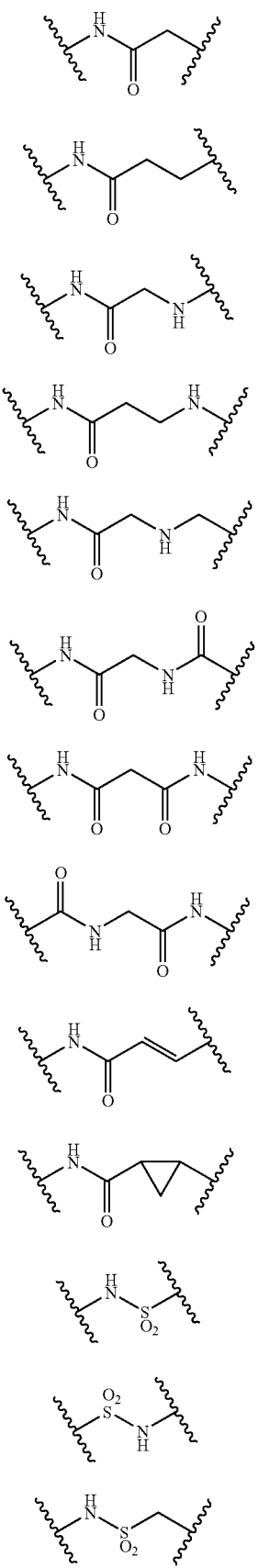

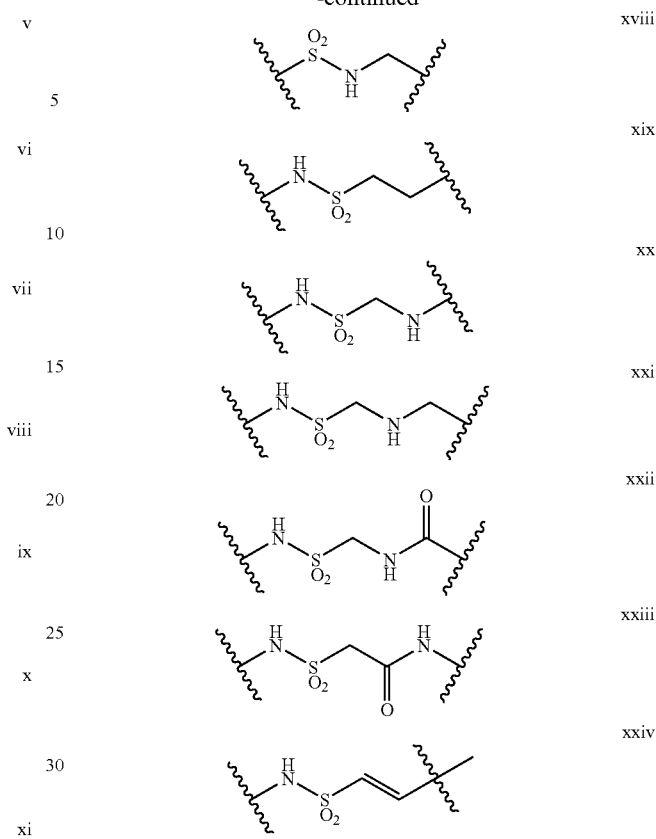

In other embodiments, for compounds of the invention X is O. In still other embodiments, X is —N(W—R$^4$).

In still other embodiments, for compounds of the invention, X is O, m is 1, and R$^2$ is an optionally substituted group selected from a monocyclic 3-8-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur.

In yet other embodiments, for compounds of the invention, X is —N(W—R$^4$) and R$^4$ is an optionally substituted group selected from a monocyclic 3-8-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur.

In yet other embodiments, R$^4$ is optionally substituted with 1-3 occurrences of R$^{4a}$ and each occurrence of R$^{4a}$ is independently —R$^{4b}$, -T$_1$-R$^{4c}$, or —V$_1$-T$_1$-R$^{4c}$, wherein:

each occurrence of —R$^{4b}$ is independently halogen, —CN, —NO$_2$, —R$^{4d}$, —N(R)$_2$, OR$^{4c}$, SR$^{4d}$, —S(O)$_2$R$^{4d}$, —C(O)R$^{4c}$, —C(O)OR$^{4c}$, —C(O)N(R$^{4c}$)$_2$, —S(O)$_2$N(R$^{4c}$)$_2$, —OC(O)N(R$^{4c}$)$_2$, —N(R')C(O)R$^{4c}$, —N(R')SO$_2$R$^{4d}$, —N(R')C(O)OR$^{4c}$, —N(R')C(O)N(R$^{4c}$)$_2$, or —N(R')SO$_2$N(R$^{4c}$)$_2$, or two occurences of R$^{4b}$, R$^{4c}$ or $R^{4d}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{4c}$, taken together with the nitrogen atom to which they are bound, form an optionally substituted 3-7-membered heterocyclyl ring having 1-3 additional heteroatoms selected from nitrogen, oxygen, or sulfur;

each occurrence of $R^{4c}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_1$ is independently —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—;

each occurrence of $T_1$ is independently $C_{1-6}$ alkylene chain optionally substituted with $R^{3a}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein $T^1$ or a portion thereof optionally forms part of an optionally substituted 3-7 membered cycloaliphatic or heterocyclyl ring;

In still other embodiments, X is —N(W—R$^4$), W is absent and R$^4$ is optionally substituted phenyl, wherein the phenyl group is substituted with 1 or 2 occurrences of $R^{4a}$, wherein each occurrence of $R^{4a}$ is independently halogen, —CN, —C(O)N(R$^{4c}$)$_2$, —O(R$^{4c}$), —S(R$^{4d}$), —N(R$^{4c}$)$_2$, —C(O)O-$T_1$-R$^{4c}$, —R$^{4d}$, or wherein two occurrences of R$^{4b}$, taken together with their intervening atoms, form a 5-6-membered spiro or fused carbocyclic or heterocyclyl ring.

In yet other embodiments, for compounds of the invention, R$^3$ is —OR$^{3b}$, —SR$^{3c}$, —V$_1$-T$_1$-R$^{3d}$, or T$_1$-R$^{3d}$, wherein V$_1$ is O or S, and T$_1$ is —CH$_2$— or —CH$_2$—CH$_2$—.

In some embodiments, R$^{3b}$, R$^{3c}$, and R$^{3d}$ are each independently an optionally substituted group selected from $C_{1-4}$alkenyl, $C_{1-4}$alkynyl, $C_{1-4}$alkyl, 5-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In other embodiments, R$^{3b}$, R$^{3c}$, and R$^{3d}$ are each independently optionally substituted $C_{1-4}$alkenyl, $C_{1-4}$alkynyl, $C_{1-4}$alkyl, or an optionally substituted group selected from:

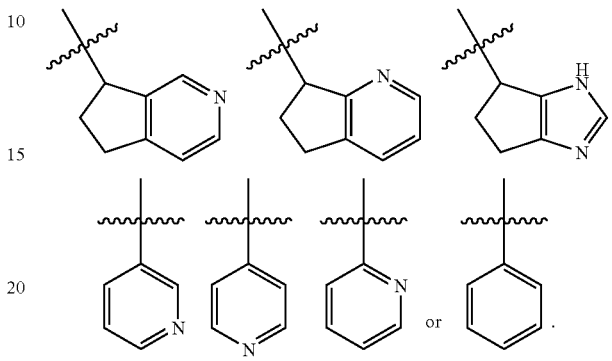

In still other embodiments, R$^{3b}$, R$^{3c}$, and R$^{3d}$ are each independently an optionally substituted ring selected from bicyclic 8-10-membered heterocyclyl having 1-5 heteroatoms independently selected from nitrogen, oxygen, or sulfur or 8-10-membered heteroaryl having 1-5 heteroatoms independently selected from nitrogen, oxygen, or sulfur.

In yet other embodiments, R$^{3b}$, R$^{3c}$, and R$^{3d}$ are each independently optionally substituted with 1-3 occurrences of R$^3$, wherein R$^{3e}$ is R$^f$, halogen, —N(R$^g$)$_2$, —OR$^g$, —SR$^f$, —S(O)$_2$ R$^f$, —COR$^f$, —COOR$^g$, —CON(R$^g$)$_2$, —CON(R$^g$)$_2$, —S(O)$_2$N(R$^g$)$_2$, —CC(O)N(R$^g$)$_2$, —NR'C(O) R$^f$, —NR'S(O)$_2$ R$^f$, wherein R$^f$ is an optionally substituted $C_{1-6}$ aliphatic group and R$^g$ is hydrogen or an optionally substituted $C_{1-6}$ aliphatic group.

In still other embodiments, R$^{3b}$, R$^{3c}$, and R$^{3d}$ are each independently optionally substituted with 1-3 occurrences of R$^{3e}$, wherein R$^{3e}$ is $C_{1-4}$aliphatic, $C_{1-4}$haloaliphatic, or halogen.

In still other embodiments, r is 2 and two occurrences of R$^3$, taken together, form an optionally substituted 3-6-membered spiro carbocyclic or heterocyclic ring. In some embodiments, the spiro ring is an optionally substituted ring selected from:

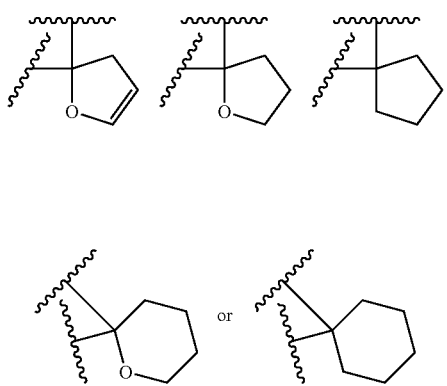

Certain additional subsets of interest include those compounds having the structure of formula I-C:

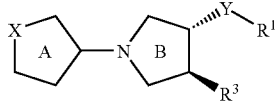

I-C or a pharmaceutically acceptable salt thereof.

In some embodiments, for compounds of general formula I-C, X is O and the compound has the structure of formula I-D:

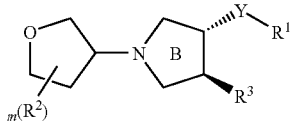

I-D or a pharmaceutically acceptable salt thereof, wherein:

a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, =O, =S, —CN, —$NO_2$, —$R^{1c}$, —$N(R^{1b})_2$, —$OR^{1b}$, —$SR^{1c}$, —$S(O)_2R^{1c}$, —$C(O)R^{1b}$, —$C(O)OR^{1b}$, —$C(O)N(R^{1b})_2$—$S(O)_2N(R^{1b})_2$, —$OC(O)N(R^{1b})_2$, —N(R')C(O)$R^{1b}$, —N(R')$SO_2R^{1c}$, —N(R')C(O)$OR^{1b}$, —N(R')C(O)N($R^{1b})_2$, or —N(R')$SO_2N(R^{1b})_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

b) Y is —NH(CO)$CH_2$—, —NHS(O)$_2CH_2$, —NHC(O)—, —NH(CO)$CH_2$NH—, or —NHS(O)$_2$—;

c) m is 0 or 1, and when m is 1 $R^2$ is an optionally substituted group selected from a monocyclic 3-7-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur; and d) $R^3$ is —$OR^{3b}$, —$SR^{3c}$, —$V_1$-$T_1$-$R^{3d}$, or $T_1$-$R^{3d}$, wherein $V_1$ is O or S, and $T_1$ is —$CH_2$— or —$CH_2$—$CH_2$—, wherein $R^{3b}$, $R^{3c}$, and $R^{3d}$ are each independently an optionally substituted group selected from $C_{1-4}$alkenyl, $C_{1-4}$alkynyl, $C_{1-4}$alkyl, 5-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In other embodiments, for compounds of general formula I-D:

a) $R^1$ is an optionally substituted group selected from:

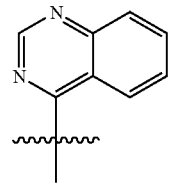

f

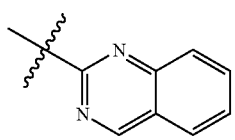

g

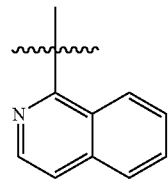

h

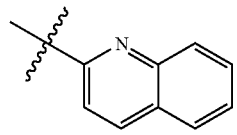

i

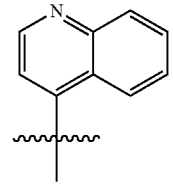

j

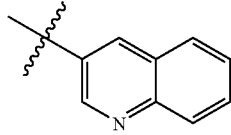

k

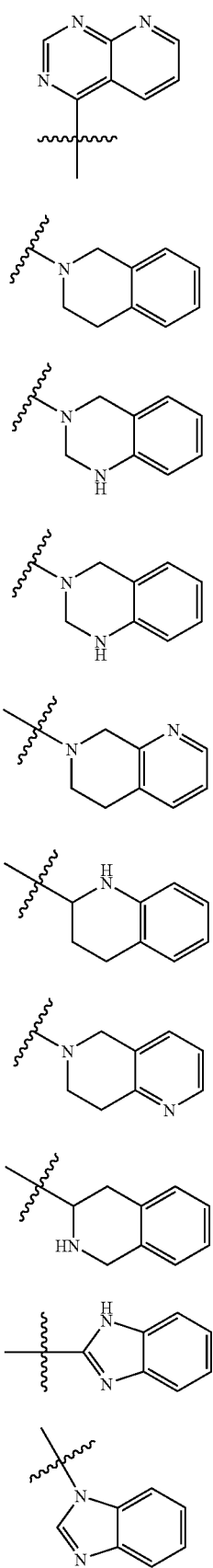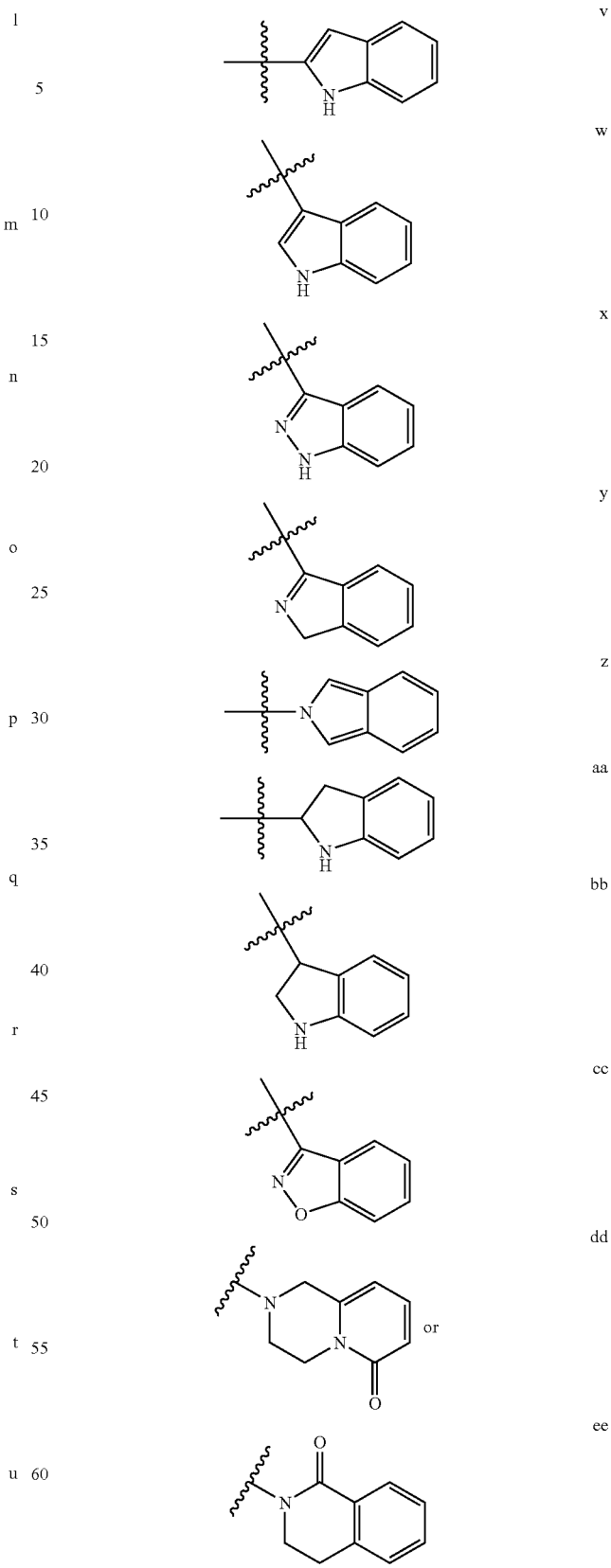
and each occurrence of $R^{1a}$ is independently =O, halogen, —$R^{1c}$, —$N(R^{1b})_2$, —$OR^{1b}$, or —$SR^{1c}$; and b) $R^{3b}$, $R^{3c}$, and $R^{3d}$ are each independently optionally substituted $C_{1-4}$alkenyl, $C_{1-4}$alkynyl, $C_{1-4}$alkyl, or an optionally substituted group selected from:

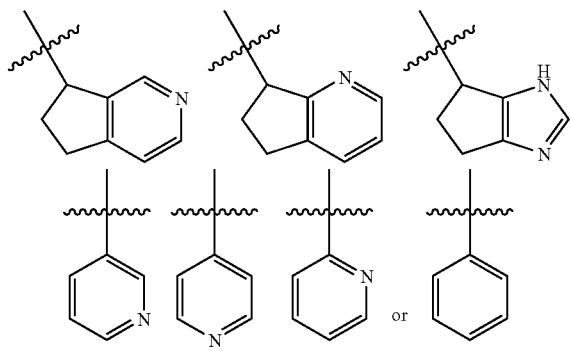

wherein $R^{3b}$, $R^{3c}$, and $R^{3d}$ are each independently optionally substituted with 1-3 occurrences of $R^{3e}$, wherein $R^3_e$ is $C_{1-4}$aliphatic, $C_{1-4}$haloaliphatic, or halogen.

In some embodiments, for compounds of general formula I-C, X is N(W—$R^4$), and the compound has the structure of formula I-E:

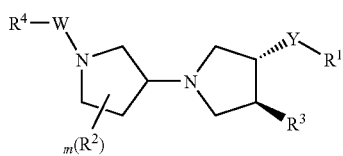

I-E or a pharmaceutically acceptable salt thereof, wherein:

a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, =O, —CN, —NO$_2$, —$R^{1c}$, —N($R^{1b}$)$_2$, —O$R^{1b}$, —S$R^{1c}$, —S(O)$_2R^{1c}$, —C(O)$R^{1b}$, —C(O)O$R^{1b}$, —C(O)N($R^{1b}$)$_2$, —S(O)$_2$N($R^{1b}$)$_2$, —OC(O)N($R^{1b}$)$_2$, —N(R')C(O)$R^{1b}$, —N(R')SO$_2R^{1c}$, —N(R')C(O)O$R^{1b}$, —N(R')C(O)N($R^{1b}$)$_2$, or —N(R')SO$_2$N($R^{1b}$)$_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

b) Y is —NH(CO)CH$_2$—, —NHS(O)$_2$CH$_2$—, —NHC(O)—, —NH(CO)CH$_2$NH—, or —NHS(O)$_2$—;

c) m is 0;

d) $R^3$ is —O$R^{3b}$, —S$R^{3c}$, —V$_1$-T$_1$-$R^{3d}$, or T$_1$-$R^{3d}$, wherein V$_1$ is O or S, and T$_1$ is —CH$_2$— or —CH$_2$—CH$_2$—, wherein $R^{3b}$, $R^{3c}$, and $R^{3d}$ are each independently an optionally substituted group selected from $C_{1-4}$alkenyl, $C_{1-4}$alkynyl, $C_{1-4}$alkyl, 5-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

e) W is absent, and f) $R^4$ is an optionally substituted group selected from a monocyclic 3-7-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur.

In some embodiments, for compounds of general formula I-C, X is N(W—$R^4$), and the compound has the structure of formula I-E:

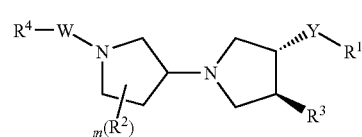

I-E or a pharmaceutically acceptable salt thereof, wherein:

a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, =O, —CN, —NO$_2$, —$R^{1c}$, —N($R^{1b}$)$_2$, —O$R^{1b}$, —S$R^{1c}$, —S(O)$_2R^{1c}$, —C(O)$R^{1b}$, —C(O)O$R^{1b}$, C(O)N($R^{1b}$)$_2$, —S(O)$_2$N($R^{1b}$)$_2$, —OC(O)N($R^{1b}$)$_2$, —N(R')C(O)$R^{1b}$, —N(R')SO$_2R^{1c}$, —N(R')C(O)O$R^{1b}$, —N(R')C(O)N($R^{1b}$)$_2$, or —N(R')SO$_2$N($R^{1b}$)$_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

b) Y is —NH(CO)CH$_2$—, —NHS(O)$_2$CH$_2$, —NHC(O)—, —NH(CO)CH$_2$NH—, or —NHS(O)$_2$—;

c) m is 0;

d) $R^3$ is —OR$^{3b}$, —SR$^{3c}$, —V$_1$-T$_1$-R$^{3d}$, or T$_1$-R$^{3d}$, wherein V$_1$ is O or S, and T$_1$ is —CH$_2$— or —CH$_2$—CH$_2$—, wherein $R^{3b}$, $R^{3c}$, and $R^{3d}$ are each independently an optionally substituted group selected from C$_{1-4}$alkenyl, C$_{1-4}$alkynyl, C$_{1-4}$alkyl, 5-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

e) W is absent, and f) $R^4$ is optionally substituted phenyl.

In other embodiments, for compounds of general formula I-E, $R^4$ is optionally substituted with 1-3 occurrences of $R^{4a}$ and each occurrence of $R^{4a}$ is independently —R$^{4b}$, -T$_1$-R$^{1e}$, or —V$_1$-T$_1$-R$^{1e}$, wherein:

each occurrence of —R$^{4b}$ is independently halogen, —CN, —NO$_2$, R$^{4d}$, —N(R$^{4c}$)$_2$, —OR$^{4c}$, —SR$^{4d}$, —S(O)$_2$R$^{4d}$, —C(O)R$^{4c}$, —C(O)OR$^{4c}$, —C(O)N(R$^{4c}$)$_2$, —S(O)$_2$N(R$^{4c}$)$_2$, —OC(O)N(R$^{4c}$)$_2$, —N(R')C(O)R$^{4c}$, —N(R')SO$_2$R$^{4d}$, —N(R')C(O)OR$^{4c}$, —N(R')C(O)N(R$^{4c}$)$_2$, or —N(R')SO$_2$N(R$^{4c}$)$_2$, or two occurences of R$^{4b}$, R$^{4e}$ or R$^{4d}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of R$^{4c}$, taken together with the nitrogen atom to which they are bound, form an optionally substituted 3-7-membered heterocyclyl ring having 1-3 additional heteroatoms selected from nitrogen, oxygen, or sulfur;

each occurrence of R$^{4c}$ is independently hydrogen or an optionally substituted group selected from C$_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{4d}$ is independently an optionally substituted group selected from C$_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{4e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of V$_1$ is independently —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—; and each occurrence of T$_1$ is independently C$_{1-6}$ alkylene chain optionally substituted with R$^{3a}$, wherein the alkylene chain optionally is interrupted by —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein T$^1$ or a portion thereof optionally forms part of an optionally substituted 3-7 membered cycloaliphatic or heterocyclyl ring.

In other embodiments, for compounds of general formula I-E:

a) $R^1$ is an optionally substituted group selected from:

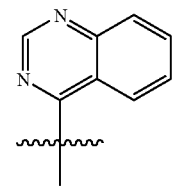

f

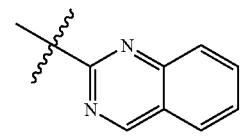

g

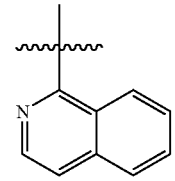

h

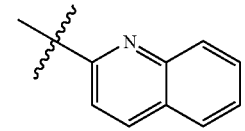

i

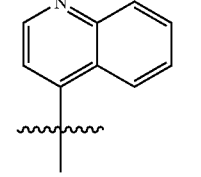

j

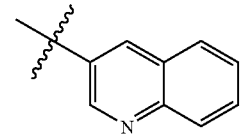

k

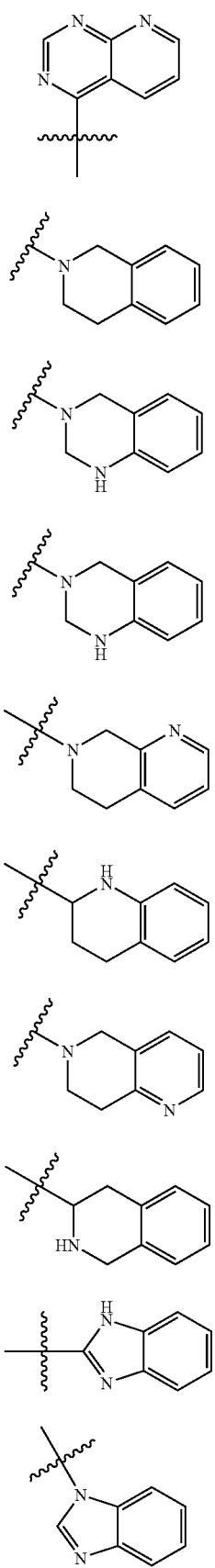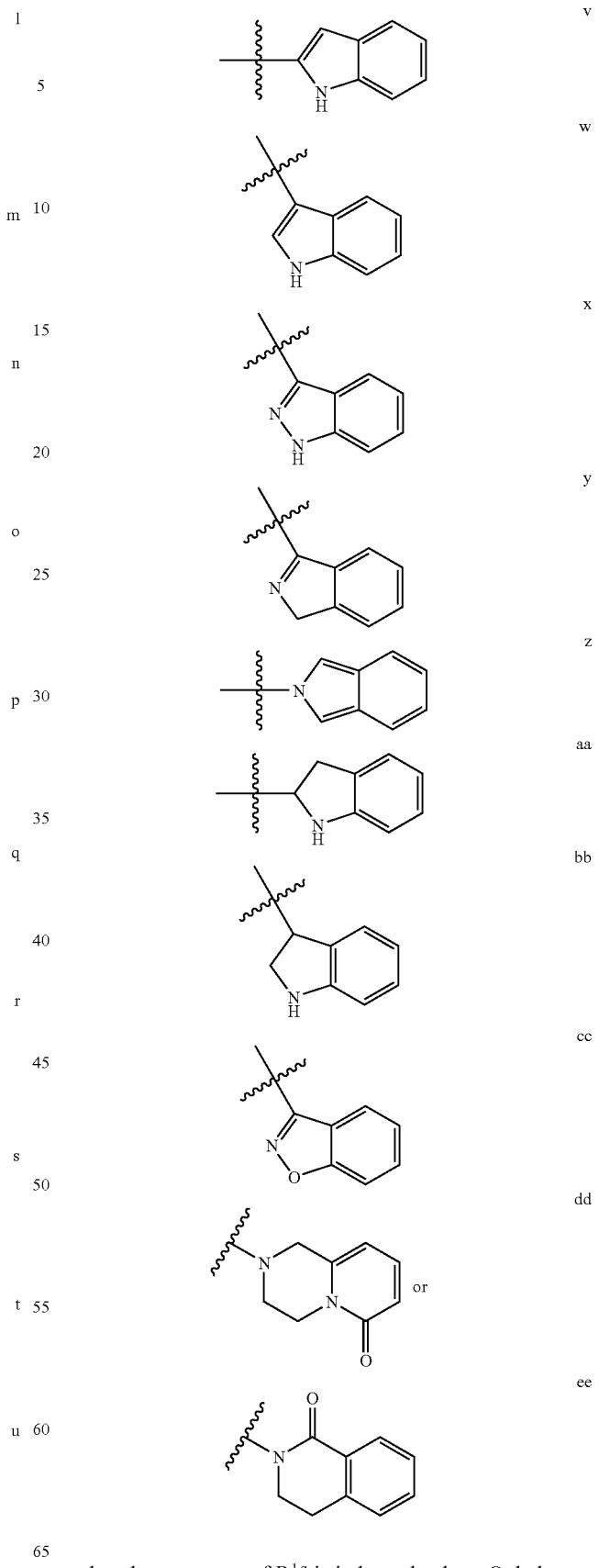
and each occurrence of $R^{1a}$ is independently =O, halogen, —$R^{1c}$, —$N(R^{1b})_2$, —$OR^{1b}$, or —$SR^{1c}$; and b) $R^{3b}$, $R^{3c}$, and $R^{3d}$ are each independently optionally substituted $C_{1-4}$alkenyl, $C_{1-4}$alkynyl, $C_{1-4}$alkyl, or an optionally substituted group selected from:

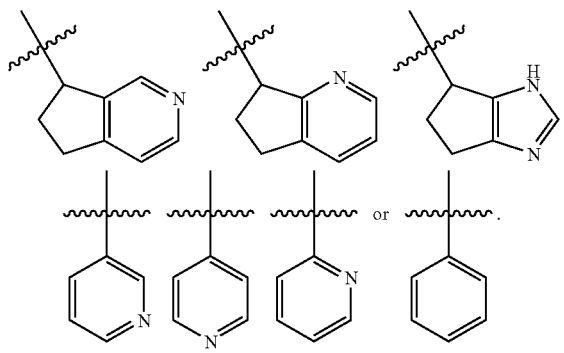

wherein $R^{3b}$, $R^{3c}$, and $R^{3d}$ are each independently optionally substituted with 1-3 occurrences of $R^{3e}$, wherein $R^{3e}$ is $C_{1-4}$aliphatic, $C_{1-4}$haloaliphatic, or halogen.

Still other subsets of interest include those compounds having the structure of formula I-F:

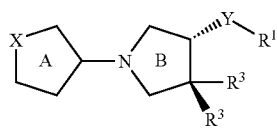

I-F or a pharmaceutically acceptable salt thereof,
wherein the two occurrences of $R^3$, taken together, form an optionally substituted 3-6-membered spiro carbocyclic or heterocyclic ring.

In some embodiments, for compounds of general formula I-F, X is O and the compound has the structure of formula I-G:

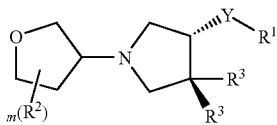

I-G or a pharmaceutically acceptable salt thereof, wherein:

a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, =O, =S, —CN, —NO$_2$, —R$^{1c}$, —N(R$^{1b}$)$_2$, —OR$^{1b}$, —SR$^{1c}$, —S(O)$_2$R$^{1c}$, —C(O)R$^{1b}$, —C(O)OR$^{1b}$, —C(O)N(R$^{1b}$)$_2$, —S(O)$_2$N(R$^{1b}$)$_2$, —OC(O)N(R$^{1b}$)$_2$, —N(R')C(O)R$^{1b}$, —N(R')SO$_2$R$^{1c}$, —N(R')C(O)OR$^{1b}$, —N(R')C(O)N(R$^{1b}$)$_2$, or —N(R')SO$_2$N(R$^{1b}$)$_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

b) Y is —NH(CO)CH$_2$—, —NHS(O)$_2$CH$_2$, —NHC(O)—, —NH(CO)CH$_2$NH—, or —NHS(O)$_2$—;

c) m is 0 or 1, and when m is 1 $R^2$ is an optionally substituted group selected from a monocyclic 3-7-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur; and d) wherein the two occurrences of $R^3$, taken together, form an optionally substituted 3-6-membered spiro carbocyclic or heterocyclic ring.

In other embodiments, for compounds of general formula I-G:

a) $R^1$ is an optionally substituted group selected from:

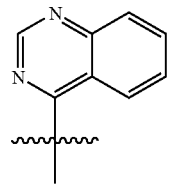
f

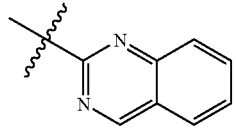
g

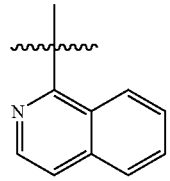
h

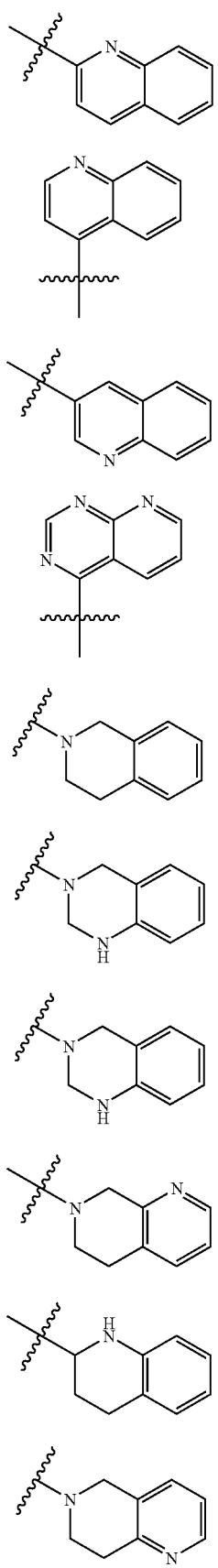
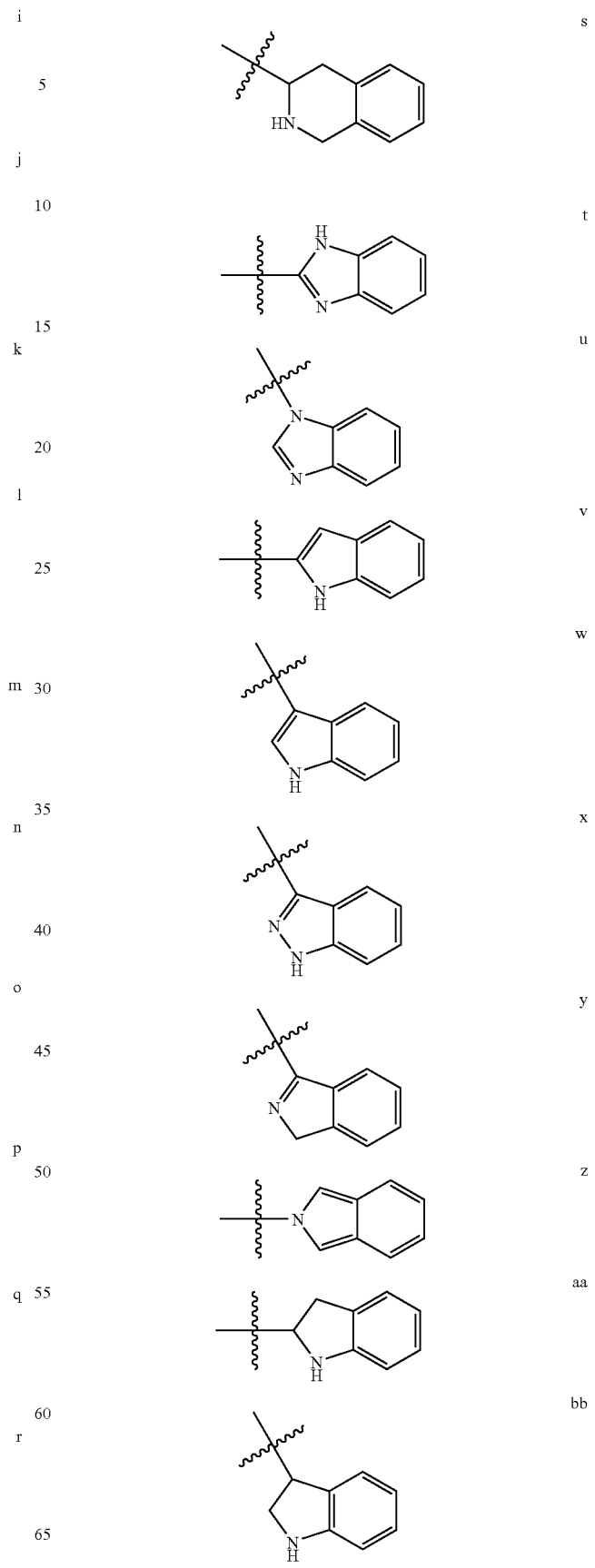

-continued

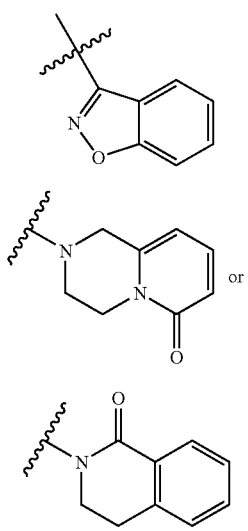

and each occurrence of $R^{1a}$ is independently =O, halogen, —$R^{1c}$, —$N(R^{1b})_2$, —$OR^{1b}$, or —$SR^{1c}$; and
b) the Spiro ring formed from the two occurrences of $R^3$ is an optionally substituted ring selected from:

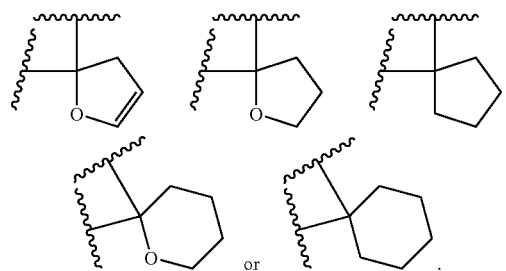

In some embodiments, for compounds of general formula I-F, X is N(W—$R^4$), and the compound has the structure of formula I-H:

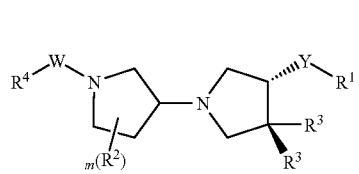

I-H or a pharmaceutically acceptable salt thereof, wherein:
a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, =O, —CN, —$NO_2$, —$R^{1c}$, —$N(R^{1b})_2$, —$OR^{1b}$, —$SR^{1c}$, —$S(O)_2R^{1c}$, —$C(O)R^{1b}$, —$C(O)OR^{1b}$, $C(O)N(R^{1b})_2$, —$S(O)_2N(R^{1b})_2$, —$OC(O)N(R^{1b})_2$, —N(R')C(O)$R^{1b}$, —N(R')$SO_2R^{1c}$, —N(R')C(O)$OR^{1b}$, —N(R')C(O)N($R^{1b}$)$_2$, or —N(R')$SO_2N(R^{1b})_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:
  each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and
  each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
b) Y is —NH(CO)$CH_2$—, —NHS(O)$_2CH_2$—, —NHC(O)—, —NH(CO)$CH_2$NH—, or —NHS(O)$_2$—;
c) m is 0;
d) wherein the two occurrences of $R^3$, taken together, form an optionally substituted 3-6-membered spiro carbocyclic or heterocyclic ring;
e) W is absent, and
f) $R^4$ is an optionally substituted group selected from a monocyclic 3-7-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur.

In some embodiments, for compounds of general formula I-F, X is N(W—$R^4$), and the compound has the structure of formula I-H:

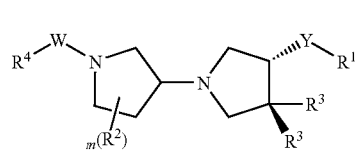

I-H or a pharmaceutically acceptable salt thereof, wherein:
a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, =O, —CN, —$NO_2$, —$R^{1c}$, —$N(R^{1b})_2$, —$OR^{1b}$, —$SR^{1c}$, S(O)$_2R^{1c}$, —C(O)$R^{1b}$, —C(O)O$R^{1b}$, —C(O)N($R^{1b}$)$_2$, —S(O)$_2$N($R^{1b}$)$_2$, —OC(O)N($R^{1b}$)$_2$, —N(R')C(O)$R^{1b}$, —N(R')SO$_2R^{1c}$, —N(R')C(O)O$R^{1b}$, —N(R')C(O)N($R^{1b}$)$_2$, or —N(R')SO$_2$N($R^{1b}$)$_2$, or two occurences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

b) Y is —NH(CO)CH$_2$—, —NHS(O)$_2$CH$_2$, —NHC(O)—, —NH(CO)CH$_2$NH—, or —NHS(O)$_2$—;

c) m is 0;

d) the spiro ring formed from the two occurrences of $R^3$ is an optionally substituted ring selected from:

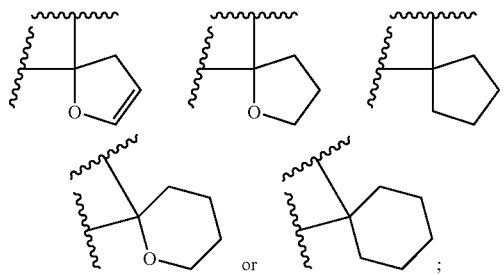

e) W is absent, and f) $R^4$ is optionally substituted phenyl.

In other embodiments, for compounds of general formula I-H, $R^4$ is optionally substituted with 1-3 occurrences of $R^{4a}$ and each occurrence of $R^{4a}$ is independently —$R^{4b}$, -$T_1$-$R^{4e}$, or —$V_1$-$T_1$-$R^{4e}$, wherein:

each occurrence of —$R^{4b}$ is independently halogen, —CN, —NO$_2$, —$R^{4d}$, —N($R^{4c}$)$_2$, —OR$^{4c}$, —SR$^{4d}$, —S(O)$_2$R$^{4d}$, —C(O)R$^{4c}$, —C(O)OR$^{4c}$, —C(O)N($R^{4c}$)$_2$, —S(O)$_2$ N($R^{4c}$)$_2$, —OC(O)N($R^{4c}$)$_2$, —N(R')C(O)R$^{4c}$, —N(R')SO$_2$R$^{4d}$, —N(R')C(O)OR$^e$, —N(R')C(O)N (R$^{4c}$)$_2$, or —N(R')SO$_2$N($R^{4c}$)$_2$, or two occurences of $R^{4b}$, $R^{4c}$ or $R^{4d}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{4c}$, taken together with the nitrogen atom to which they are bound, form an optionally substituted 3-7-membered heterocyclyl ring having 1-3 additional heteroatoms selected from nitrogen, oxygen, or sulfur;

each occurrence of $R^{4c}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_1$ is independently —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—; and each occurrence of $T_1$ is independently $C_{1-6}$ alkylene chain optionally substituted with $R^{3a}$, wherein the alkylene chain optionally is interrupted by —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein $T^1$ or a portion thereof optionally forms part of an optionally substituted 3-7 membered cycloaliphatic or heterocyclyl ring.

In other embodiments, for compounds of general formula I-H:

a) $R^1$ is an optionally substituted group selected from:

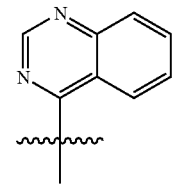

f

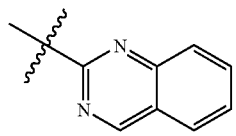

g

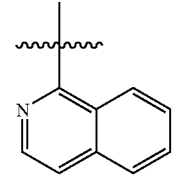

h

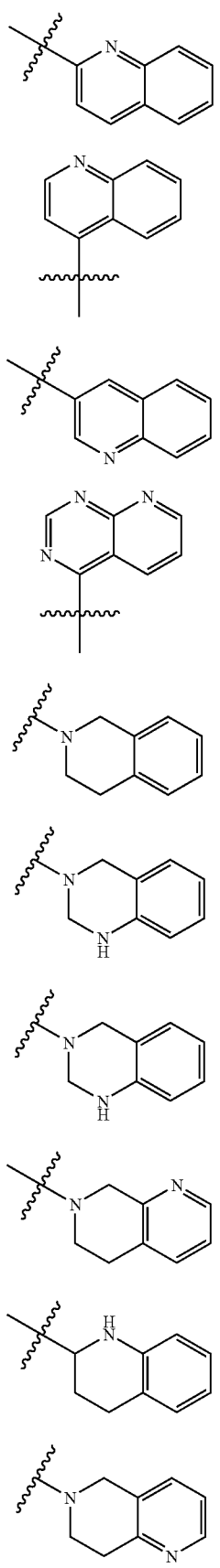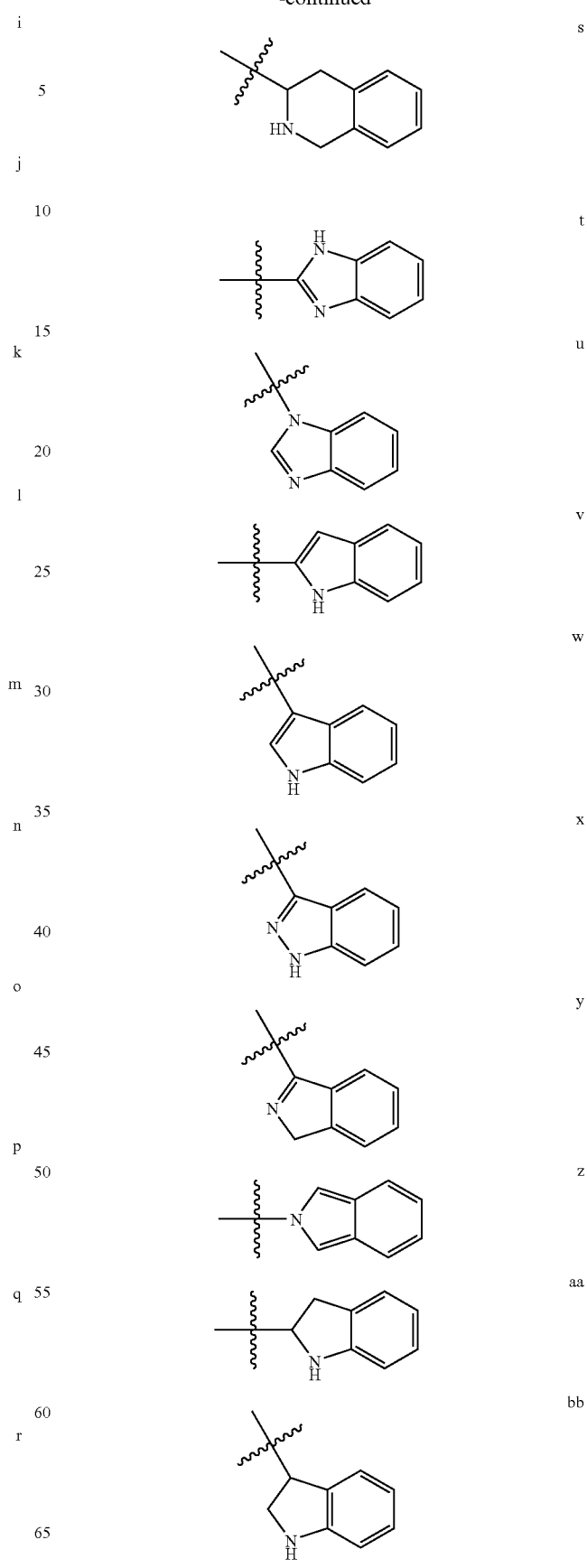

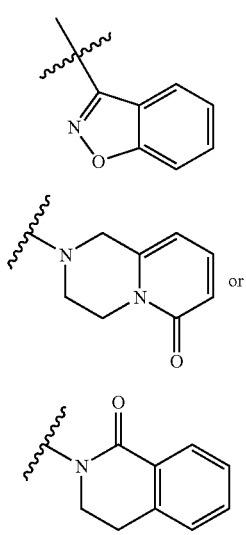

and each occurrence of $R^{1a}$ is independently —O, halogen, —$R^{1c}$, —$N(R^{1b})_2$, —$OR^{1b}$, or —$SR^{1c}$; and b) the spiro ring formed from the two occurrences of $R^3$ is an optionally substituted ring selected from:

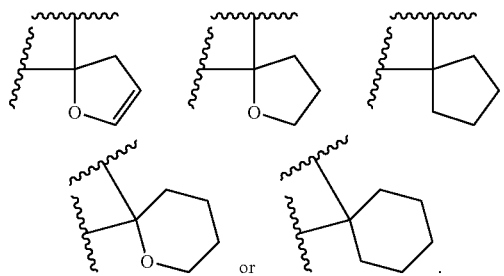

4. Uses, Formulation, and Administration:

As discussed above, the present invention provides compounds that are inhibitors of chemokine receptor activity. In some embodiments, the present invention provides compounds that are inhibitors of CCR2 activity. The compounds can be assayed in vitro or in vivo for their ability to bind to and/or inhibit chemokine receptor activity, preferably CCR2. Assays are described in the Examples and/or are known in the art.

In another aspect, therefore, the invention provides a method for inhibiting CCR2 activity in biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Inhibition of CCR2 activity in a biological sample is useful for a variety of purposes that are known to one of skill in the art. Examples of such purposes include, but are not limited to, blood transfusion, organ-transplantation, biological specimen storage, and biological assays.

In some embodiments, the compound of formula I interacts with and reduces the activity of more than one chemokine receptor in the biological sample, preferably a cell. By way of example, when assayed against CCR2, some compounds of formula I show inhibition of more than one chemokine receptor, for example CCR5. In some embodiments, the compound of formula I is selective for the inhibition of CCR2, i.e., the concentration of the compound that is required for inhibition of CCR2 is lower, preferably at least 2-fold, 5-fold, 10-fold, or 50-fold lower, than the concentration of the compound required for inhibition of another chemokine receptor (e.g., CCR5). In some embodiments of the invention, compounds of the invention are selective for the inhibition of CCR2. As used herein, the term "selective" means that a compound binds to or inhibits a chemokine receptor with greater affinity or potency, respectively, compared to at least one other chemokine receptor, or preferably compared to all other chemokine receptors of the same class (e.g., all of the CC-type receptors). In some embodiments, the compounds of the invention have binding or inhibition selectivity for CCR2 or CCR5 over any other chemokine receptor. Selectivity can be at least about 10-fold, at least about 20-fold, at least about 50-fold, at least about 100-fold, at least about 200-fold, at least about 500-fold, or at least about 1000-fold. Binding affinity and inhibitor potency can be measured according to routine methods in the art, such as according to the assays provided herein.

As used herein the term "contacting" refers to the bringing together of indicated moieties in an in vitro or an in vivo system. For example, "contacting" the chemokine receptor with a compound of the invention includes the administration of a compound of the present invention to a subject, such as a human, having a chemokine receptor, as well as, for example, introducing a compound of the invention into a sample containing a cellular or purified preparation containing the chemokine receptor.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt of a compound of this invention that, upon administration to a recipient, is capable of providing, either directly or indirectly, a compound of this invention or an active metabolite or residue thereof. As used herein, the term "active metabolite or residue thereof" means that a metabolite or residue thereof is useful for the treatment of inflammatory or allergic disorders. In some embodiments, without wishing to be bound by any particular theory, a "pharmaceutically acceptable salt" means any non-toxic salt of a compound of this invention that, upon administration to a recipient, is capable of providing, either directly or indirectly, an inhibitorily active compound of the invention or an inhibitorily active metabolite or residue thereof. As used herein, the term "inhibitorily active compound or inhibitorily active metabolite or residue thereof" means that a compound or metabolite or residue thereof is also an inhibitor of CCR2.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, formate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Mack Publishing Co., a standard reference text in this field, discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a desired site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds of this invention or pharmaceutical compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

The pharmaceutical compositions of the invention preferably are formulated for administration to a patient having, or at risk of developing or experiencing a recurrence of, an inflammatory, allergic or autoimmune disease, condition, or disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

As discussed above, compounds of the invention (including salts thereof) are useful as inhibitors of CCR2 activity. Several diseases and disorders have been shown to be mediated at least in part by the activation of CCR2. Thus, compounds of the invention are useful for the treatment of (therapeutically or prophylactically) conditions mediated by CCR2, including, but not limited to, inflammatory, allergic, or autoimmune diseases, conditions, or disorders. The disclosed compounds can also be advantageously used for the treatment of diseases, conditions, or disorders mediated by esinophils, monocytes, T lymphocytes and other immune system cells which express CCR2, including inflammatory, allergic, or autoimmune diseases, conditions, or disorders mediated by these cells. When activation of CCR2 is implicated in a particular disease, condition, or disorder, the disease, condition, or disorder may also be referred to as "a CCR2-mediated disease, condition, or disorder" or disorder symptom. Accordingly, in another aspect, the present invention provides a method for the treatment of an inflammatory, allergic, or autoimmune disease, condition, or disorder is provided comprising administering an effective amount of a compound or a pharmaceutical composition to a subject in need thereof.

Examples of allergic conditions for which the disclosed compounds, pharmaceutical compositions and methods are particularly effective include asthma, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis and urticaria.

Examples of diseases with an inflammatory component for which the disclosed compounds, pharmaceutical composition and methods are effective include rheumatoid arthritis, osteoarthritis, inflammatory bowel disease [e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis] and disorders of the skin [e.g., psoriasis, erythema, pruritis, and acne].

Many autoimmune diseases also have an inflammatory component. Examples include multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease). The inflammatory component of these disorders is believed to be mediated, at least in part, by CCR2.

Diseases characterized by repurfusion have an inflammatory component that is believed to be mediated, at least in part by CCR2. Examples include stroke, cardiac ischemia, and the like. The disclosed compounds and pharmaceutical compositions also can be used to treat these disorders.

Other diseases and conditions with an inflammatory component believed to be mediated by CCR2 include mastitis (mammary gland), vaginitis, cholecystitis, cholangitis or pericholangitis (bile duct and surrounding tissue of the liver), chronic bronchitis, chronic sinusitis, chronic inflanunatory diseases of the lung which result in interstitial fibrosis, such as interstitial lung diseases (ILD) (e.g., idiopathic pulmonary fibrosis, or ILD associated with rheumatoid arthritis, or other autoimmune conditions), cystic fibrosis, hypersensitivity pneumonitis, collagen diseases, neuropathic pain, and sarcoidosis.

Yet other diseases or conditions with inflammatory components which are amenable to treatment according to methods disclosed herein include vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

Still other diseases or conditions which are amenable to treatment according to methods disclosed herein include cancer, preferably breast cancer or multiple myeloma.

In some embodiments, the present invention provides a method for treating rheumatoid arthritis, multiple sclerosis, scleroderma, atherosclerosis, neuropathic pain, type II diabetes, COPD (chronic obstructive pulmonary disorder), cystic fibrosis, hepatic fibrosis, inflammatory bowel disease, lung fibrosis, lupus, lupus nephritis, macular degeneration, cancer (including breast cancer and multiple myeloma), acute and chronic organ transplant rejection, inflammatory pain, post MI remodeling, psoriasis, renal fibrosis, restenosis, stroke, uveitis, endometriosis, acute pancreatitis, peripheral vascular disease, sarcoidosis, or CIDP/Guillain-Barre disease comprising administering a therapeutically effective amount of a compound of formula I.

In still other embodiments, the present invention provides a method for treating rheumatoid arthritis, multiple sclerosis, scleroderma, atherosclerosis, neuropathic pain, or type II diabetes comprising administering a therapeutically effective amount of a compound of formula I.

In yet other embodiments, the present invention provides a method for treating rheumatoid arthritis or multiple sclerosis comprising administering a therapeutically effective amount of a compound of formula I.

As used herein, "treatment" or "treating" means partial alleviation, prevention, or cure of a disease, condition, or disorder as described herein.

As used herein a "therapeutically effective amount" of the compound or pharmaceutical composition is that quantity required to achieve a desired therapeutic and/or prophylactic effect, such as an amount which results in the prevention of or a decrease in the symptoms associated with a disease, condition or disorder as described herein. In some embodiments, a therapeutically effective amount of a compound is that amount which results in the inhibition of one or more of the processes mediated by the binding of a chemokine to a receptor such as CCR2 in a subject with a disease associated with aberrant leukocyte recruitment and/or activation. Typical examples of such processes include leukocyte migration, integrin activation, transient increases in the concentration of intracellular free calcium and granule release of proinflammatory mediators.

Compounds and pharmaceutical compositions, according to the method of the present invention, may be administered using any amount and any route of administration effective for treating a disease, condition, or disorder as described herein. The skilled artisan will be able to determine appropriate dosages depending on these and other factors. An "effective amount" typically ranges between about 0.01 mg/kg/day to about 100 mg/kg/day, preferably between about 0.5 mg/kg/day to about 50 mg/kg/day. In other embodiments, an effective amount typically ranges between about 1 mg/kg/day to about 25 mg/kg/day.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The term "subject", as used herein, is preferably a bird or mammal, such as a human (*Homo sapiens*), but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated". Exemplary additional therapeutic agents for use with an antagonist of chemokine receptor function include, but are not limited to theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1α, IFNβ-1β)) and the like.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXAMPLES

Although certain exemplary embodiments are depicted and described herein, it will be appreciated that compounds of the invention can be prepared using appropriate starting materials according to the methods described generally herein and/or by methods generally available to one of ordinary skill in the art. Additional embodiments are exemplified in more detail herein. Exemplary compounds of formula I are depicted in Table 1 below and described in the examples below.

General. All reactions involving air-sensitive reagents were performed under a nitrogen atmosphere. Reagents were used as received from commercial suppliers unless otherwise noted. $^1$H NMR data were recorded using the Bruker UltraShield 300 MHz/54 mm instrument equipped with Bruker B-ACS60 Auto Sampler or the Varian 300 MHz instrument. Intermediates and final compounds were purified by flash chromatography using one of the following instruments: 1. Biotage 4-channel Quad UV Flash Collector equipped with a Quad 1 Pump Module and the Quad 12/25 Cartridge module. 2. Biotage 12-channel Quad UV Flash Collector equipped with a Quad 3 Pump Module and a Quad 3 Cartridge module. 3. ISCO combi-flash chromatography instrument. LC/MS spectra were obtained using a MicroMass Platform LC (Phenomenx C18 column, 5 micron, 50×4.6 mm) equipped with a Gilson 215 Liquid Handler. Standard LC/MS conditions are as follows. LC-MS data were acquired using the "Ammonium acetate-standard" method unless otherwise noted.

Ammonium Acetate-Standard Conditions:

| % A (Water) | 95.0 |
| % B (Acetonitrile) | 5.0 |
| % Ammonium acetate | 0.1 |
| Flow (ml/min) | 2.500 |
| Stop Time (mins) | 3.8 |
| Min Pressure (bar) | 0 |
| Max Pressure (bar) | 400 |
| Oven Temperature Left (° C.) | 10.0 |
| Oven Temperature Right (° C.) | 10.0 |

HP1100 LC Pump Gradient Timetable
The gradient Timetable contains 4 entries which are:

| Time | A % | B % | C % | D % | Flow | Pressure |
|---|---|---|---|---|---|---|
| 0.00 | 95.0 | 5.0 | 0.0 | 0.0 | 2.500 | 400 |
| 2.00 | 0.0 | 100.0 | 0.0 | 0.0 | 2.500 | 400 |
| 3.00 | 0.0 | 100.0 | 0.0 | 0.0 | 2.500 | 400 |
| 3.05 | 95.0 | 5.0 | 0.0 | 0.0 | 2.000 | 400 |

Benzyl (3R)-3-[({[3-(trifluoromethyl)benzoyl] amino}acetyl)amino]-1,3'-bipyrrolidine-1'-carboxylate (1)

To a solution of N-{2-oxo-2-[(3R)-pyrrolidin-3-ylamino] ethyl}-3-(trifluoromethyl)benzamide (500 mg, 1.59 mmol; prepared according to WO2004/050024A2) in methanol (5 mL) at room temperature was added benzyl 3-oxopyrrolidine-1-carboxylate (434 mg, 1.98 mmol) followed by sodium triacetoxyborohydride (470 mg, 2.22 mmol); the reaction mixture was stirred for 16 hours. To the mixture was added NaHCO$_3$ (sat. aq., 10 mL) and dichloromethane (10 mL). The organic layer was separated and the aqueous layer was washed with an addition portion of dichloromethane (10 mL). The organic layers were combined, dried over Na$_2$SO$_4$, filtered and concentrated. The resulting crude product was subjected to flash chromatography (15% MeOH, 1% NH$_4$OH in EtOAc) to afford, as a mixture of diastereomers, benzyl (3R)-3-[({[3-(trifluoromethyl)benzoyl]amino}acetyl)amino]-1, 3'-bipyrrolidine-1'-carboxylate (906 mg, 88%) as a white solid. $^1$H-NMR (CDCl$_3$) δ: 1.30-1.44 (m, 2H), 1.50-1.68 (m, 2H), 1.80-2.00 (m, 2H), 2.10-3.29 (m, 1H), 2.30-2.43 (m, 1H), 2.55-23.05 (m, 3H), 3.15-3.28 (m, 1H), 3.58-4.20 (m, 3H), 4.30-4.50 (m, 1H), 5.09 (s, 2H), 6.70-6.87 (m, 1H), 7.20-7.50 (m, 6H), 7.52 (t, J=8.7 Hz, 1H), 7.72 (d, J=7.2 Hz, 1H), 7.99 (d, J=7.2 Hz, 1H), 8.09 (s, 1H). MS m/z: 519 (M+1)

N-(2-{[(3R)-1'-(4-methoxyphenyl)-5'-oxo-1,3'-bipyrrolidin-3-yl]amino}-2-oxoethyl)-3-(trifluoromethyl) benzamide (2)

To a solution of N-allyl-4-methoxyaniline (1.00 g, 6.13 mmol) in methylene chloride (20 mL) was added K$_2$CO$_3$ (2.12 mg, 15.3 mmol) and acryloyl chloride (548 µL, 6.74 mmol) at 0° C. After 15 min., the reaction was quenched with NaHCO$_3$ (5 mL, sat. aq.) and the organic layer was isolated, concentrated and subjected to flash chromatography (Hexanes:EtOAc 4:1) to yield N-allyl-N-(4-methoxyphenyl)acrylamide (1.29 mg, 97%).

To a solution of N-allyl-N-(4-methoxyphenyl)acrylamide (150 mg, 0.69 mmol) in degassed methylene chloride (400 mL) was added Grubbs catalyst (58 mg, 0.069 mmol) and the mixture was heated to 40° C. overnight. All volatiles were removed and the resulting material was subjected to flash chromatography (Hexanes:EtOAc 1:1) to yield 1-(4-methoxyphenyl)-1,5-dihydro-2H-pyrrol-2-one (110 mg, 86%).

A slurry of water (20 µL, 0.10 mmol), 1-(4-methoxyphenyl)-1,5-dihydro-2H-pyrrol-2-one (200 mg, 1.06 mmol) and N-{2-oxo-2-[(3R)-pyrrolidin-3-ylamino]ethyl}-3-(trifluoromethyl)benzamide (666 mg, 2.12 mmol) was heated to 90° C. overnight. The crude mixture was subjected to flash chromatography (1% NH$_4$OH, 15% MeOH, EtOAc) to afford, as a mixture of diastereomers, N-(2-{[(3R)-1'-(4-methoxyphenyl)-5'-oxo-1,3'-bipyrrolidin-3-yl]amino}-2-oxoethyl)-3-(trifluoromethyl)benzamide as a white solid (115 mg, 21%). $^1$H-NMR (CDCl$_3$) δ: 1.50-1.82 (m, 1H), 1.83-2.00 (m, 1H), 2.18-2.40 (m, 1H), 2.40-2.58 (m, 1H), 2.56-2.81 (m, 3H), 2.83-3.00 (m, 2H), 3.29-3.33 (m, 2H), 3.60-3.71 (m, 2H), 3.79 (s, 3H), 4.04-4.20 (m, 2H), 4.38-4.47 (m, 1H), 6.94 (m, 2H), 7.19-7.30 (m, 2H), 7.69-7.80 (m, 2H), 7.99 (d, J=7.8 Hz, 1H), 8.18 (s, 1H). MS m/z: 505 (M+1).

Benzyl 4-{(3R)-3-[({[3-(trifluoromethyl)benzoyl]amino}acetyl)amino]-1,3'-bipyrrolidin-1'-yl}benzoate (3)

In a round-bottom flask, a slurry of benzyl (3R)-3-[({[3-(trifluoromethyl)benzoyl]amino}acetyl)amino]-1,3'-bipyrrolidine-1'-carboxylate (0.765 g, 1.48 mmol) and Palladium (10%) on Carbon (0.200 g) in methanol (10 mL) was purged with hydrogen gas for 2 min.; the reaction was then subjected to 1 atm of hydrogen gas for 3 h. The flask was purged with Argon, then the mixture was filtered and concentrated to afford N-{2-[(3R)-1,3'-bipyrrolidin-3-ylamino]-2-oxoethyl}-3-(trifluoromethyl)benzamide (0.551 g, 97%) as an off-white solid. $^1$H-NMR (CDCl$_3$) δ: 1.32-1.53 (m, 2H), 1.52-2.04 (m, 6H), 2.15-2.40 (m, 2H), 2.40-2.70 (m, 3H), 2.80-3.00 (m, 3H), 4.00-4.20 (m, 2H), 4.42 (bs, 1H), 6.77 (m, 1H), 7.40-7.55 (m, 1H), 7.53 (t, J=7.8 Hz, 1H), 7.73 (d, J=7.2 Hz, 1H), 7.98 (d, J=7.5 Hz, 1H), 8.08 (s, 1H). MS m/z: 399 (M+1).

To a solution of N-{2-[(3R)-1,3'-bipyrrolidin-3-ylamino]-2-oxoethyl}-3-(trifluoromethyl)benzamide (525 mg, 1.36 mmol) in DMSO (3 mL) was added K$_2$CO$_3$ (940 mg, 6.8 mmol) followed by benzyl 4-fluorobenzoate (786 mg, 3.41 mmol). The mixture was heated to 120° C. for 16 hours. The crude mixture was subjected to column chromatography (15% MeOH, 1% NH$_4$OH in EtOAc) to afford, as a mixture of diastereomers, N-{2-[(3R)-1,3'-bipyrrolidin-3-ylamino]-2-oxoethyl}-3-(trifluoromethyl)benzamide (355 mg, 44%) as a white solid. $^1$H-NMR (MeOD) δ: 1.70-1.80 (m, 1H), 1.92-2.04 (m, 1H), 2.20-2.36 (m, 2H), 2.56-2.70 (m, 2H), 2.84-2.96 (m, 2H), 2.96-3.09 (m, 1H), 3.20-3.42 (m, 4H), 3.46-3.62 (m, 2H), 4.03 (s, 2H), 4.37-4.50 (m, 1H), 5.29 (s, 2H), 6.57 (d, J=9.0 Hz, 2H), 7.27-7.46 (m, 5H), 7.68 (t, J=6.9 Hz, 1H), 7.82-7.90 (m, 3H), 8.14 (d, J=8.1 Hz, 1H), 8.22 (s, 1H). MS m/z: 595 (M+1)

N,N-diethyl-4-{(3R)-3-[({[3-(trifluoromethyl)benzoyl]amino}acetyl)amino]-1,3'-bipyrrolidin-1'-yl}benzamide (4)

In a round-bottom flask, a solution of benzyl 4-{(3R)-3-[({[3-(trifluoromethyl)benzoyl]amino}acetyl)amino]-1,3'-bipyrrolidin-1'-yl}benzoate (258 mg, 0.43 mmol) in methanol (400 μL) and Palladium (10%) on Carbon (50 mg) was purged with hydrogen gas for two minutes; the reaction was then subjected to 1 atmosphere of hydrogen gas for two hours. The flask was purged with Argon, then the mixture was filtered and concentrated to afford 4-{(3R)-3-[({[3-(trifluoromethyl)benzoyl]amino}acetyl)amino]-1,3'-bipyrrolidin-1'-yl}benzoic acid (197 mg, 91%) as an off-white solid.

To a solution of 4-{(3R)-3-[({[3-(trifluoromethyl)benzoyl]amino}acetyl)amino]-1,3'-bipyrrolidin-1'-yl}benzoic acid (35 mg, 0.069 mmol), HATU (0.032 g, 0.086 mmol), N,N-diisopropylethylamine (30.2 μL, 0.173 mmol), 1-Hydroxybenzotriazole (11.7 mg, 0.0867 mmol) in DMF (3.0 mL) was added diethylamine (8.25 μL, 0.079 mmol). The reaction mixture was allowed to stir at room temperature overnight. To the mixture was added NaHCO$_3$ (sat. aq., 10 mL) and dichloromethane (10 mL). The organic layer was separated and the aqueous layer was washed with an addition portion of dichloromethane (10 mL). The organic layers were combined, dried over Na$_2$SO$_4$, filtered and concentrated. The resulting crude product was subjected to flash chromatography (15% MeOH, 1% NH$_4$OH in EtOAc) to afford, as a mixture of diastereomers, N,N-diethyl-4-{(3R)-3-[({[3-(trifluoromethyl)benzoyl]amino}acetyl)amino]-1,3'-bipyrrolidin-1'-yl}benzamide (32 mg, 82%) as a white solid. $^1$H-NMR (MeOD) δ: 1.19 (t, J=6.6 Hz, 6H), 1.66-1.80 (m, 1H), 1.90-2.05 (m, 1H), 2.18-2.40 (m, 2H), 2.50-2.70 (m, 2H), 2.80-3.06 (m, 4H), 3.15-3.40 (m, 4H), 3.38-3.60 (m, 5H), 4.03 (s, 2H), 4.37-4.50 (m, 1H), 6.58 (d, J=8.4 Hz, 2H), 7.26 (d, J=8.1 Hz, 2H), 7.69 (t, J=7.2 Hz, 1H), 7.86 (d, J=7.2 Hz, 1H), 8.14 (d, J=7.5 Hz, 1H), 8.22 (s, 1H). MS m/z: 560 (M+1)

N-[2-({(3R)-1'-[4-(morpholin-4-ylcarbonyl)phenyl]-1,3'-bipyrrolidin-3-yl}amino)-2-oxoethyl]-3-(trifluoromethyl)benzamide (5)

The title compound was synthesized in similar fashion to N,N-diethyl-4-{(3R)-3-[({[3-(trifluoromethyl)benzoyl]amino}acetyl)amino]-1,3'-bipyrrolidin-1'-yl}benzamide, substituting morpholine for diethylamine, and was isolated, as a mixture of diastereomers, as a white solid. $^1$H-NMR (MeOD) δ: 1.55-1.6.5 (m, 1H), 1.67-1.82 (m, 1H), 1.90-2.06 (m, 1H), 2.20-2.36 (m, 2H), 2.56-2.68 (m, 2H), 2.84-2.95 (m, 2H), 2.96-3.06 (m, 1H), 3.18-3.40 (m, 2H), 3.42-3.60 (m, 2H), 3.60-3.74 (m, 10H), 4.03 (s, 2H), 4.39-4.50 (m, 1H), 6.59 (d, J=8.7 Hz, 2H), 7.33 (d, J=8.4 Hz, 2H), 7.69 (t, J=8.1 Hz, 1H), 7.86 (d, J=7.5 Hz, 1H), 8.22 (s, 1H). MS m/z: 574 (M+1)

N-(2-oxo-2-{[(3R)-1-(tetrahydro-3-thienyl)pyrrolidin-3-yl]amino}ethyl)-3-(trifluoromethyl)benzamide (6)

The title compound was synthesized in similar fashion to benzyl (3R)-3-[({[3-(trifluoromethyl)benzoyl]amino}acetyl)amino]-1,3'-bipyrrolidine-1'-carboxylate, whereby dihydrothiophen-3(2H)-one was substituted for benzyl 3-oxopyrrolidine-1-carboxylate, and was isolated, as a mixture of diastereomers, as a white solid. $^1$H-NMR (CDCl$_3$) δ: 1.55-1.66 (m, 1H), 1.71-1.81 (m, 1H), 2.03-2.14 (m, 1H), 2.15-2.26 (m, 1H), 2.33-2.39 (m, 1H), 2.52-2.58 (m, 1H), 2.63-2.73 (m, 3H), 2.74-2.81 (m, 4H), 4.07 (d, J=4.8 Hz, 2H), 4.36-4.38 (m, 1H), 7.04 (d, J=7.8 Hz, 1H), 7.46 (t, J=7.9 Hz, 1H), 7.67 (d, J=7.5 Hz, 1H), 7.81 (t, J=4.9 Hz, 1H), 7.93 (d, J=8.4 Hz, 1H), 8.03 (s, 1H). MS m/z: 402 (M+1)

Methyl 4-{(3R)-3-[({[3-(trifluoromethyl)benzoyl]amino}acetyl)amino]-1,3'-bipyrrolidin-1'-yl}benzoate (7)

A slurry of N-{2-[(3R)-1,3'-bipyrrolidin-3-ylamino]-2-oxoethyl}-3-(trifluoromethyl)benzamide (50 mg, 0.13 mmol), methyl 4-bromobenzoate (35 mg, 0.16 mmol), Pd$_2$(dba)$_3$ (12 mg, 0.013 mmol), cesium carbonate (64 mg, 0.19 mmol) and R-BINAP (8 mg, 0.013 mmol) in toluene was heated at 100° C. overnight. To the mixture was added NaHCO$_3$ (sat. aq., 10 mL) and dichloromethane (10 mL). The organic layer was separated and the aqueous layer was washed with an addition portion of dichloromethane (10 mL). The organic layers were combined, dried over Na$_2$SO$_4$, filtered and concentrated. The resulting crude product was subjected to flash chromatography (15% MeOH, 1% NH$_4$OH in EtOAc) to afford, as a mixture of diastereomers, methyl 4-{(3R)-3-[({[3-(trifluoromethyl)benzoyl]amino}acetyl)amino]-1,3'-bipyrrolidin-1'-yl}benzoate (20 mg, 30%) as a white solid. ¹H-NMR (CDCl₃) δ: 1.60-1.76 (m, 1H), 1.86-2.04 (m, 1H), 2.08-2.25 (m, 1H), 2.20-2.44 (m, 2H), 2.60-2.78 (m, 2H), 2.84-3.00 (m, 2H), 3.18 (q, J=8.7 Hz, 1H), 3.32 (q, J=7.5 Hz, 1H), 3.40-3.54 (m, 2H), 3.82 (s, 3H), 4.10 (m, 2H), 4.40-4.56 (m, 1H), 6.44 (d, J=8.7 Hz, 2H), 6.54 (d, J=2.4 Hz, 1H), 7.20-7.35 (m, 1H), 7.54 (t, J=7.8 Hz, 1H), 7.74 (d, J=8.1 Hz, 1H), 7.87 (d, J=8.4 Hz, 2H), 7.97 (d, J=7.8 Hz, 1H), 8.07 (s, 1H). MS m/z: 519 (M+1)

Compounds 8-143 can also be prepared by the methods described herein. Those skilled in the art will be able to recognize, or be able to ascertain, using no more than routine experimentation, many equivalents to the specific embodiments of the invention described herein.

TABLE 1

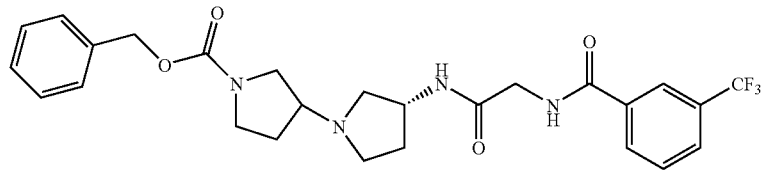

1

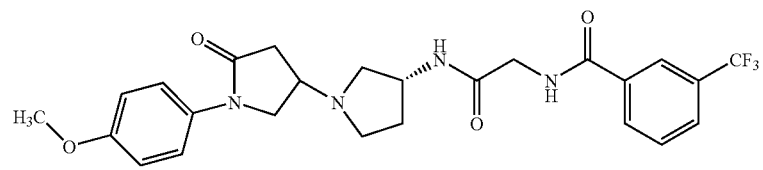

2

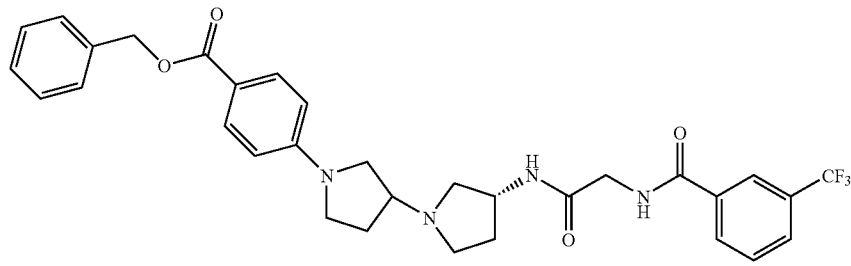

3

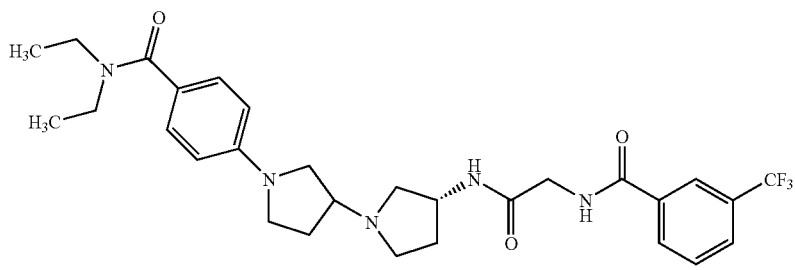

4

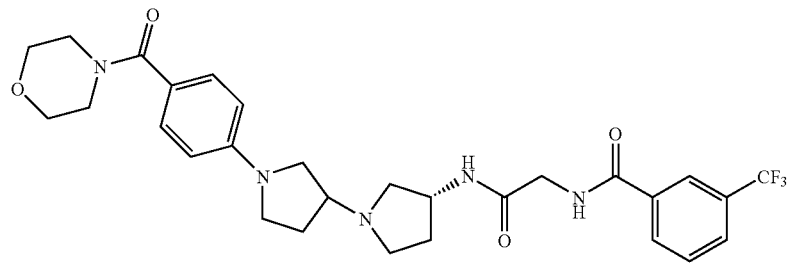

5

TABLE 1-continued
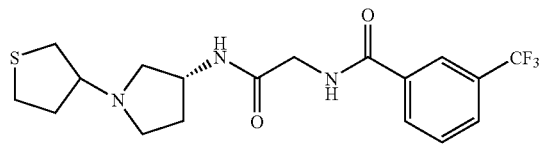
6
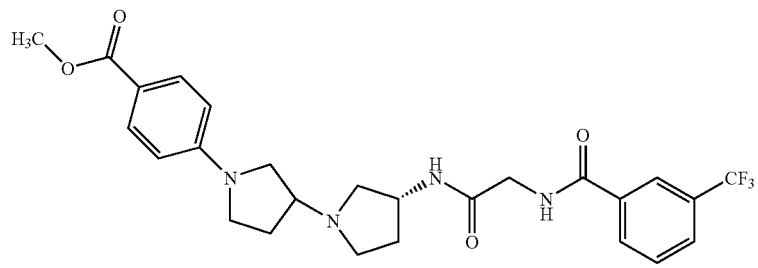
7
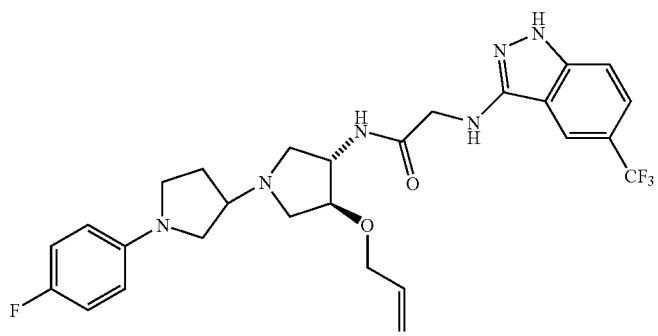
8
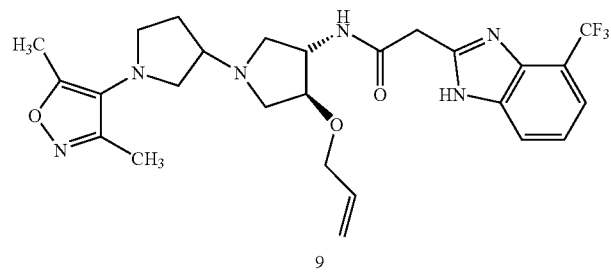
9
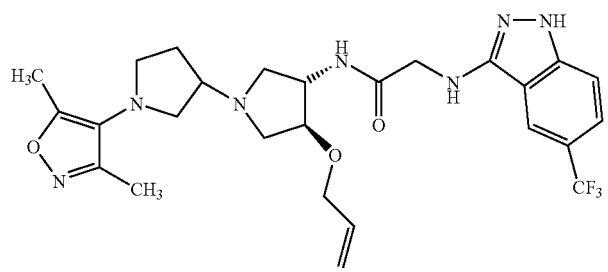
10

TABLE 1-continued
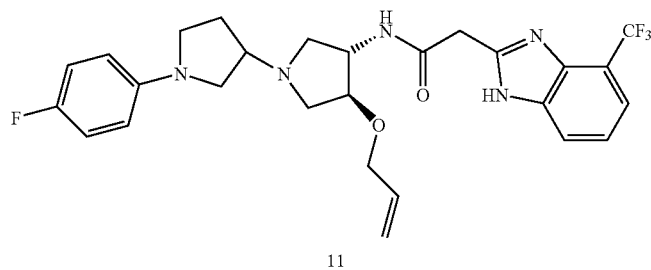
11
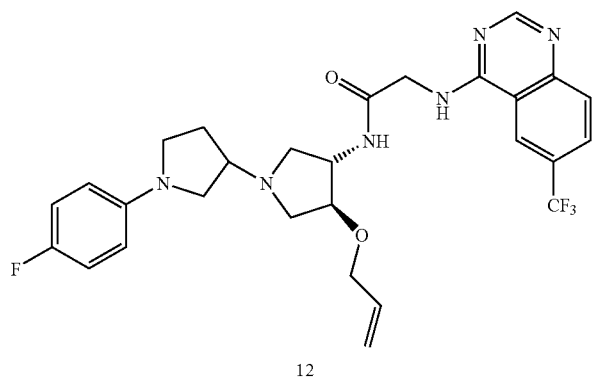
12
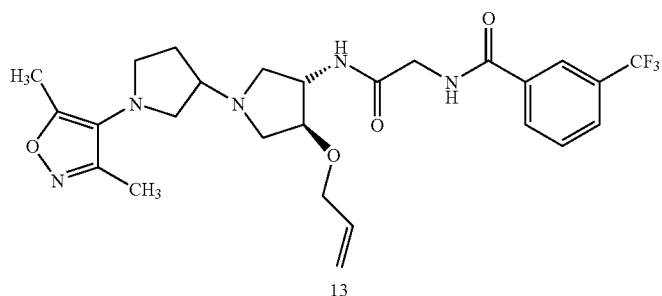
13
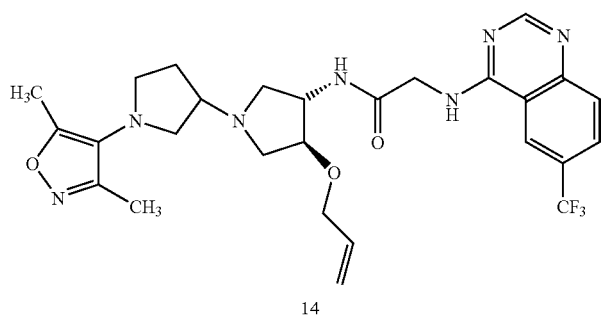
14
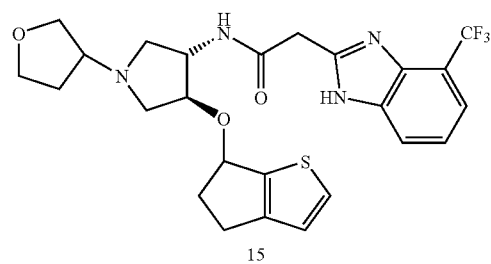
15

TABLE 1-continued
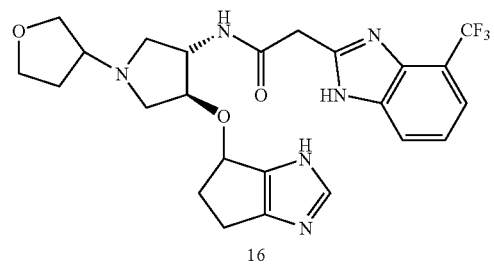
16
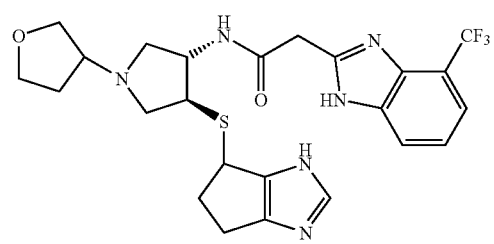
17
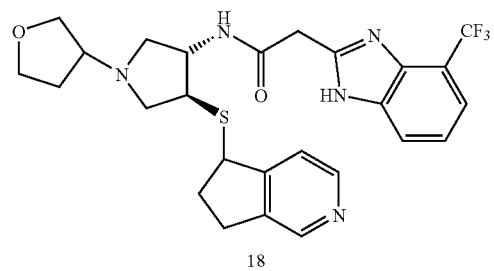
18
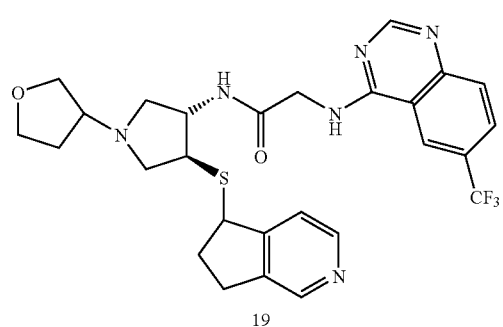
19
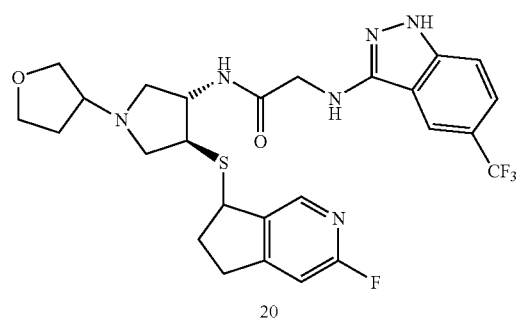
20

TABLE 1-continued
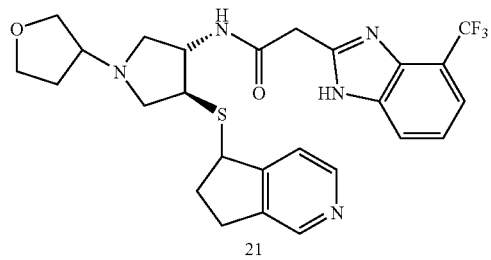
21
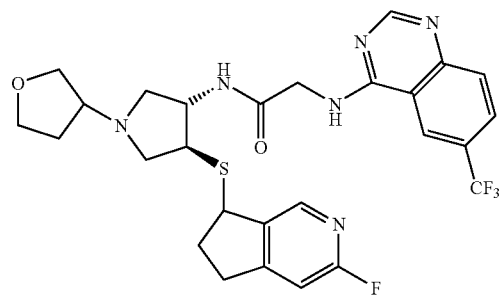
22
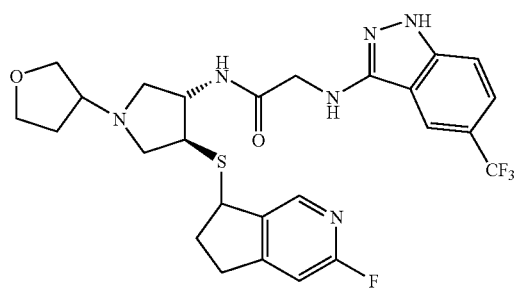
23
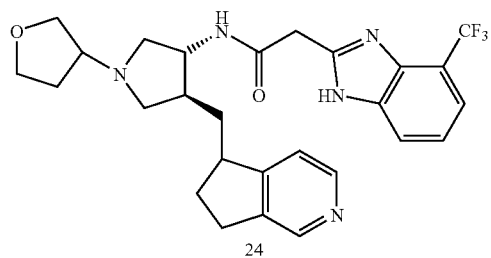
24
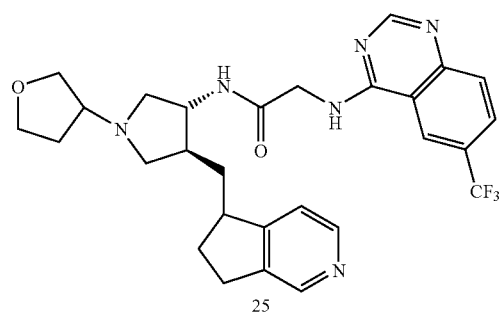
25

TABLE 1-continued
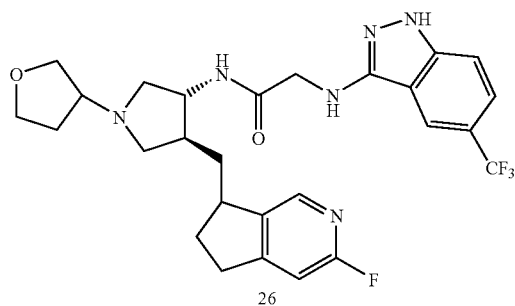
26
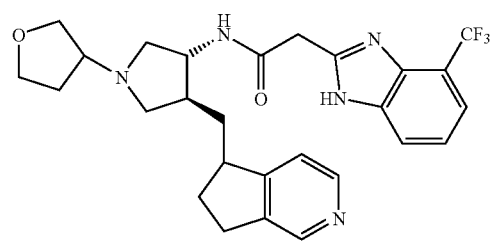
27
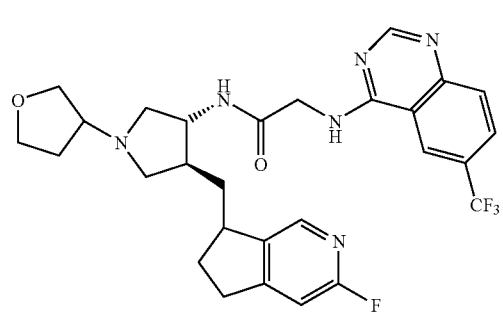
28
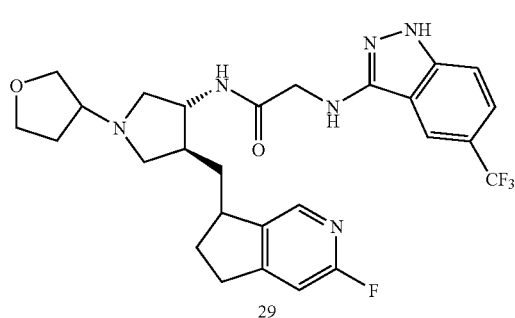
29
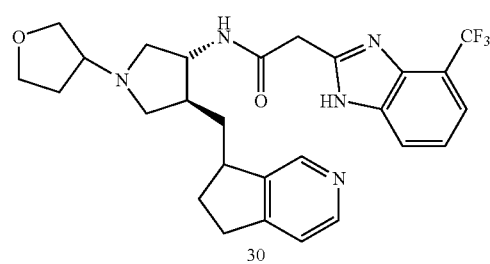
30

TABLE 1-continued
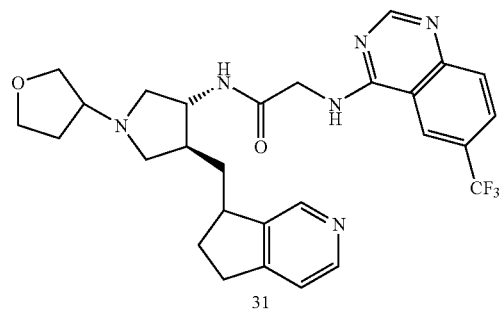
31
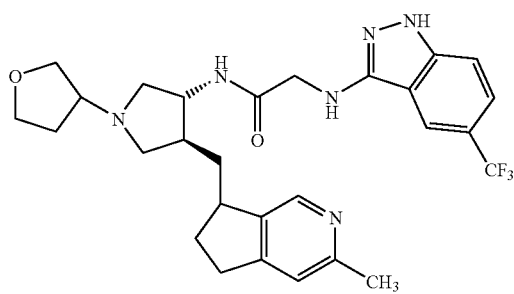
32
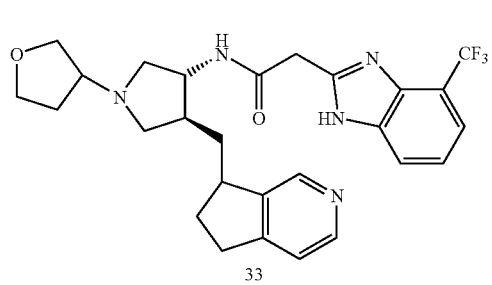
33
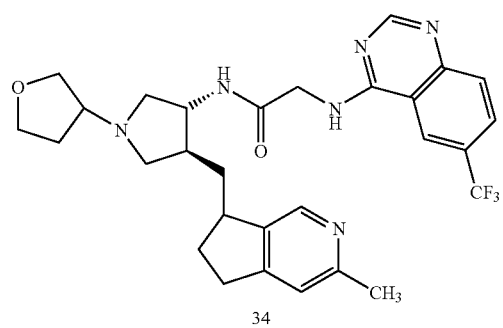
34
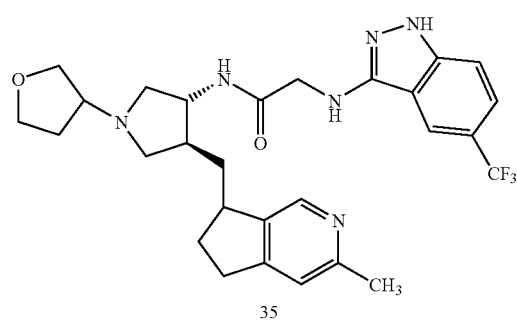
35

TABLE 1-continued
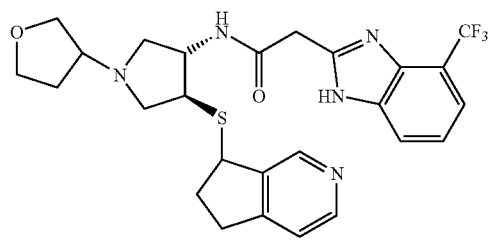
36
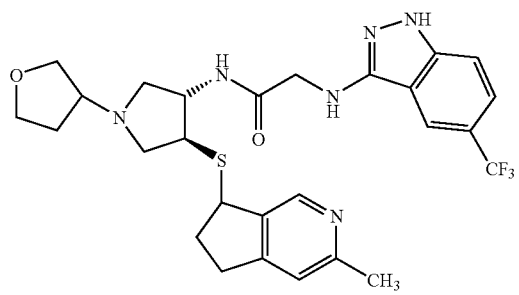
37
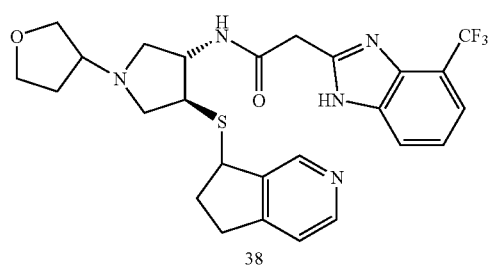
38
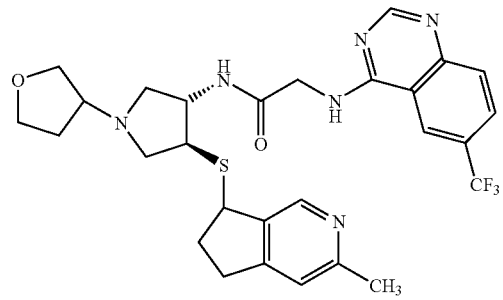
39
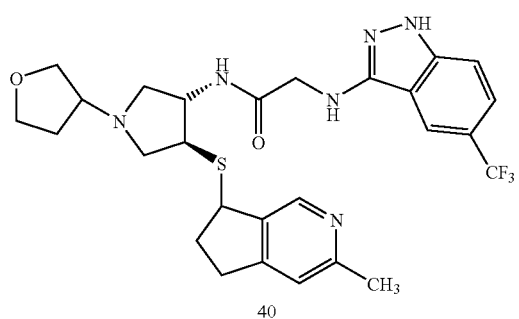
40

TABLE 1-continued
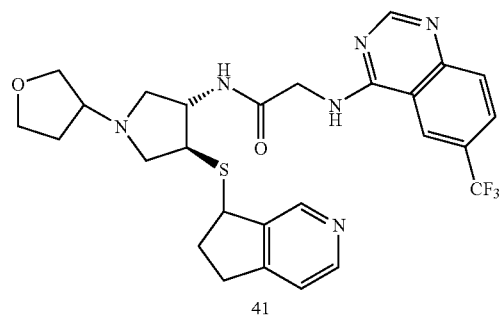
41
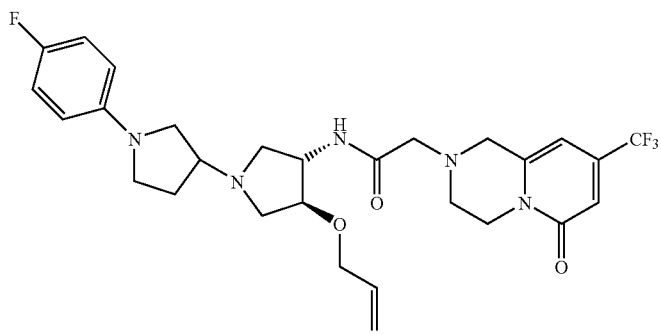
42
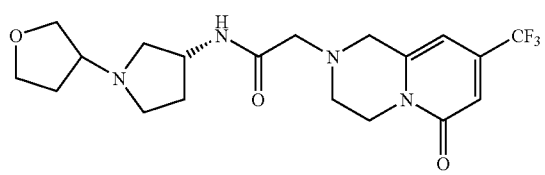
43
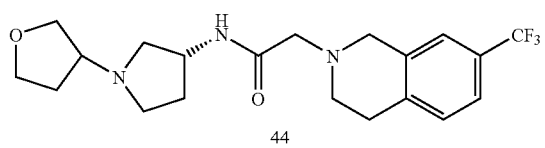
44
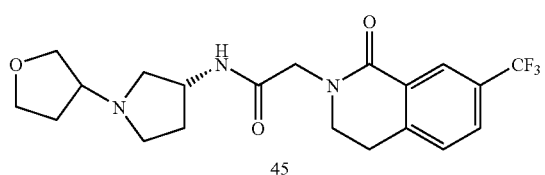
45
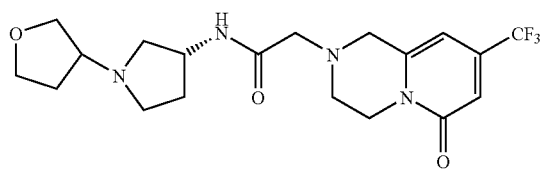
46

TABLE 1-continued
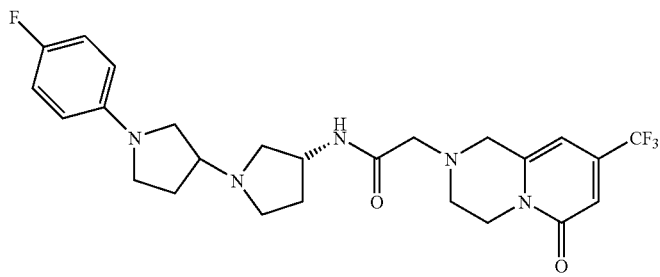
47
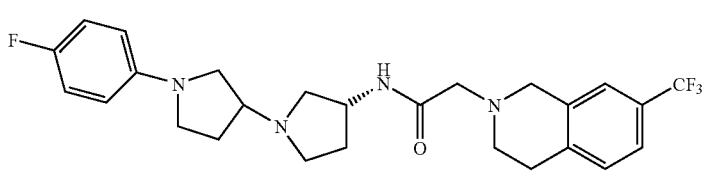
48
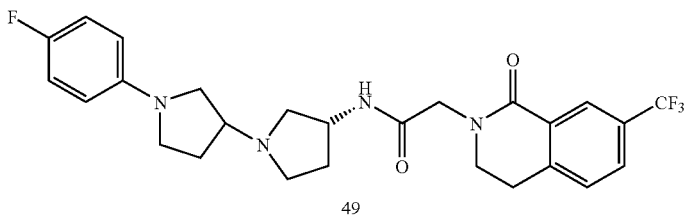
49
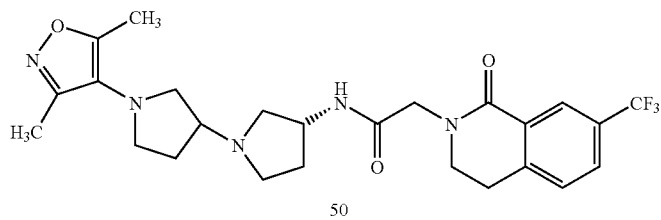
50
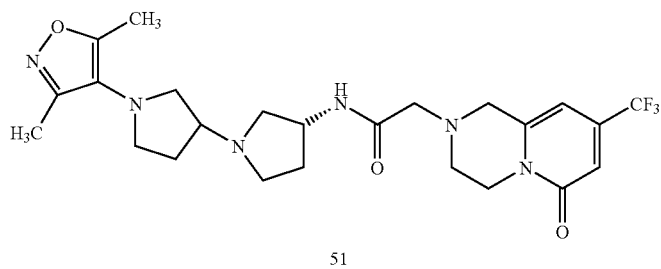
51
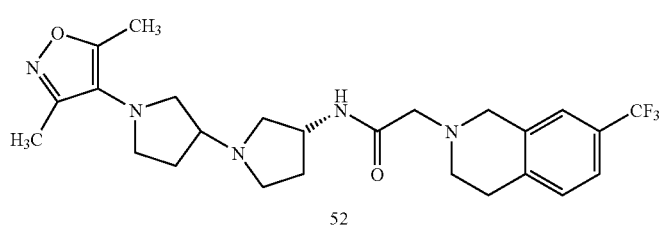
52

TABLE 1-continued
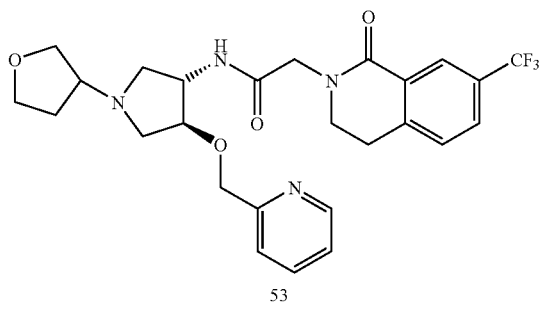
53
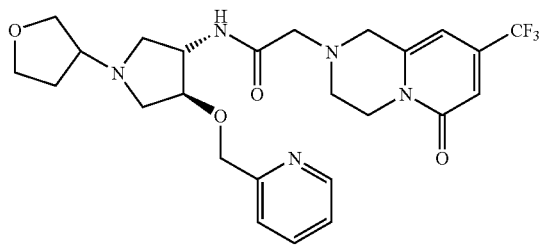
54
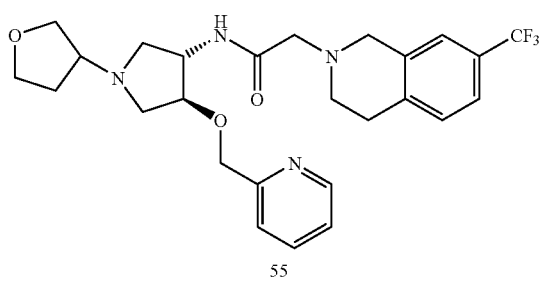
55
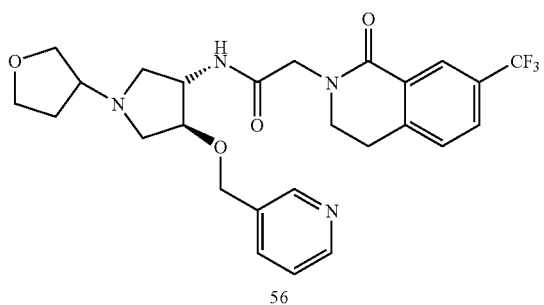
56
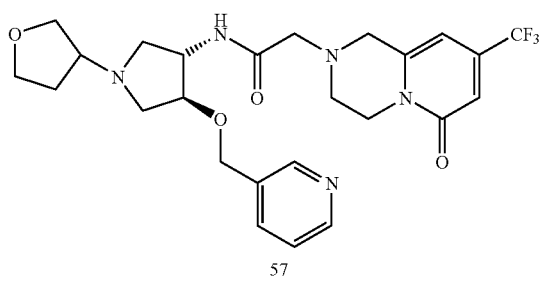
57

TABLE 1-continued
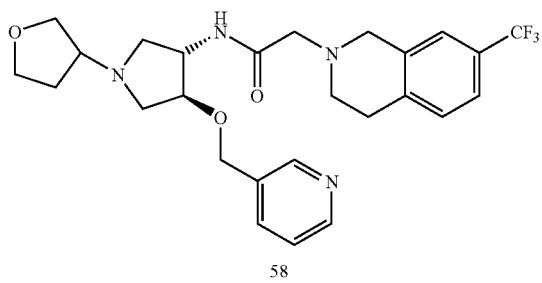
58
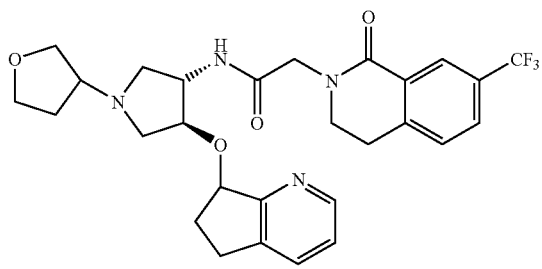
59
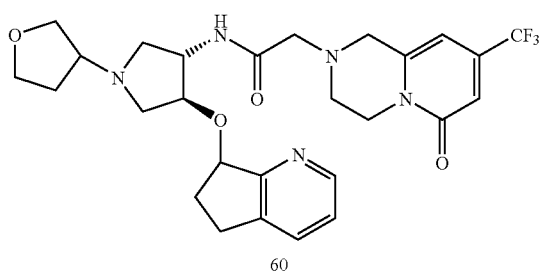
60
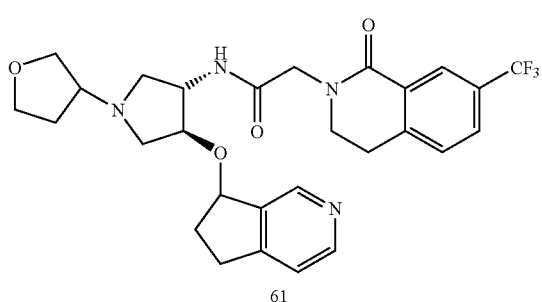
61
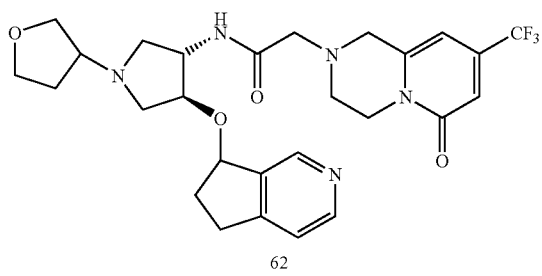
62

TABLE 1-continued
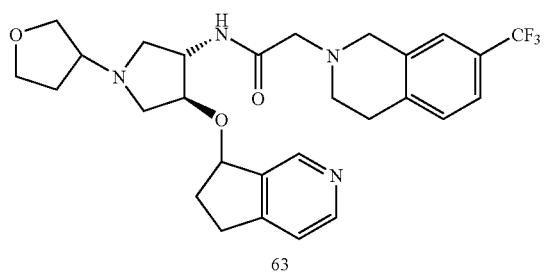
63
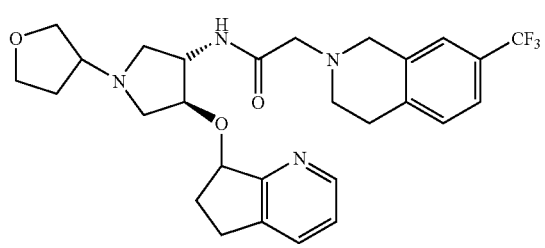
64
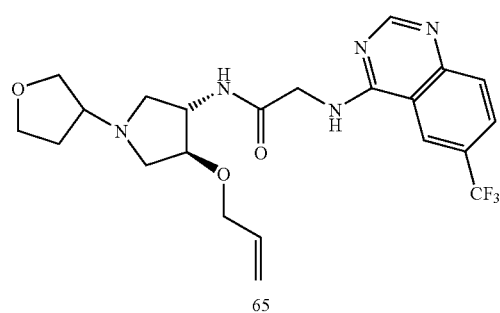
65
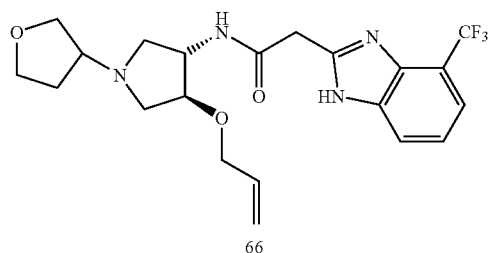
66
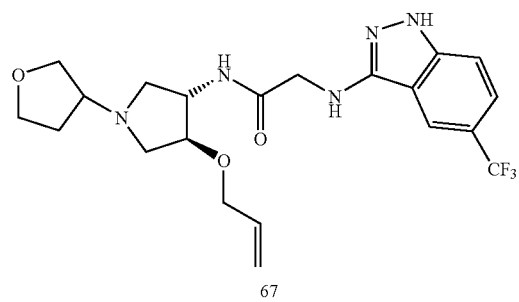
67

TABLE 1-continued
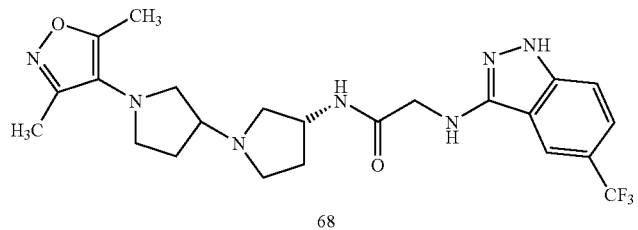
68
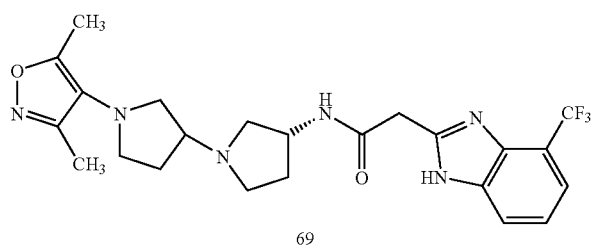
69
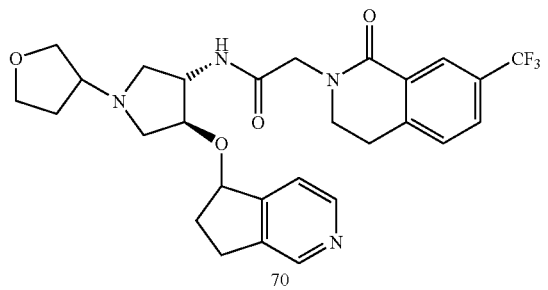
70
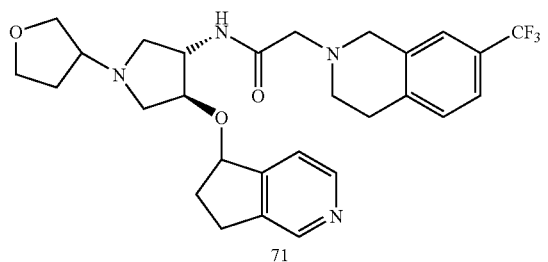
71
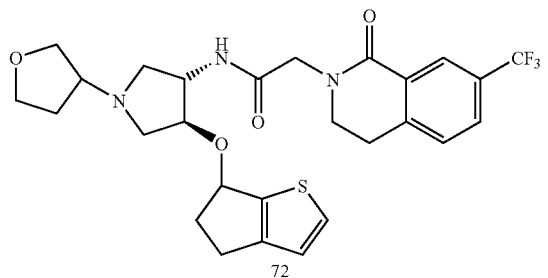
72
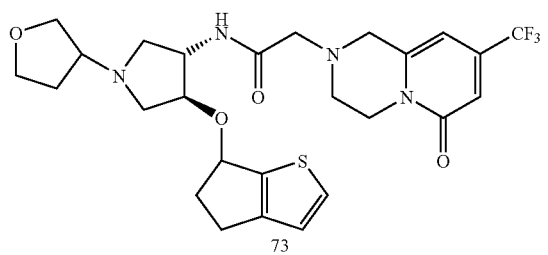
73

TABLE 1-continued
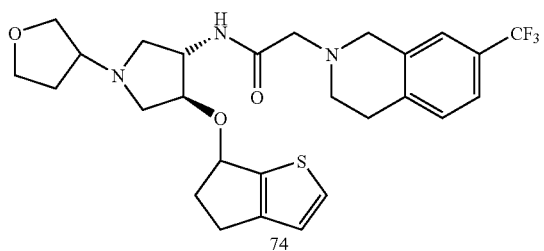
74
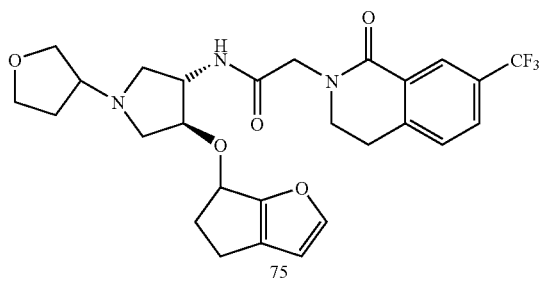
75
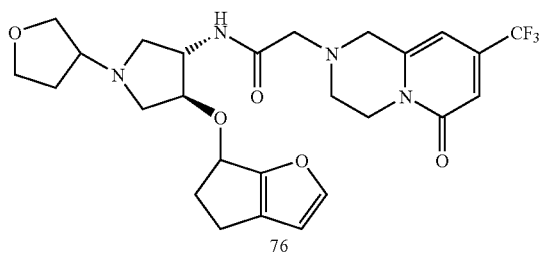
76
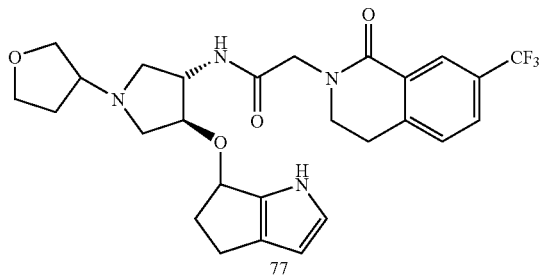
77
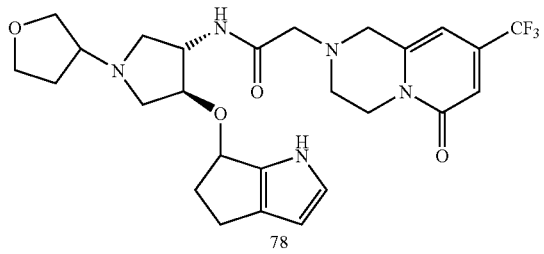
78
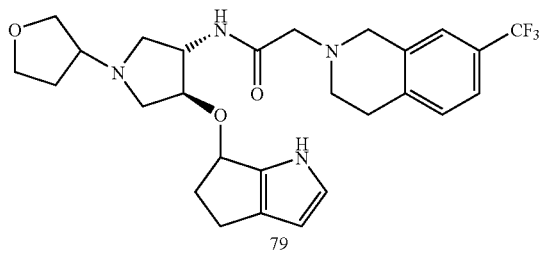
79

TABLE 1-continued
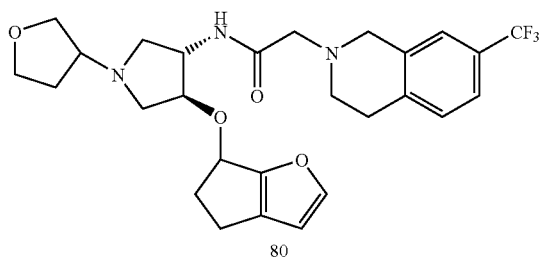
80
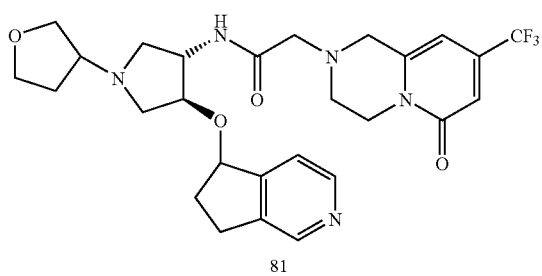
81
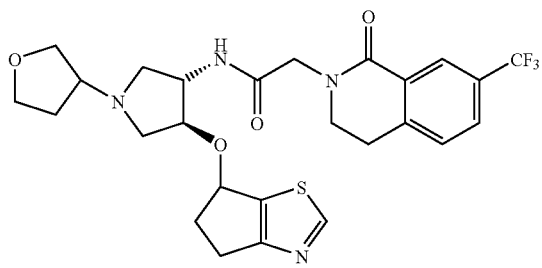
82
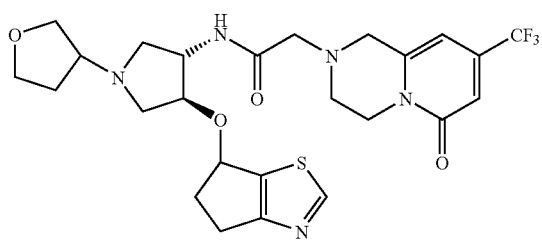
83
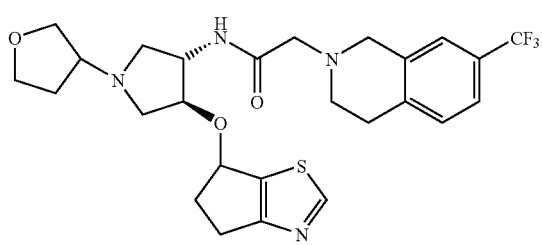
84

TABLE 1-continued
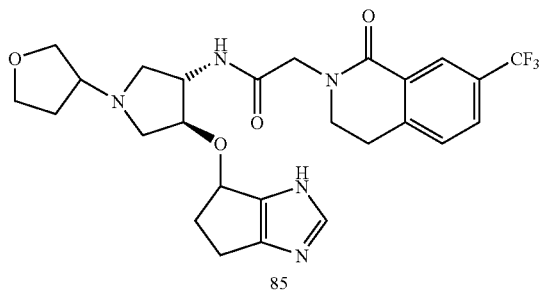
85
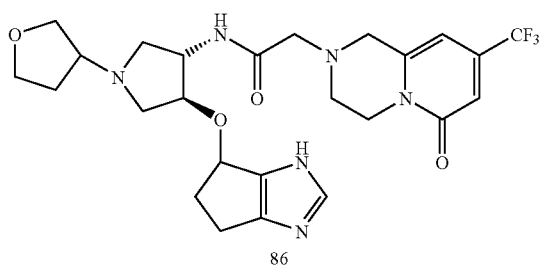
86
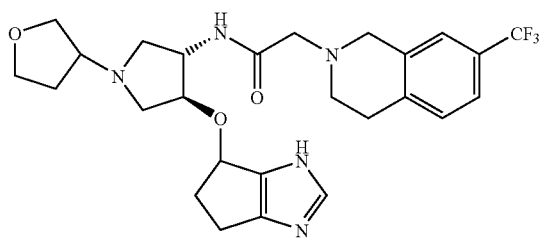
87
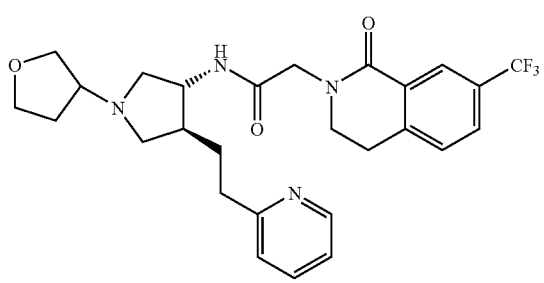
88
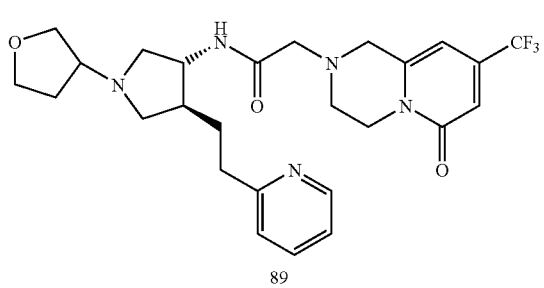
89

TABLE 1-continued
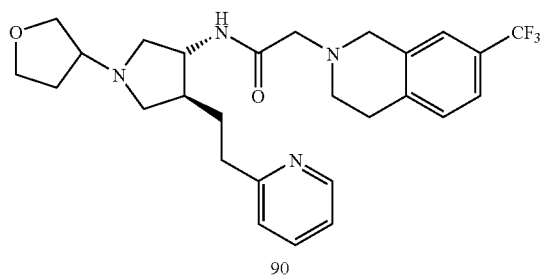
90
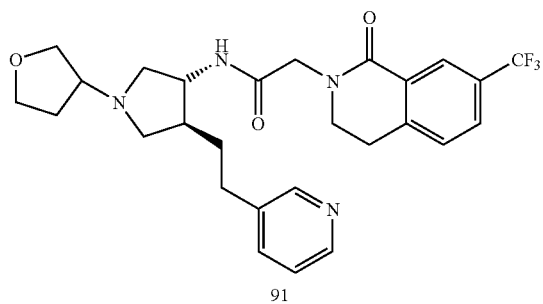
91
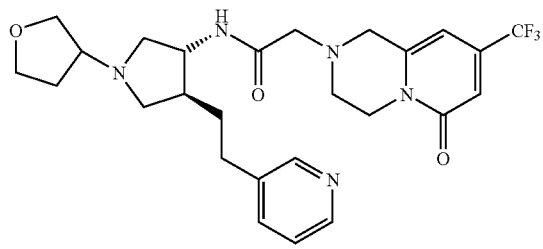
92
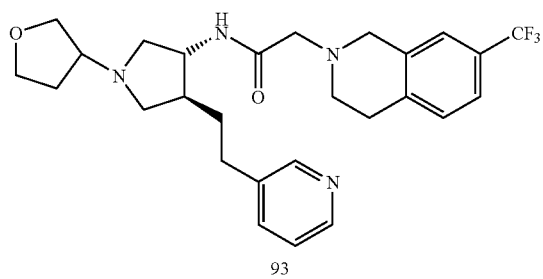
93
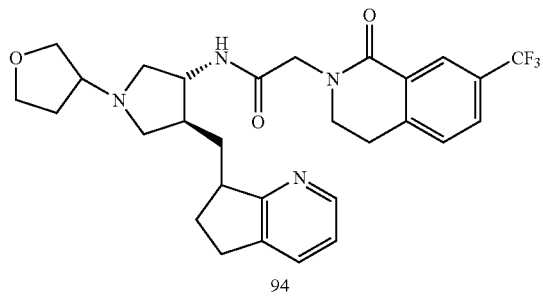
94

TABLE 1-continued
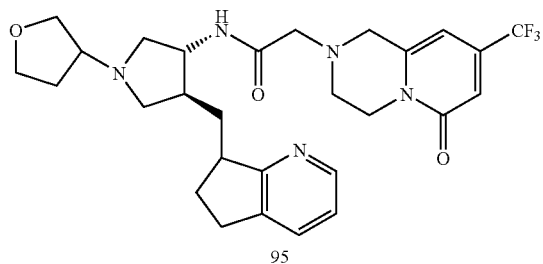
95
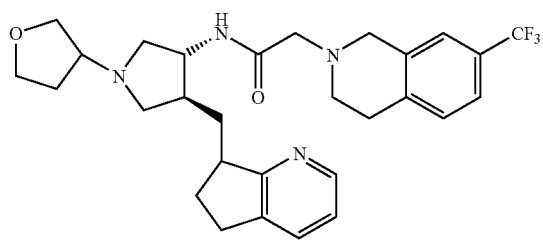
96
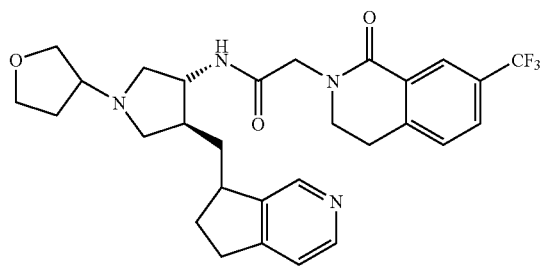
97
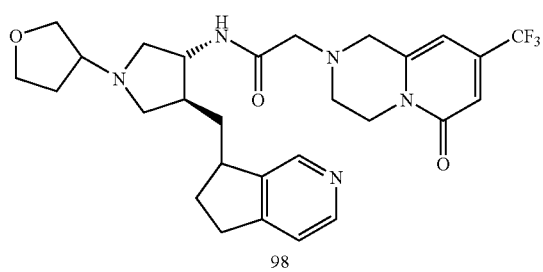
98
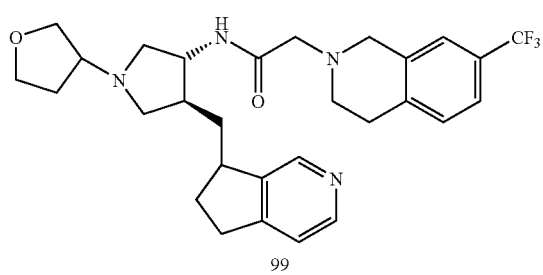
99

TABLE 1-continued
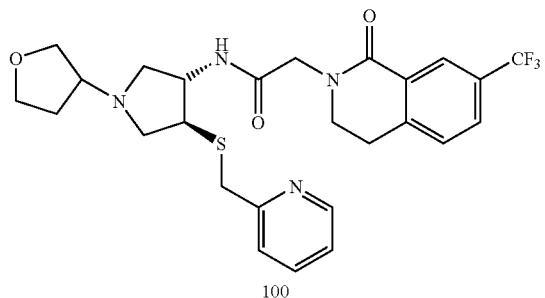
100
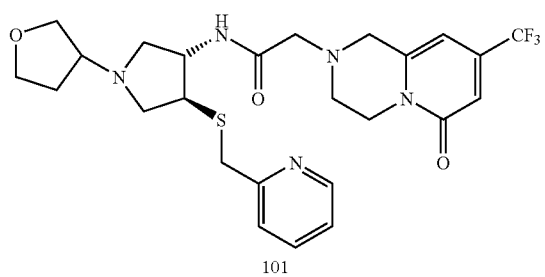
101
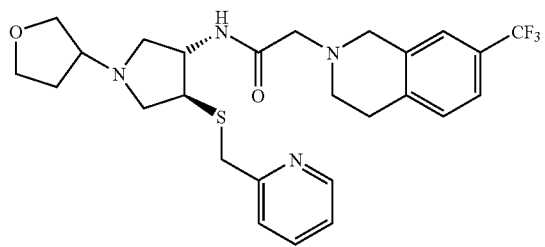
102
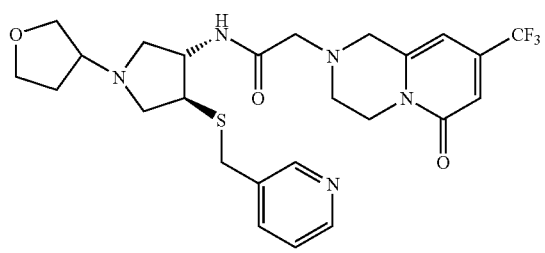
103
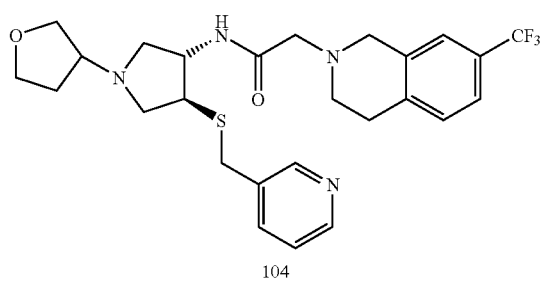
104

TABLE 1-continued
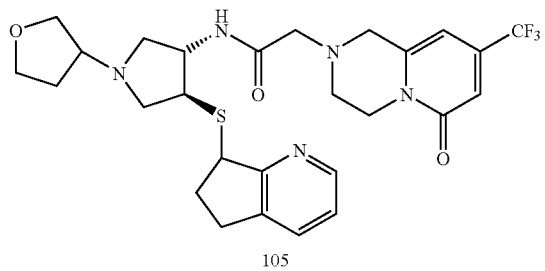
105
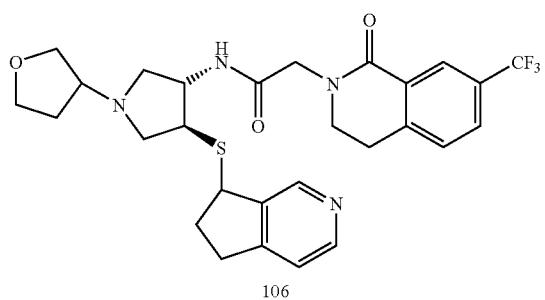
106
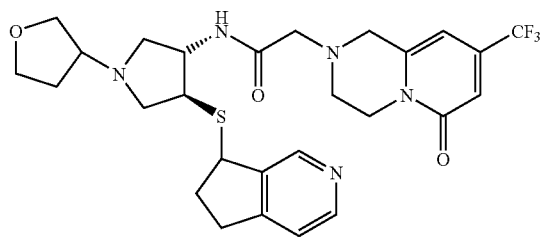
107
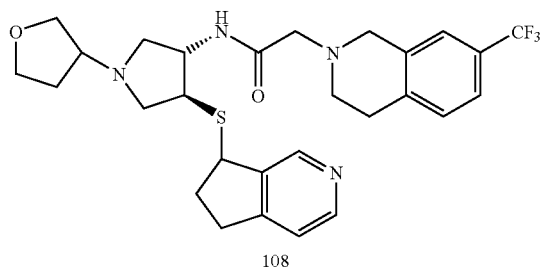
108
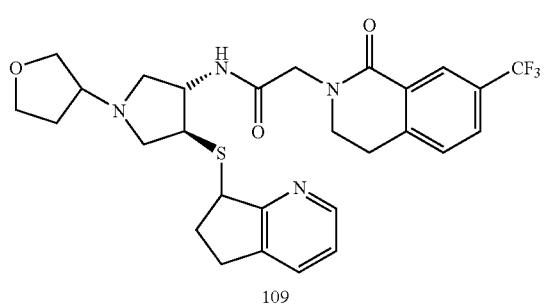
109

TABLE 1-continued
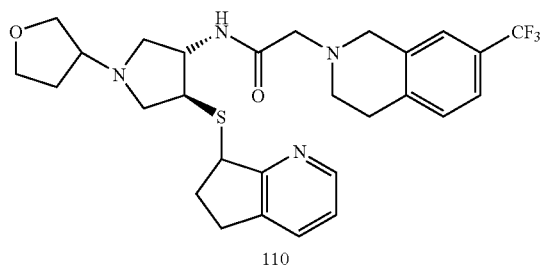
110
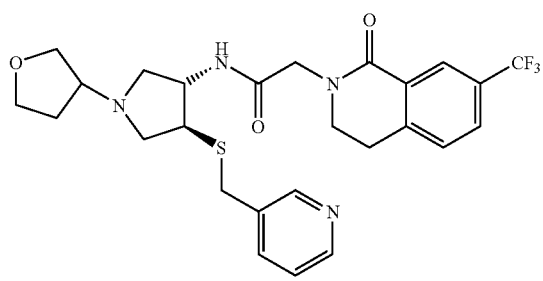
111
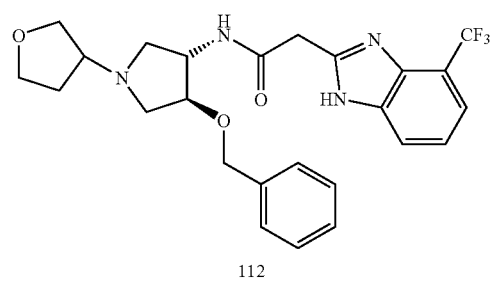
112
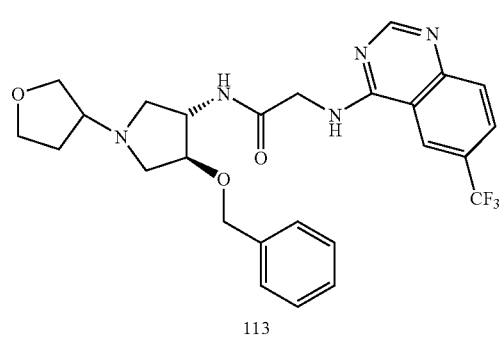
113
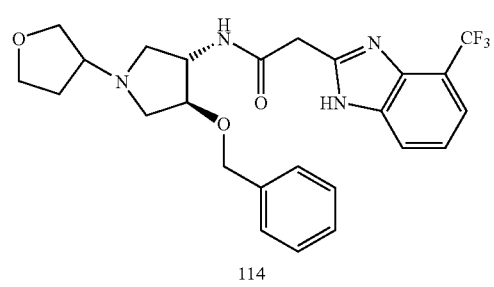
114

TABLE 1-continued
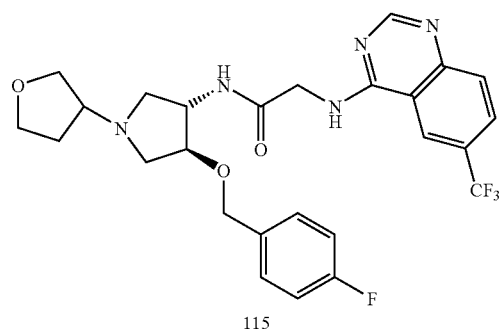
115
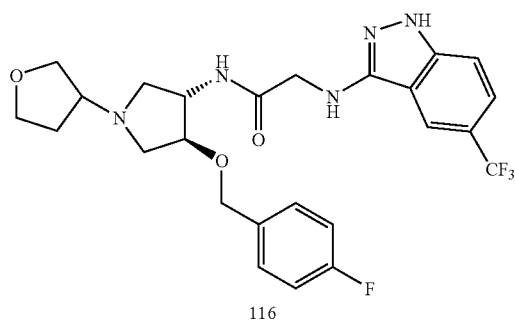
116
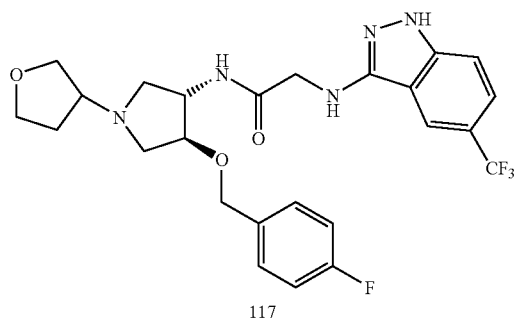
117
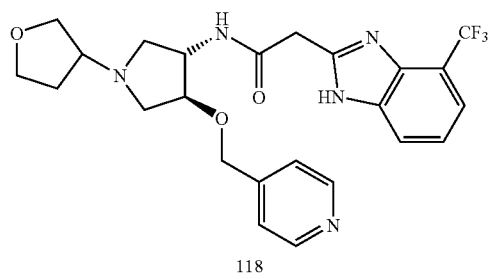
118
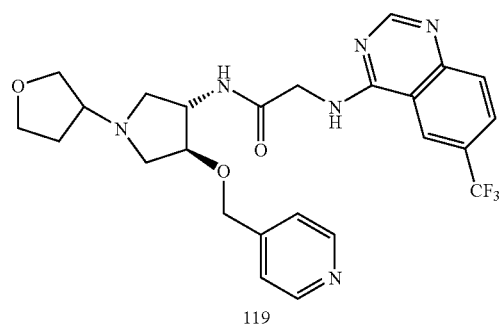
119

TABLE 1-continued
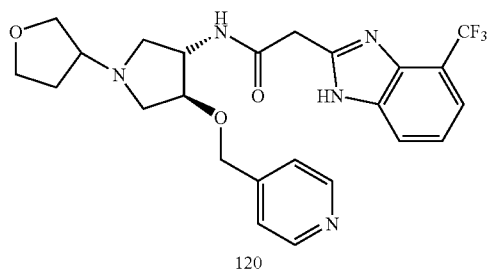
120
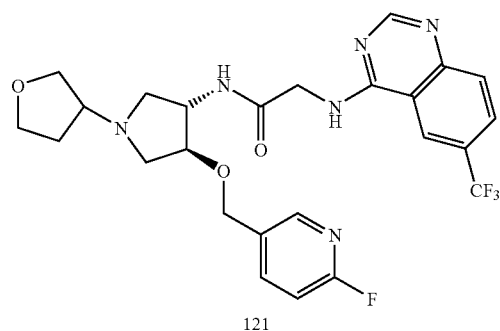
121
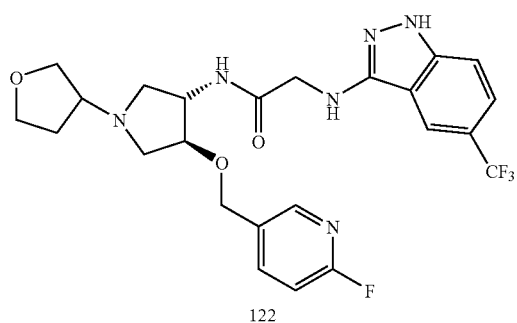
122
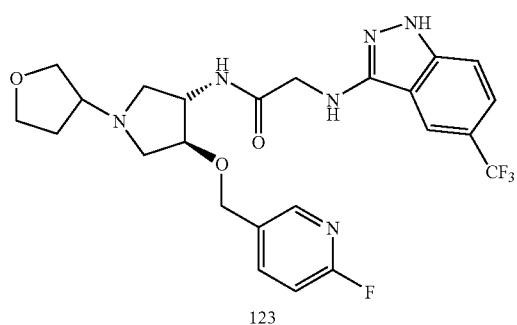
123
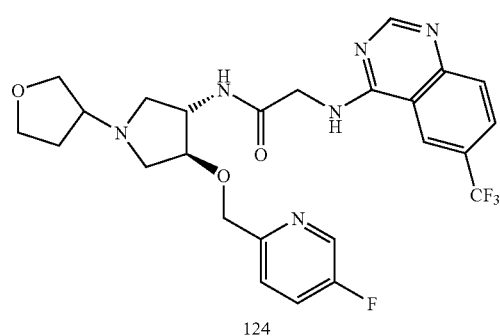
124

TABLE 1-continued
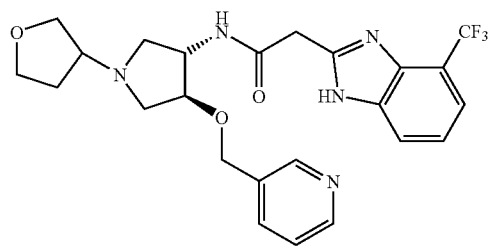
125
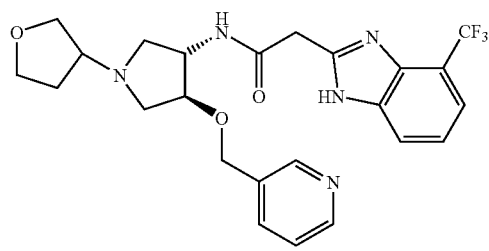
126
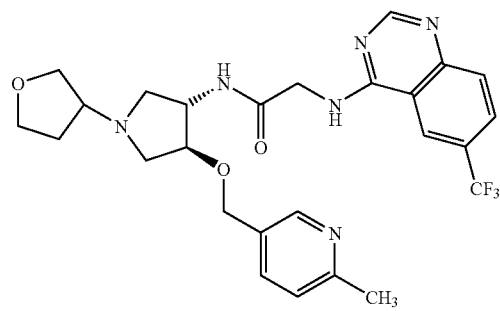
127
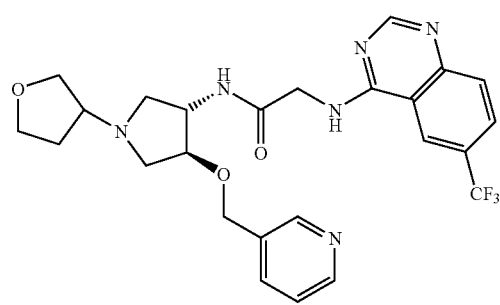
128
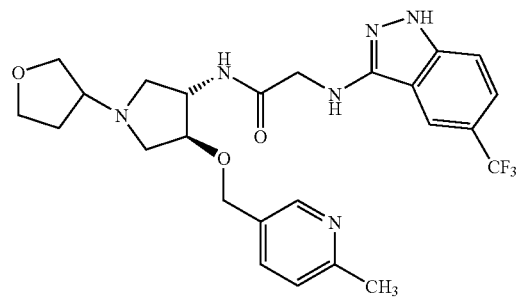
129

TABLE 1-continued
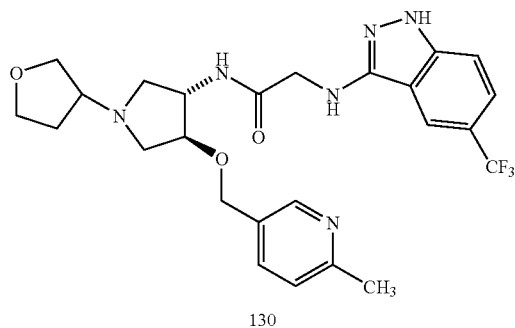
130
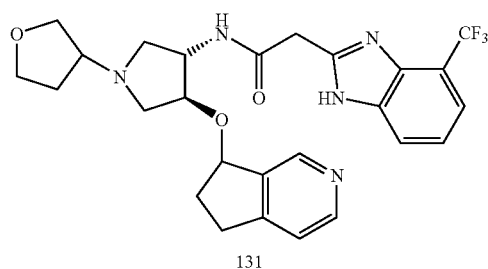
131
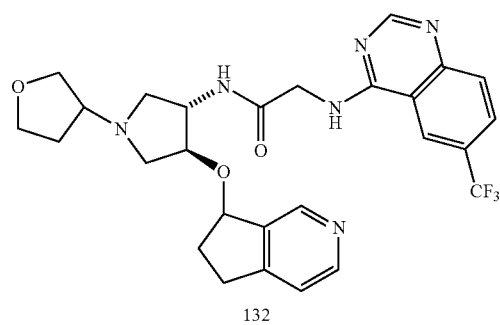
132
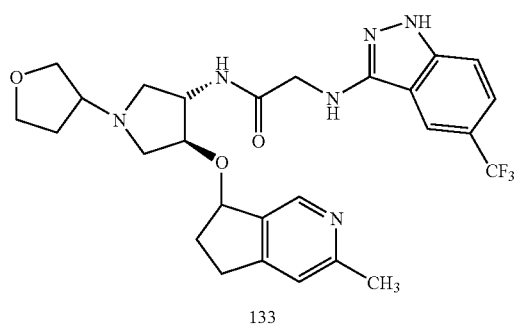
133
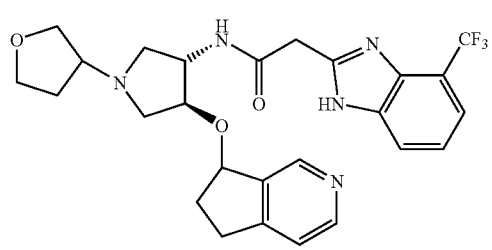
134

TABLE 1-continued
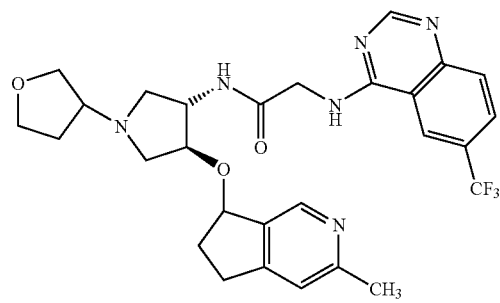
135
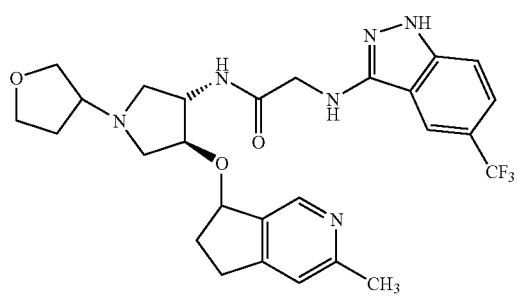
136
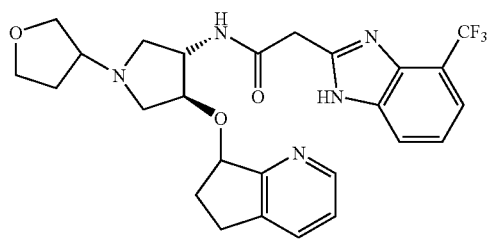
137
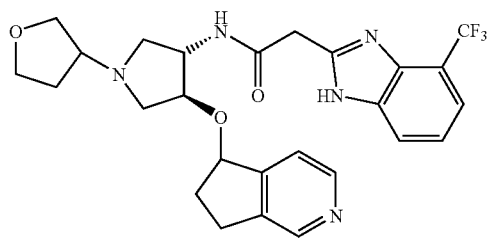
138
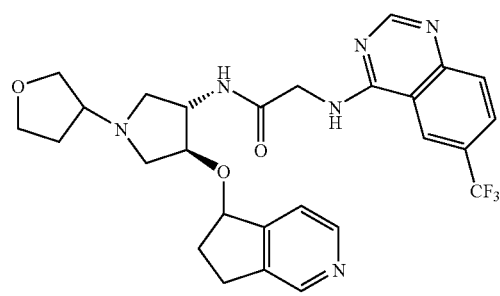
139

TABLE 1-continued

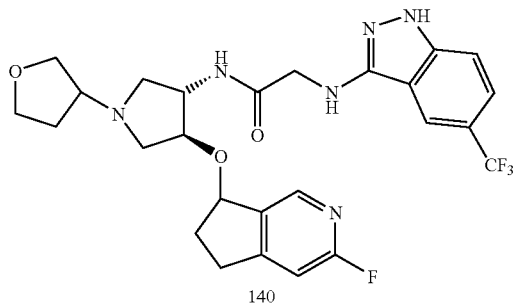

140

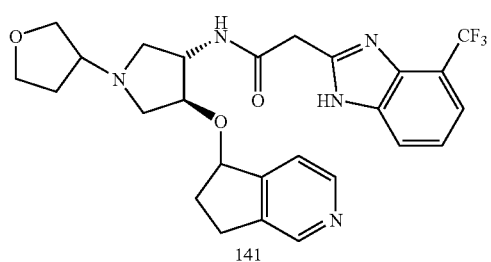

141

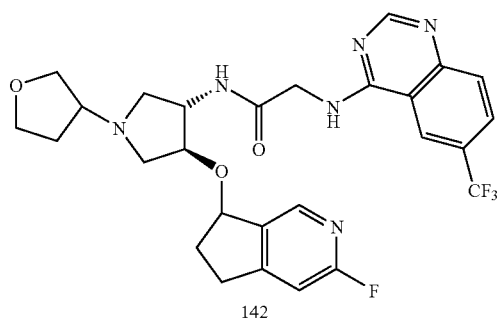

142

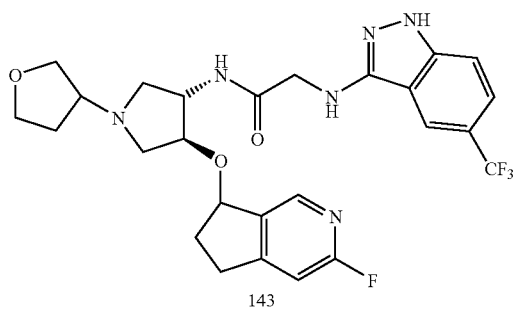

143

Biological Testing

THP-1 FLIPR Assay

The primary screening assay is a FLIPR (Fluorometric Imaging Plate Reader) assay using THP-1 cells (ATCC, Catalog No. TIB 202), a monocytic derived cell line that endogenously expresses CCR2.

The cells were resuspended at $1 \times 10^6$ cells/ml in dye loading media (growth media (RPMI+10% FBS (Fetal Bovine serum)+$5.5 \times 10^{-5}$ M 2-mercaptoethanol)+10 mM HEPES (N-2-hydroxyethylpiperazine-N'-2-ethane-sulfonic acid)+2.5 mM probenecid+fluo-3 (1:250)). The cells were incubated for 1 hour at 37° C. and then washed in FLIPR wash buffer (100 mL 10×BBSS (Hanks Buffered Saline Solution) (w/Ca++/Mg++)+20 mL 1M HEPES+1 g BSA+10 mL 250 mM probenecid+water (to make 1 L)) and plated at 50,000 cells/well in black/clear 384 well plates. The plates were transferred to FLIPR where the ability of different concentrations of compounds to inhibit MCP-1 induced calcium flux was assessed. Inhibition of the CCR2 response was reflected by a decrease of the fluorescence signal relative to the positive controls (MCP-1 alone).

THP-1 Whole Cell Radioligand Binding Assay

The cells were washed with PBS (phosphate buffered saline) and resuspended in binding buffer (10 mM HEPES pH 7.2, 1×HBSS (w/Ca$^{2+}$, Mg$^{2+}$) 0.5% BSA, 0.02% Na-azide) at $4 \times 10^6$ cells/ml (for 200,000 cells/well). Cells were incubated with 0.1 to 0.2 nM [$^{125}$I]-labeled MIP-1α with or without unlabeled competitor (MIP-1α) or various concentrations of compounds for 60 minutes at room temperature. The assay was terminated by vacuum filtration through glass fiber filters (GF/B, Packard) which were presoaked in 0.3% polyethyleneimine. The filters were washed with wash buffer (10 mM HEPES, pH 7.2, 1 mM $CaCl_2$, 5 mM $MgCl_2$ 0.5M NaCl), dried and the amount of bound radioactivity was determined by scintillation counting.

Compounds of the invention have been shown to inhibit CCR2, preferably at a concentration less than 100 nM.

While this invention has been particularly shown and described with references to preferred embodiments thereof, it will be understood by those skilled in the art that various changes in form and details may be made therein without departing from the scope of the invention encompassed by the appended claims.

The invention claimed is:
1. A compound of formula I:

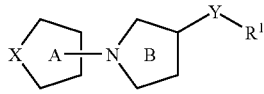

or a pharmaceutically acceptable salt thereof, wherein:
Y is $-Y_1-Y_2-$, wherein:
 $Y_1$ is $-SO_2N(R')-$, $-C(O)N(R')-$; $-C(O)N(R')C(O)-$, $-N(R')SO_2-$, $-N(R')SO_2N(R')-$, $-N(R')C(O)-$, $-NR'C(O)N(R')-$, or $-N(R')C(O)O-$; and
 $Y_2$ is absent or is an optionally substituted $C_{1-6}$ alkylene chain, wherein one or two methylene units of $Y_2$ are optionally and independently interrupted by $-O-$, $-S-$, $-N(R')-$, $-C(O)-$, $-OC(O)-$, $-C(O)O-$, $-S(O)-$, $-S(O)_2-$, $-C(O)N(R')-$, $-N(R')C(O)-$, $-N(R')C(O)N(R')-$, $-N(R')C(O)O-$, $-OC(O)N(R')-$, $-N(R')S(O)_2-$, or $-S(O)_2N(R')-$, or wherein $Y_2$, or a portion thereof, is an optionally substituted ring selected from 3-6-membered cycloaliphatic, 3-6-membered heterocyclyl having 1-3 heteroatoms independently selected from nitrogen, oxygen, or sulfur, 6-membered aryl, or 5-6-membered heteroaryl having 1-3 heteroatoms independently selected from nitrogen, oxygen, or sulfur;
 each R' is independently hydrogen or optionally substituted $C_{1-6}$aliphatic;
$R^1$ is an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
ring A is substituted at one or more carbon atoms with m independent occurrences of $R^2$;
m is 0-6;
each occurrence of $R^2$ is independently halogen, $=O$, $=S$, $-CN$, $-R^{2b}$, $-N(R^{2a})_2$, $-OR^{2a}$, $-SR^{2b}$, $-S(O)_2R^{2b}$, $-C(O)R^{2a}$, $-C(O)OR^{2a}$, $-C(O)N(R^{2a})_2$, $-S(O)_2 N(R^{2a})_2$, $-OC(O)N(R^{2a})_2$, $-N(R')C(O)R^{2a}$, $-N(R')SO_2R^{2b}$, $-N(R')C(O)OR^{2a}$, $-N(R')C(O)N(R^{2a})_2$, or $-N(R')SO_2N(R^{2a})_2$, or two occurrences of $R^{2a}$ or $R^{2b}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{2a}$, taken together with the nitrogen atom to which they are bound, form an optionally substituted 3-7-membered heterocyclyl ring having 1-3 additional heteroatoms selected from nitrogen, oxygen, or sulfur;
 each occurrence of $R^{2a}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
 each occurrence of $R^{2b}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
ring B is substituted with r independent occurrences of $-R^3$;
r is 0-6;
each occurrence of $R^3$ is independently $-R^{3a}$, $-T_1-R^{3d}$, or $-V_1-T_1-R^{3d}$, wherein:
 each occurrence of $-R^{3a}$ is independently halogen, $-CN$, $-NO_2$, $-R^{3c}$, $-N(R^{3b})_2$, $-OR^{3b}$, $-SR^{3c}$, $-S(O)_2R^{3c}$, $-C(O)R^{3b}$, $-C(O)OR^{3b}$, $-C(O)N(R^{3b})_2$, $-S(O)_2N(R^{3b})_2$, $-OC(O)N(R^{3b})_2$, $-N(R')C(O)R^{3b}$, $-N(R')SO_2R^{3c}$, $-N(R')C(O)OR^{3b}$, $-N(R')C(O)N(R^{3b})_2$, or $-N(R')SO_2N(R^{3b})_2$, or two occurrences of $R^{3b}$ or $R^{3c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{3b}$, taken together with the nitrogen atom to which they are bound, form an optionally substituted 3-7-membered heterocyclyl ring having 1-3 additional heteroatoms selected from nitrogen, oxygen, or sulfur;
 each occurrence of $R^{3b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
 each occurrence of $R^{3c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
 each occurrence of $R^{3d}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10- membered heteroaryl having 1-5 heteroatoms independently selected from nitrogen, oxygen, or sulfur;

each occurrence of $V_1$ is independently —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—;

each occurrence of $T_1$ is independently $C_{1-6}$ alkylene chain optionally substituted with $R^{3a}$, wherein the alkylene chain optionally is interrupted by —C(R')═C(R')—, —C≡C—, N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—or wherein $T^1$ or a portion thereof optionally forms part of an optionally substituted 3-7 membered cycloaliphatic or heterocyclyl ring;

X is —O—;

W is absent or is a group selected from —W$_1$-L$_2$-W$_2$—, wherein W$_1$ and W$_2$ are each independently absent or are an optionally substituted C$_{1-3}$alkylene chain, and L$_2$ is absent or is a group selected from —N(R)—, —O—, —S—, —S(O)—, —S(O)$_2$—, —C(O)—, —C(O)O—, —C(O)N(R)—, —S(O)$_2$N(R)—, —OC(O)N(R)—, —N(R)C(O)—, —N(R)SO$_2$—, —N(R)C(O)O—, —N(R)C(O)N(R)—, —N(R)SO$_2$N(R)—, —OC(O)—, or —C(O)N(R)—O—, wherein R is hydrogen or C$_1$-C$_4$alkyl, provided that if W$_1$ is absent then L$_2$ is selected from —C(O)—, —C(O)O—, —C(O)O—, —S(O)—, —S(O)$_2$—, —C(O)N(R)—, or —S(O)$_2$N(R)—

$R^4$ is an optionally substituted monocyclic or bicyclic ring selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and provided that the compound is other than:
a) 1-Pyrrolidinecarboxamide, 3-[6-(4-chlorophenyl)-4-oxothieno[3,2-d]pyrimidin-3(4H)-yl]-N-methyl-N-[(3S)-1-(tetrahydro-2-oxo-3-furanyl)-3-pyrrolidinyl]-, (3S)
b) Penitol, 1,4-anhydro-2,3,5-trideoxy-3-[(3R)-3-[methyl[[(3S)-3-[methyl[[(4-phenoxylphenol)amino]carbonyl]amino]-1-pyrrolidinyl]carbonyl]amino]-1-pyrrolidinyl] or
c) Penitol, 1,4-anhydro-2,3,5-trideoxy-3-[(3R)-3-[methyl[[(3S)-3-[methyl[[4'-(trifluoromethyl)[1,1'-biphenyl]-4-yl]carbonyl]amino]-1-pyrrolidinyl]carbonyl]amino]-1-pyrrolidinyl].

2. The compound of claim 1, wherein the compound has the structure of formula I-A-I or I-A-ii:

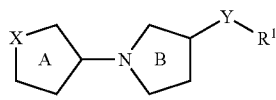

I-A-i

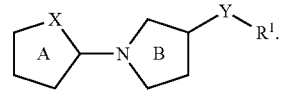

I-A-ii

3. The compound of claim 2, wherein r is 0, 1, or 2.
4. The compound of claim 3, wherein r is 1 and the compound has the structure of formula I-B:

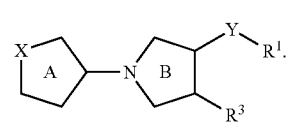

I-B

5. The compound of claim 4, wherein $R^1$ is an optionally substituted aryl group.
6. The compound of claim 4, wherein $R^1$ is an optionally substituted 5-8-membered monocyclic or 7-10-membered bicyclic heterocyclyl or heteroaryl ring having 1-4 heteroatoms independently selected from N, O, or S.
7. The compound of claim 6, wherein $R^1$ is an optionally substituted group selected from:

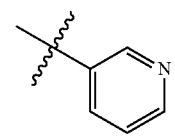

a

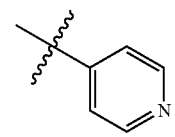

b

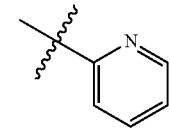

c

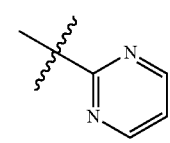

d

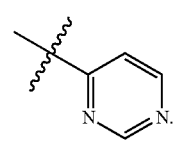

e

8. The compound of claim 6, wherein $R^1$ is an optionally substituted group selected from:
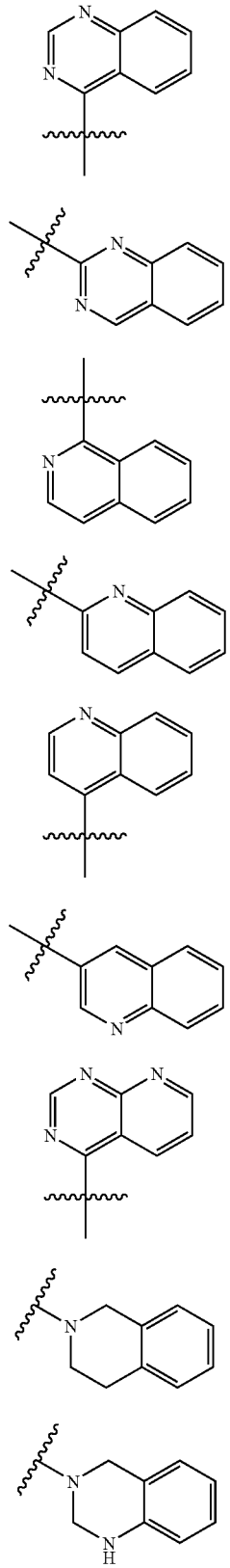
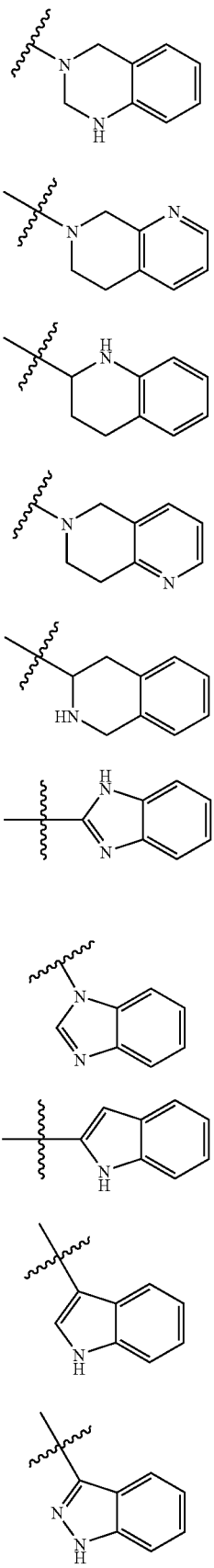

-continued

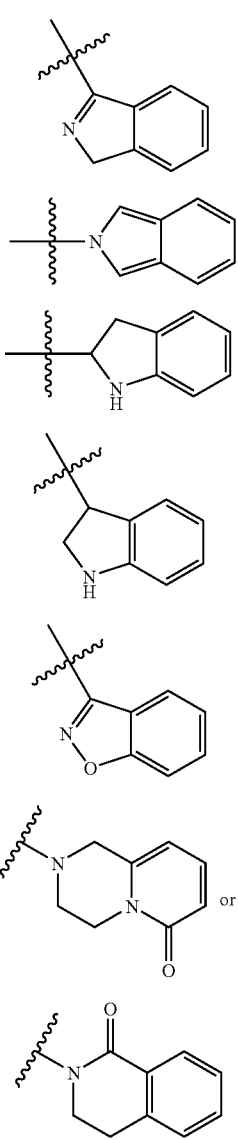

9. The compound of claim 4, wherein:
$R^1$ is an optionally substituted aryl group or $R^1$ is an optionally substituted 5-8-membered monocyclic or 7-10-membered bicyclic heterocyclyl or heteroaryl ring having 1-4 heteroatoms independently selected from N, O, or S, and
$R^1$ is optionally substituted with 1-3 occurrences of $R^{1a}$, wherein each occurrence of $R^{1a}$ is independently halogen, =O, =S, —CN, —NO$_2$, —R$^{1c}$, —N(R$^{1b}$)$_2$, —OR$^{1b}$, —SR$^{1c}$, —S(O)$_2$R$^{1c}$, —C(O)R$^{1b}$, —C(O)OR$^{1b}$, —C(O)N(R$^{1b}$)$_2$, —S(O)$_2$N(R$^{1b}$)$_2$, —OC(O)N(R$^{1b}$)$_2$, —N(R')C(O)R$^{1b}$, —N(R')SO$_2$R$^{1c}$, N(R')C(O)OR$^{1b}$, —N(R')C(O)N(R$^{1b}$)$_2$, or —N(R')SO$_2$N(R$^{1b}$)$_2$, or two occurrences of R$^{1b}$ or R$^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of R$^{1b}$, taken together with the nitrogen atom to which they are bound, form an optionally substituted 3-7-membered heterocyclyl ring having 1-3 additional heteroatoms selected from nitrogen, oxygen, or sulfur, wherein each occurrence of R$^{1b}$ is independently hydrogen or an optionally substituted group selected from C$_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of R$^{1c}$ is independently an optionally substituted group selected from C$_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

10. The compound of claim 9, wherein each occurrence of R$^{1a}$ is independently =O, halogen, —R$^{1c}$, —N(R$^{1b}$)$_2$, —OR$^{1b}$ or —SR$^{1c}$.

11. The compound of claim 9, wherein each occurrence of R$^{1a}$ is independently C$_{1-4}$fluoroalkyl, —O(C$_{1-4}$fluoroalkyl), or —S(C$_{1-4}$fluoroalkyl).

12. The compound of claim 4, wherein Y$_1$ is —SO$_2$N(R')—, —C(O)NR'—, or —N(R')S(O)$_2$—.

13. The compound of claim 4, wherein Y$_1$ is —N(R')C(O)—.

14. The compound of claim 4, wherein Y is selected from:

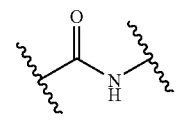
i

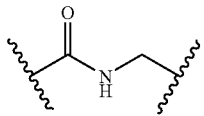
ii

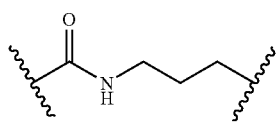
iii

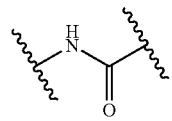
iv

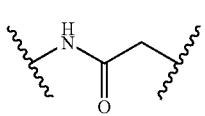
v

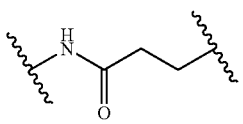
vi

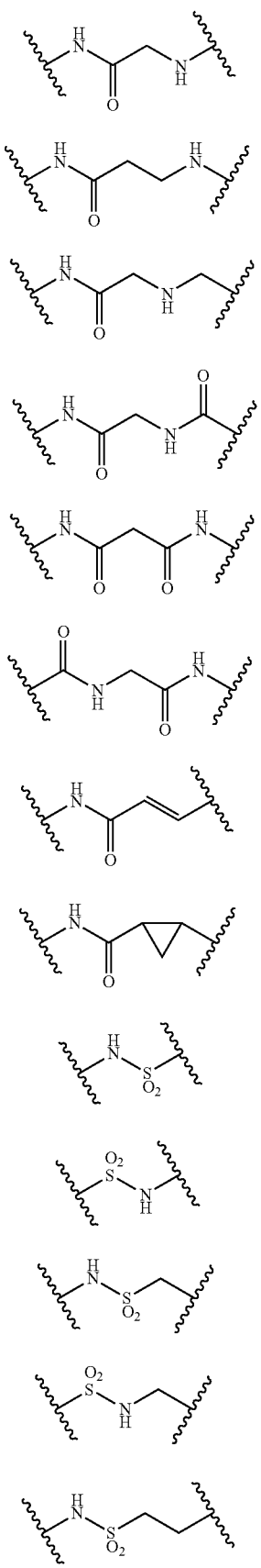

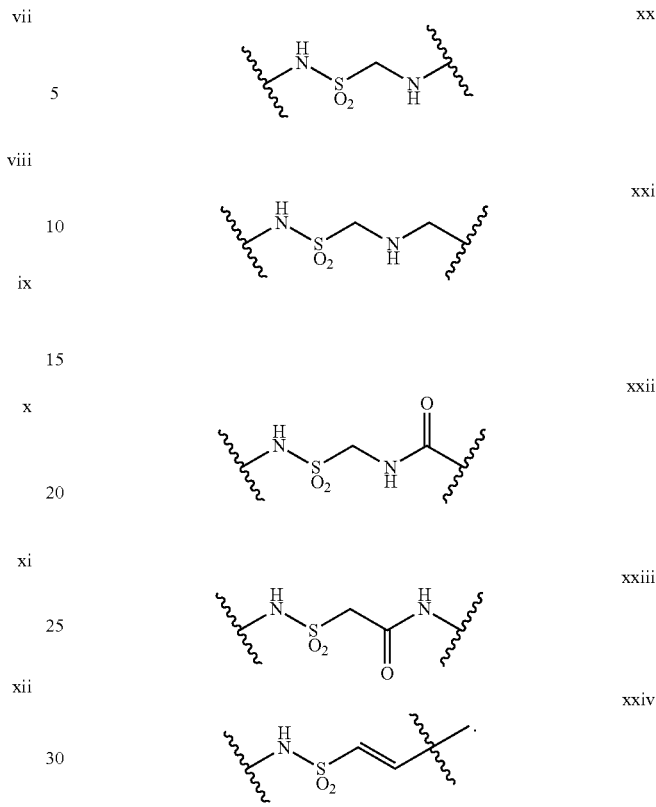

15. The compound of claim 4, wherein X is O.

16. The compound of claim 4, wherein X is O, m is 1, and $R^2$ is an optionally substituted group selected from a monocyclic 3-8-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur.

17. The compound of claim 4, wherein $R^3$ is —$OR^{3b}$, —$SR^{3c}$, —$V_1$-$T_1$-$R^{3d}$, or $T_1$-$R^{3d}$, wherein $V_1$ is O or S, and $T_1$ is —$CH_2$— or —$CH_2$—$CH_2$—.

18. The compound of claim 17, wherein $R^{3b}$, $R^{3c}$, and $R^{3d}$ are each independently an optionally substituted group selected from $C_{1-4}$alkenyl, $C_{1-4}$alkynyl, $C_{1-4}$alkyl, 5-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

19. The compound of claim 18, wherein $R^{3b}$, $R^{3c}$, and $R^{3d}$ are each independently optionally substituted $C_{1-4}$alkenyl, $C_{1-4}$alkynyl, $C_{1-4}$alkyl, or an optionally substituted group selected from:

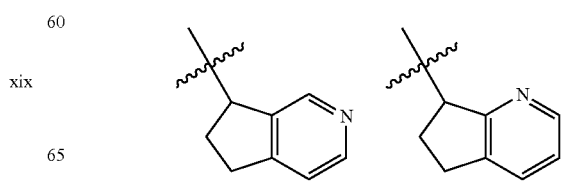

-continued

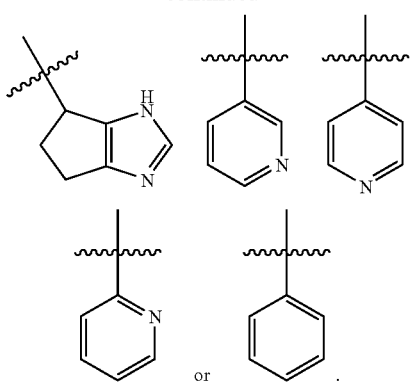

or

20. The compound of claim 17, wherein $R^{3b}$, $R^{3c}$, and $R^{3d}$ are each independently an optionally substituted ring selected from bicyclic 8-10-membered heterocyclyl having 1-5 heteroatoms independently selected from nitrogen, oxygen, or sulfur or 8-10-membered heteroaryl having 1-5 heteroatoms independently selected from nitrogen, oxygen, or sulfur.

21. The compound of claim 20, wherein $R^{3b}$, $R^{3c}$, and $R^{3d}$ are each independently optionally substituted with 1-3 occurrences of $R^{3e}$, wherein $R^{3e}$ is $R^f$, halogen, $-N(R^g)_2$, $-OR^g$, $-SR^f$, $-S(O)_2R^f$, $-COR^f$, $-COOR^g$, $-CON(R^g)_2$, $-CON(R^g)_2$, $-S(O)_2N(R^g)_2$, $-CC(O)N(R^g)_2$, $-NR'C(O)R^f$, $-NR'S(O)_2R^f$, wherein $R^f$ is an optionally substituted $C_{1-6}$ aliphatic group and $R^g$ is hydrogen or an optionally substituted $C_{1-6}$ aliphatic group.

22. The compound of claim 21, wherein $R^{3b}$, $R^{3c}$, and $R^{3d}$ are each independently optionally substituted with 1-3 occurrences of $R^{3e}$, wherein $R^{3e}$ is $C_{1-4}$aliphatic, $C_{1-4}$haloaliphatic, or halogen.

23. The compound of claim 4, wherein the compound has the structure of formula I-C:

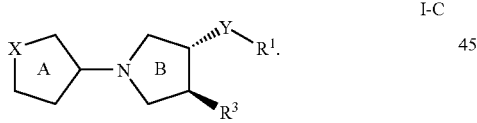

24. The compound of claim 23, wherein X is O and the compound has the structure of formula I-D:

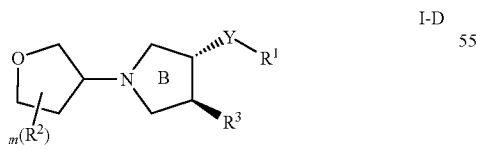

wherein:
a) $R^1$ is an optionally substituted 5-8-membered monocyclic or 7-10-membered bicyclic heterocyclyl or heteroaryl ring having 1-4 heteroatoms independently selected from N, O, or S, wherein $R^1$ is optionally substituted with 1-3 occurrences of $R^{1a}$, wherein each occurrence of $R^{1a}$ is independently halogen, $=O$, $=S$, $-CN$, $-NO_2$, $-R^{1c}$, $-N(R^{1b})_2$, $-OR^{1b}$, $-SR^{1c}$, $-S(O)R_2R^{1c}$, $-C(O)R^{1b}$, $-C(O)OR^{1b}$, $-C(O)N(R^{1b})_2$, $-S(O)_2N(R^{1b})_2$, $-OC(O)N(R^{1b})_2$, $-N(R')C(O)R^{1b}$, $-N(R')SO_2R^{1c}$, $-N(R')C(O)OR^{1b}$, $-N(R')C(O)N(R^{1b})_2$, or $-N(R')SO_2N(R^{1b})_2$, or two occurrences of $R^{1b}$ or $R^{1c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur or two occurrences of $R^{1b}$, taken together with the nitrogen atom to which they are bound, form an optionally substituted 3-7-membered heterocyclyl ring having 1-3 additional heteroatoms selected from nitrogen, oxygen, or sulfur, wherein:

each occurrence of $R^{1b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of $R^{1c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

b) Y is $-NH(CO)CH_2-$, $-NHS(O)_2CH_2-$, $-NHC(O)-$, $-NH(CO)CH_2NH-$, or $-NHS(O)_2-$;

c) m is 0 or 1, and when m is 1 $R^2$ is an optionally substituted group selected from a monocyclic 3-7-membered heterocyclyl having 1-2 heteroatoms independently selected from nitrogen, oxygen, or sulfur, a bicyclic 7-10-membered heterocyclyl having 1-2 heteroatoms independently selected from nitrogen, oxygen, or sulfur, a monocyclic 5-6-membered heteroaryl having 1-3 heteroatoms independently selected from nitrogen, oxygen, or sulfur, or a 7-10-membered heteroaryl having 1-5 heteroatoms independently selected from nitrogen, oxygen, or sulfur; and d) $R^3$ is $-OR^{3b}$, $-SR^{3c}$, $-V_1-T_1-R^{3d}$, or $T_1-R^{3d}$, wherein $V_1$ is O or S, and $T_1$ is $-CH_2-$ or $-CH_2-CH_2-$, wherein $R^{3b}$, $R^{3c}$, and $R^{3d}$ are each independently an optionally substituted group selected from $C_{1-4}$alkenyl, $C_{1-4}$alkynyl, $C_{1-4}$alkyl, 5-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

25. The compound of claim 24, wherein:
a) $R^1$ is an optionally substituted group selected from:

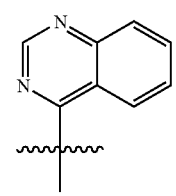

121
-continued
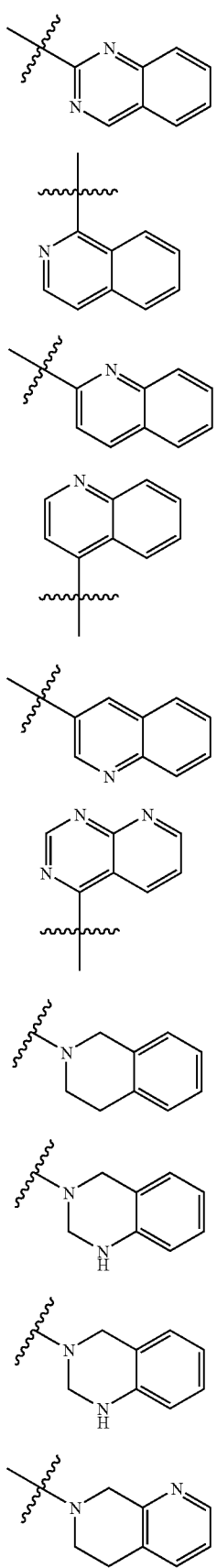
g
h
i
j
k
l
m
n
o
p
122
-continued
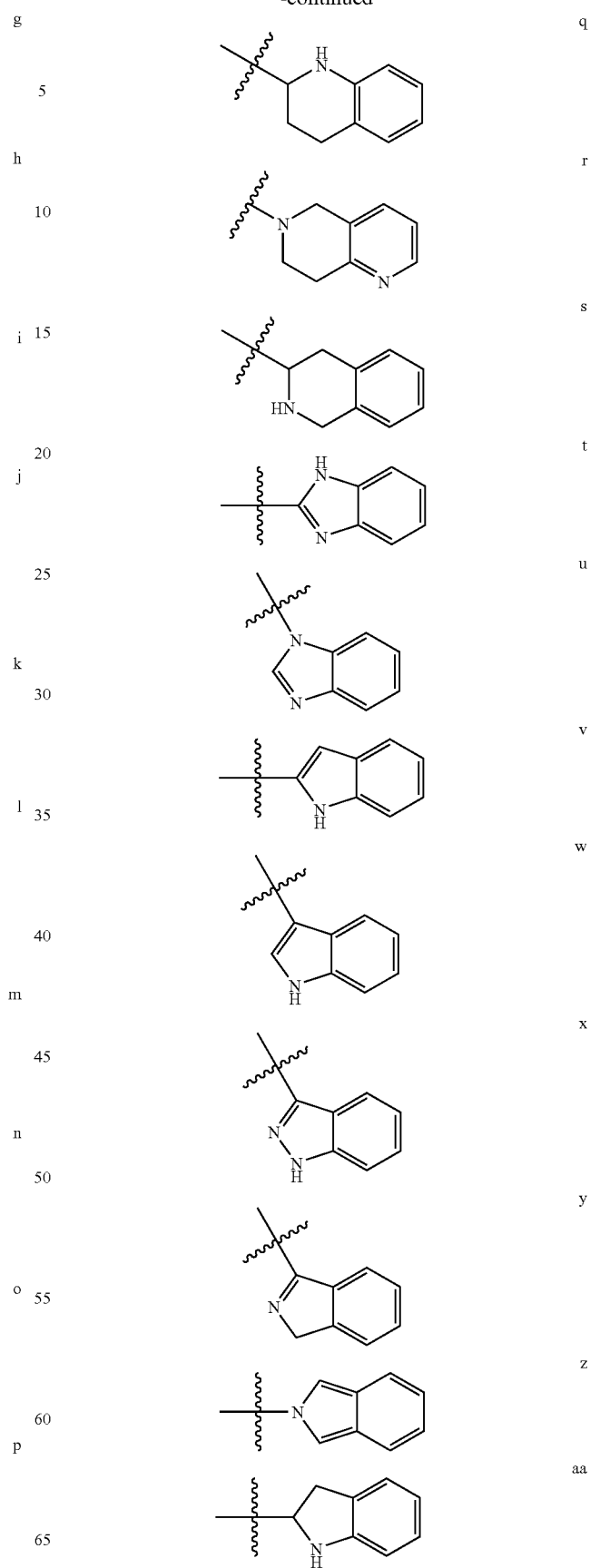
q
r
s
t
u
v
w
x
y
z
aa -continued bb
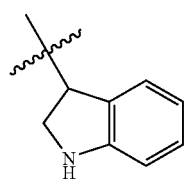

cc
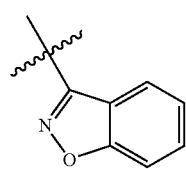

dd
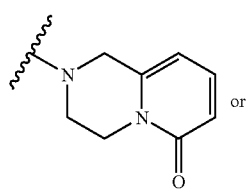 or ee
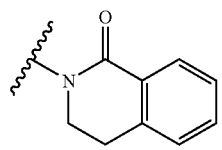

and each occurrence of $R^{1a}$ is independently =O, halogen, —$R^{1c}$, —$N(R^{1b})_2$, —$OR^{1b}$, or —$SR^{1c}$; and b) $R^{3b}$, $R^{3c}$, and $R^{3d}$ are each independently optionally substituted $C_{1-4}$alkenyl, $C_{1-4}$alkynyl, $C_{1-4}$alkyl, or an optionally substituted group selected from:

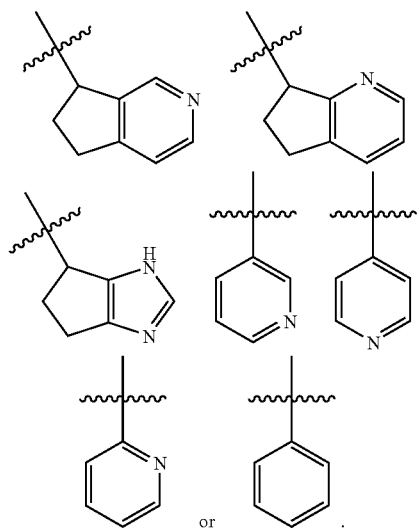

wherein $R^{3b}$, $R^{3c}$, and $R^{3d}$ are each independently optionally substituted with 1-3 occurrences of $R^{3e}$, wherein $R^{3e}$ is $C_{1-4}$aliphatic, $C_{1-4}$haloaliphatic, or halogen.

26. A pharmaceutical composition comprising a pharmaceutically acceptable carrier or diluent and a compound of formula I

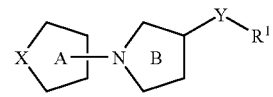 I or a pharmaceutically acceptable salt thereof, wherein:
Y is —$Y_1$—$Y_2$—, wherein:
  $Y_1$ is —$SO_2N(R')$—, —$C(O)N(R')$—; —$C(O)N(R')C(O)$—, —$N(R')SO_2$—, —$N(R')SO_2N(R')$—, —$N(R')C(O)$—, —NR'C(O)N(R')—, or —$N(R')C(O)O$—; and
  $Y_2$ is absent or is an optionally substituted $C_{1-6}$ alkylene chain, wherein one or two methylene units of $Y_2$ are optionally and independently interrupted by —O—, —S—, —N(R')—, —C(O)—, —OC(O)—, —C(O)O—, —S(O)—, —S(O)$_2$—, —C(O)N(R')—, —N(R')C(O)—, —N(R')C(O)N(R')—, —N(R')C(O)O—, —OC(O)N(R')—, —N(R')S(O)$_2$—, or —S(O)$_2$N(R')—, or wherein $Y_2$, or a portion thereof, is an optionally substituted ring selected from 3-6-membered cycloaliphatic, 3-6-membered heterocyclyl having 1-3 heteroatoms independently selected from nitrogen, oxygen, or sulfur, 6-membered aryl, or 5-6-membered heteroaryl having 1-3 heteroatoms independently selected from nitrogen, oxygen, or sulfur;
  each R' is independently hydrogen or optionally substituted $C_{1-6}$aliphatic;
$R^1$ is an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
ring A is substituted at one or more carbon atoms with m independent occurrences of $R^2$;
m is 0-6;
each occurrence of $R^2$ is independently halogen, =O, =S, —CN, —$R^{2b}$, —$N(R^{2a})_2$, —$OR^{2a}$, —$SR^{2b}$, —$S(O)_2R^{2b}$, —$C(O)R^{2a}$, —$C(O)OR^{2a}$, —$C(O)N(R^{2a})_2$, —$S(O)_2N(R^{2a})_2$, —$OC(O)N(R^{2a})_2$, —$N(R')C(O)R^{2a}$, —$N(R')SO_2R^{2b}$, —$N(R')C(O)OR^{2a}$, —$N(R')C(O)N(R^{2a})_2$, or —$N(R')SO_2N(R^{2a})_2$, or two occurrences of $R^{2a}$ or $R^{2b}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{2a}$, taken together with the nitrogen atom to which they are bound, form an optionally substituted 3-7-membered heterocyclyl ring having 1-3 additional heteroatoms selected from nitrogen, oxygen, or sulfur;
  each occurrence of $R^{2a}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{2b}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

ring B is substituted with r independent occurrences of —$R^3$;

r is 0-6;

each occurrence of $R^3$ is independently —$R^{3a}$, -$T_I$-$R^{3d}$, or —$V_1$-$T_1$-$R^{3d}$, wherein:

each occurrence of —$R^{3a}$ is independently halogen, —CN, —$NO_2$, —$R^{3c}$, —$N(R^{3b})_2$, —$OR^{3b}$, —$SR^{3c}$, —$S(O)_2R^{3c}$, —$C(O)R^{3b}$, —$C(O)OR^{3b}$, —$C(O)N(R^{3b})_2$, —$S(O)_2N(R^{3b})_2$, —$OC(O)N(R^{3b})_2$, —$N(R')C(O)R^{3b}$, —$N(R')SO_2R^{3c}$, —$N(R')C(O)OR^{3b}$, —$N(R')C(O)N(R^{3b})_2$, or —$N(R')SO_2N(R^{3b})_2$, or two occurrences of $R^{3b}$ or $R^{3c}$ are optionally taken together with their intervening atom(s) to form an optionally substituted spiro, fused, or bridged ring selected from 6-membered aryl, 3-6-membered cycloaliphatic, 3-7-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur, or two occurrences of $R^{3b}$, taken together with the nitrogen atom to which they are bound, form an optionally substituted 3-7-membered heterocyclyl ring having 1-3 additional heteroatoms selected from nitrogen, oxygen, or sulfur;

each occurrence of $R^{3b}$ is independently hydrogen or an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_1$ is independently —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—;

each occurrence of $T_1$ is independently $C_{1-6}$ alkylene chain optionally substituted with $R^{3a}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein $T^1$ or a portion thereof optionally forms part of an optionally substituted 3-7 membered cycloaliphatic or heterocyclyl ring;

X is —O—;

W is absent or is a group selected from —$W_1$-$L_2$-$W_2$—, wherein $W_1$ and $W_2$ are each independently absent or are an optionally substituted $C_{1-3}$alkylene chain, and $L_2$ is absent or is a group selected from —N(R)—, —O—, —S—, —S(O)—, —S(O)$_2$—, —C(O)—, —C(O)O—, —C(O)N(R)—, —S(O)$_2$N(R)—, —OC(O)N(R)—, —N(R)C(O)—, —N(R)SO$_2$—, —N(R)C(O)O—, —N(R)C(O)N(R)—, —N(R)SO$_2$N(R)—, —OC(O)—, or —C(O)N(R)—O—, wherein R is hydrogen or $C_1$-$C_4$alkyl, provided that if $W_1$ is absent then $L_2$ is selected from —C(O)—, —C(O)O—, —C(O)O—, —S(O)—, —S(O)$_2$—, —C(O)N(R)—, or —S(O)$_2$N(R)—

$R^4$ is an optionally substituted monocyclic or bicyclic ring selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and provided that the compound is other than:
a) 1-Pyrrolidinecarboxamide, 3-[6-(4-chlorophenyl)-4-oxothieno[3,2-d]pyrimidin-3(4H)-yl]-N-methyl-N-[(3S)-1-(tetrahydro-2-oxo-3-furanyl)-3-pyrrolidinyl]-, (3S)-,
b) Penitol, 1,4-anhydro-2,3,5-trideoxy-3-[(3R)-3-[methyl[[(3S)-3-[methyl[[(4-phenoxylphenol)amino]carbonyl]amino]-1-pyrrolidinyl]carbonyl]amino]-1-pyrrolidinyl] or
c) Penitol, 1,4-anhydro-2,3,5-trideoxy-3-[(3R)-3-[methyl[[(3S)-3-[methyl[[4'-(trifluoromethyl)[1,1'-biphenyl]-4-yl]carbonyl]amino]-1-pyrrolidinyl]carbonyl]amino]-1-pyrrolidinyl].

* * * * *